(12) United States Patent
Imanishi et al.

(10) Patent No.: US 7,217,805 B2
(45) Date of Patent: May 15, 2007

(54) BICYCLONUCLEOSIDE ANALOGUES

(75) Inventors: Takeshi Imanishi, Nara (JP); Satoshi Obika, Osaka (JP)

(73) Assignee: Sankyo Company, Limited, Tokyo (JP)

( * ) Notice: Subject to any disclaimer, the term of this patent is extended or adjusted under 35 U.S.C. 154(b) by 1033 days.

(21) Appl. No.: 10/054,300

(22) Filed: Jan. 22, 2002

(65) Prior Publication Data

US 2004/0143114 A1    Jul. 22, 2004

Related U.S. Application Data

(63) Continuation-in-part of application No. PCT/JP00/04902, filed on Jul. 21, 2000.

(30) Foreign Application Priority Data

Jul. 22, 1999   (JP)   ................... 11-207170

(51) Int. Cl.
C07H 19/00 (2006.01)
C07H 21/00 (2006.01)
C07H 19/048 (2006.01)

(52) U.S. Cl. .................. 536/22.1; 536/27.1; 536/27.2; 536/27.21; 536/28.1; 536/28.4

(58) Field of Classification Search ............... 536/27.1, 536/27.2, 27.21, 28.1, 28.4
See application file for complete search history.

(56) References Cited

U.S. PATENT DOCUMENTS

| | | |
|---|---|---|
| 3,687,808 A | 8/1972 | Merigan, Jr. et al. |
| 4,689,320 A | 8/1987 | Kaji |
| 4,806,463 A | 2/1989 | Goodchild et al. |
| 5,004,810 A | 4/1991 | Draper |
| 5,166,195 A | 11/1992 | Ecker |
| 5,194,428 A | 3/1993 | Agrawal et al. |
| 5,242,906 A | 9/1993 | Pagano et al. |
| 5,248,670 A | 9/1993 | Draper et al. |
| 5,442,049 A | 8/1995 | Anderson et al. |
| 5,457,189 A | 10/1995 | Crooke et al. |
| 5,514,577 A | 5/1996 | Draper et al. |
| 5,523,389 A | 6/1996 | Ecker et al. |
| 5,580,767 A | 12/1996 | Cowsert et al. |
| 5,582,972 A | 12/1996 | Lima et al. |
| 5,582,986 A | 12/1996 | Monia et al. |
| 5,591,600 A | 1/1997 | Ecker |
| 5,591,623 A | 1/1997 | Bennett et al. |
| 5,591,720 A | 1/1997 | Anderson et al. |
| 5,607,923 A | 3/1997 | Cook et al. |
| 5,620,963 A | 4/1997 | Cook et al. |
| 5,658,891 A | 8/1997 | Draper et al. |
| 5,661,134 A | 8/1997 | Cook et al. |
| 5,681,747 A | 10/1997 | Boggs et al. |
| 5,681,944 A | 10/1997 | Crooke et al. |
| 5,691,461 A | 11/1997 | Ecker et al. |
| 5,877,309 A | 3/1999 | McKay et al. |
| 5,955,443 A | 9/1999 | Bennett et al. |
| 5,985,558 A | 11/1999 | Dean et al. |
| 6,111,094 A | 8/2000 | Bennett et al. |
| 6,127,533 A | 10/2000 | Cook et al. |
| 6,268,490 B1 | 7/2001 | Imanishi et al. |
| 6,670,461 B1 | 12/2003 | Wengel et al. |
| 6,794,499 B2 | 9/2004 | Wengel et al. |
| 7,034,133 B2 | 4/2006 | Wengel et al. |
| 2002/0147332 A1 | 10/2002 | Kaneko et al. |
| 2003/0134808 A1 | 7/2003 | Wengel et al. |
| 2003/0144231 A1 | 7/2003 | Wengel et al. |
| 2003/0207841 A1 | 11/2003 | Kaneko et al. |
| 2005/0287566 A1 | 12/2005 | Wengel et al. |

FOREIGN PATENT DOCUMENTS

WO    WO 94/08003    4/1994

(Continued)

OTHER PUBLICATIONS

Obika et al., "Synthesis of a conformationally locked AZT analogue, 3'-azido-3'-deoxy-2'-O,4'-C-methylene-5-methyluridine", Tetrahedron Letters, 40, 6465-6468, 1999.*

(Continued)

Primary Examiner—Shaojia Anna Jiang
Assistant Examiner—Traviss C. Mcintosh, III
(74) Attorney, Agent, or Firm—Frishauf, Holtz, Goodman & Chick, P.C.

(57) ABSTRACT

Bicyclonucleoside analogues which exhibit anti-AIDS activity and intermediates to produce oligonucleotide analogues which have anti-sense or anti-gene activity as well as in vivo stability. Compounds of the following formula (1) or their pharmaceutically acceptable salts.

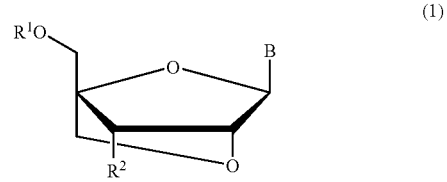

(1)

wherein $R^1$ represents a hydrogen atom or a protecting group for a hydroxy group, $R^2$ represents an azido group or an optionally protected amino group or the like, B represents a purin-9-yl or a 2-oxo-1,2-dihydropyrimidin-1-yl group, which are optionally substituted with substituents selected from the group consisting of a halogen atom, an alkyl group having 1–6 carbon atoms, a hydroxy group, a mercapto group and an amino group.

16 Claims, 1 Drawing Sheet

FOREIGN PATENT DOCUMENTS

| WO | WO 96/31557 | 10/1996 |
|---|---|---|
| WO | WO 98/39352 | 9/1998 |
| WO | WO 99/14226 | 3/1999 |

OTHER PUBLICATIONS

U.S. Appl. No. 09/925,673, Kaneko et al.
Griffiths and Nickoloff, "Keratinocyte Intercellular Adhesion Molecule-1 (ICAM-1) Expression Precedes Dermal T Lymphocytic Infiltration in Allergic Contact Dermatitis (*Rhus dermatitis*)", *Am. J. Pathology*, 1989, 135, 1045-1053.
Thuong and Helene, "Sequence-Specific Recognition and Modification of Double-Helical DNA by Oligonucleotides", *Angew. Chem. Int. Ed. Engl.*, 1993, 32, 666-690.
Englisch and Gauss, "Chemically Modified Oligonucleotides as Probes and Inhibitors", *Angewandte Chemie*, International Edition, 1991, 30, 613-722.
Manoharan et al., "Chemical Modifications to Improve Uptake and Bioavailability of Antisense Oligonucleotides", *Ann. N.Y. Acad. Sci.*, 1992, 660, 306-309.
Stetler-Stevenson et al., "Tumor Cell Interactions with the Extracellular Matrix During Invasion and Metastasis", *Annu. Rev. Cell Biol.*, 1993, 9, 541-573.
Cook, "Medicinal chemistry of antisense oligonucleotides- future opportunities", *Anti-Cancer Drug Design*, 1991, 6, 585-607.
Morassutti et al., "Reduction of *mdr1* Gene Amplification in Human Multidrug-Resistant LoVo DX Cell Line Is Promoted by Triple Helix-Forming Oligonucleotides", *Antisense & Nucleic Acid Drug Development*, 1999, 9, 261-270.
Sanghvi, "Heterocyclic Base Modifications in Nucleic Acids and their Applications in Antisense Oligonucleotides", *Antisense Research and Applications*, Ed. S.T. Crooke and B. Lebleu, CRC Press, 1993, 273-288 (Chapter 25).
Shiohara et al., "Fixed Drug Eruption", *Arch. Dermatol.*, 1989, 125, 1371-1412.
Ebbinghaus et al., "Inhibition of Transcription Elongation in the HER-2/neu Coding Sequence by Triplex-Directed Covalent Modification of the Template Strand", *Biochemistry*, 1999, 38, 619-628.
Catapano et al., "Inhibition of Gene Expression and Cell Proliferation by Triple Helix-Forming Oligonucleotides Directed to the c-myc Gene", *Biochemistry*, 2000, 39, 5126-5138.
Mishra et al., "Improved leishmanicidal effect of phosphorotioate antisense oligonucleiotides by LDL-mediated delivery", *Biochimica et Biophysica Acta*, 1995, 1264, 229-237.
Svinarchuk et al., "Inhibition of HIV proliferation in MT-4 cells by antisense oligonucleotide conjugated to lipophilic groups", *Biochimie*, 1993, 75, 49-54.
Manoharan et al., "Introduction of a lipophilic thioether tether in the minor groove of nucleic acids for antisense applications", *Bioorganic & Medicinal Chemistry Letters*, 1993, 3, 2765-2770.
Manoharan et al., "Cholic Acid-Oligonucleotide Conjugates for Antisense Applications", *Bioorganic & Medicinal Chemistry Letters*, 1994, 4, 1053-1060.
Yu et al., "Specific Inhibition of PCR by Non-Extendable Oligonucleotides Using a 5' to 3' Exonuclease-Deficient DNA Polymerase", *Biotechniques*, 1997, 23, 714-720.
Lisby et al., "Intercellular adhesion molecule-I (ICAM-I) expression correlated to inflammation", *Brit. J. Dermatol.*, 1989, 120, 479-484.
Tam and Fraser-Reid, "A synthetic route to 4-C-methyl-*xylo*-furanose", *Can. J. Chem.*, 1979, 57, 2818-2822.
Resnicoff et al., "Inhibition of rat C6 glioblastoma tumor growth by expression of insulin-like growth factor I receptor antisense mRNA", *Cancer Immunol. Immunother.*, 1996, 42, 64-68.
Maher III, "Prospects for the Therapeutic Use of Antigene Oligonucleotides", *Cancer Investigation*, 1996, 14(1), 66-82.
Resnicoff et al., "Rat Glioblastoma Cells Expressing an Antisense RNA to the Insulin-like Growth Factor-1 (IGF-1) Receptor are Nontumorigenic and Induce Regression of Wild-Type Tumors", *Cancer Research*, 1994, 54, 2218-2222.

Pass et al., "Inhibition of Hamster Mesothelioma Tumorigenesis by an Antisense Expression Plasmid to the Insulin-like Growth Factor-1 Receptor", *Cancer Research*, 1996, 56, 4044-4048.
Hua and Muschel, "Inhibition of Matrix Metalloproteinase 9 Expression by a Ribozyme Blocks Metastasis in a Rat Sarcoma Model System", *Cancer Research*, 1996, 56, 5279-5284.
Brimacombe and Ching, "Nucleophilic Displacement Reactions in Carbohydrates", *Carbohydrate Research*, 1968, 8, 82-88.
Boggemeyer et al., "*Borrelia burgdorferi* Upregulates the Adhesion Molecules E-selectin, P-selectin, ICAM-1 and VCAM-1 on Mouse Endothelioma Cells in vitro", *Cell Adhesion and Communication*, 1994, 2, 145-157.
Kerr et al., "TGF-β1 Inhibition of Transin/Stromelysin Gene Expression is Mediated through a Fos Binding Sequence", *Cell*, 1990, 61, 267-278.
Singh et al., "LNA (locked nucleic acids): synthesis and high-affinity nucleic acid recognition", *Chem. Commun.*, 1998, 4, 455-456.
Birkendal-Hansen, "Proteolytic remodeling of extracellular matrix", *Current Opinion in Cell Biology*, 1995, 7, 728-735.
Leroith et al., "Molecular and Cellular Aspects of the Insulin-Like Growth Factor I Receptor", *Endocrine Reviews*, 1995, 16, 143-163.
Kabanov et al., "A new class of antivirals: antisense oligonucleotides combined with a hydrophoic substitutent effectively inhibit influenza virus reproduction and synthesis of virus-specific proteins in MDCK cells", *FEBS Lett.*, 1990, 259, 327-330.
Pierre Martin, "Ein Zugang zu 2'-*O*-Alkylribonucleosiden und Eigenschaften deren Oligonucleotide", *Helv. Chim. Acta*, 1995, 78, 486-504.
Delisser et al., "Molecular and functional aspects of PECAM-1/CD31", *Immunology Today*, 1994, 15, 490-495.
Hurtenbach et al., "Prednisolone Reduces Experimental Arthritis, and Inflammatory Tissue Destruction is Scid Mice Infected with *Borrelia burgdorferi*", *Int. J. Immunopharmac.*, 1996, 18, 281-288.
Himelstein et al., "Metalloproteinases in Tumor Progression: The Contribution of MMP-9", *Invasion Metastasis*, 1994, 14, 246-258.
Ho et al., "Treatment of severe lichen planus with cyclosporine", *J. Am. Acad. Dermatol.*, 1990, 22, 64-68.
Gum et al., "Stimulation of 92-kDa Gelatinase B Promoter Activity by *ras* Is Mitoge-activated Protein Kinase Kinase 1-independent and Requires Multiple Transcription Factor Binding Sites Including Closely Space PEA3/ets and AP-1 Sequences", *J. Biol. Chem.*, 1996, 271, 10672-10680.
Litwin et al., "Novel Cytokine-independent Induction of Endothelial Adhesion Molecules Regulated by Platelet/Endothelial Cell Adhesion Molecule (CD31)", *J. Cell Biol.*, 1997, 139, 219-228.
Newman, "The Biology of PECAM-1", *J. Clin. Invest.*, 1997, 99, 3-8.
Hakugawa et al., "The Inhibitory Effect of Anti-Adhesion Molecule Antibodies on Eosinophil Infiltration in Cutaneous Late Phase Response in Balb/c Mice Sensitized with Ovalbumin (OVA)", *J. Dermatol.*, 1997, 24, 73-79.
Ouwerkerk-Mahadevan et al., "Isoenzyme-Selective Inhibition of Glutathione Conjugation in Vivo: Selective Inhibition of the Conjugation of S-2-Bromoisovalerylurea in the Rat", *J. Pharmacol. Exp. Therapeut.*, 1996, 276, 923-928.
Wahlestedt et al., "Antisense oligodeoxynucleotides to NMDA-R1 receptor channel protect cortical neurons from excitotoxicity and reduce focalischaemic infarctions", *Nature*, 1993, 363, 260-263.
Demers et al., "Enhanced PCR amplification of VNTR locus D1S80 using peptide nucleic acid (PNA)", *Nucleic Acids Research*, 1995, 23, 3050-3055.
Chen et al., "Synthesis of oligodeoxyribonucleotide N3'-P5' phosphoramidates", *Nucleic Acids Research*, 1995, 23, 2661-2668.
Shea et al., "Synthesis, hybridization properties and antiviral activity of lipid-oligodeoxynucleotide conjugates", *Nucleic Acids Research*, 1990, 18, 3777-3783.
Oberhauser and Wagner, "Effective incorporation of 2'-O-methyl-oligoribonucleotides into liposomes and enhanced cell association through modification with thiocholesterol", *Nucleic Acids Research*, 1992, 20, 533-538.
Surzhykov and Krayevsky, "Novel 4'-Branched Nucleosides", *Nucleosides & Nucleotides*, 1994, 13, 2283-2305.

Manoharan et al., "Oligonucleotide conjugates: alteration of the pharmacokinetic properties of antisense agents", *Nucleosides & Nucleotides*, 1995, 14, 969-973.

Regezi et al., "Vascular adhesion molecules in oral lichen planus", *Oral Surg. Oral Med. Oral Pathol.*, 1996, 81, 682-690.

Hegemann and Mahrle, "Biochemical Pharmacology of Protein Kinase C and its Relevance for Dermatology", *Pharmacology of the Skin*, Ed. H. Mukhtar, CRC Press, Boca Raton, FL., 1992, 357-368.

Bernhard et al., "Direct evidence linking expression of matrix metalloproteinase 9 (92-kDa gelatinase/collagenase) to the metastatic phenotype in transformed rat embryo cells", *Proc. Natl. Acad. Sci.*, 1994, 91, 4293-4297.

Porreca et al., "A comparison of the potential role of the tetrodotoxin-insensitive sodium channels, PN3/SNS and NaN/SNS2, in rat models of chronic pain", *Proc. Natl. Acad. Sci.*, 1999, 96, 7640-7644.

Dean and McKay, "Inhibition of protein kinase C-α expression in mice after systemic administration of phosphorothioate antisense oligodeoxynucleotides", *Proc. Natl. Acad. Sci.*, 1994, 91, 11762-11766.

Rininsland et al., "Suppression of insulin-like growth factor type I receptor by a triple-helix strategy inhibits IGF-I transcription and tumorigenic potential of rat C6 glioblastoma cells", *Proc. Natl. Acad. Sci.*, 1997, 94, 5854-5859.

Letsinger et al., "Cholesterol-conjugated oligonucleotides: Synthesis, properties, and activity as inhibitors of replication of human immunodeficiency virus in cell culture", *Proc. Natl. Acad. Sci.*, 1989, 86, 6553-6556.

Giovannangeli et al., "Triple-helix formation by oligonucleotides containing the three bases thymine, cytosine, and guanine", *Proc. Natl. Acad. Sci.*, 1992, 89, 8631-8635.

Rubin and Baserga, "Biology of Disease: Insulin-Like Growth Factor-I Receptor", *Laboratory Investigation*, 1995, 73, 311-331.

Milner, "Charles Darwin and Associates, Ghostbusters", *Scientific American*, 1996, 275, 72-77.

Byne, "The Biological Evidence Challenged", *Scientific American*, May 1994, 50-55.

Wahlestedt et al., "Modulation of Anxiety and Neuropeptide Y-Y1 Receptors by Antisense Oligodeoxynucleotides", *Science*, 1993, 259, 528-531.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", *Tetrahedron*, 1998, 54, 3607-3630.

Iyer et al., "A Novel Nucleoside Phosphoramidite Synthon Derived from 1$R$,2$S$-Ephedrine", *Tetrahedron Asymmetry*, 1995, 6, 1051-1054.

Manoharan et al., "Lipidic Nucleic Acids", *Tetrahedron Letters*, 1995, 36, 3651-3654.

Obika et al., "Stability and structural features of the duplexes containing nucleoside analogues with a fixed N-type conformation, 2'-$O$,4'-$C$-methylenerionucleosides", *Tetrahedron Letters*, 1998, 39, 5401-5404.

Obika et al., "Synthesis of a conformationally locked AZT analogue, 3'-azido-3'-deoxy-2'-$O$,4'-$C$-methylene-5-methyluridine", *Tetrahedron Letters*, 1999, 40, 6465-6468.

Berkow et al., eds, *The Merck Manual of Diagnosis and Therapy*, 15th Ed., Rahway, NJ, 1987, 2263-2277.

Berkow et al., eds, *The Merck Manual of Diagnosis and Therapy*, 15th Ed., Rahway, NJ, 1987, 2283-2285.

Berkow et al., eds, *The Merck Manual of Diagnosis and Therapy*, 15th Ed., Rahway, NJ, 1987, 2286-2292.

Berkow et al., eds, *The Merck Manual of Diagnosis and Therapy*, 15th Ed., Rahway, NJ, 1987, 2301-2310.

Albert and Morris, "Antisense knockouts: molecular scalpels for the dissection of signal transduction", *Trends in Pharmacological Sciences*, 1994, 15, 250-254.

* cited by examiner

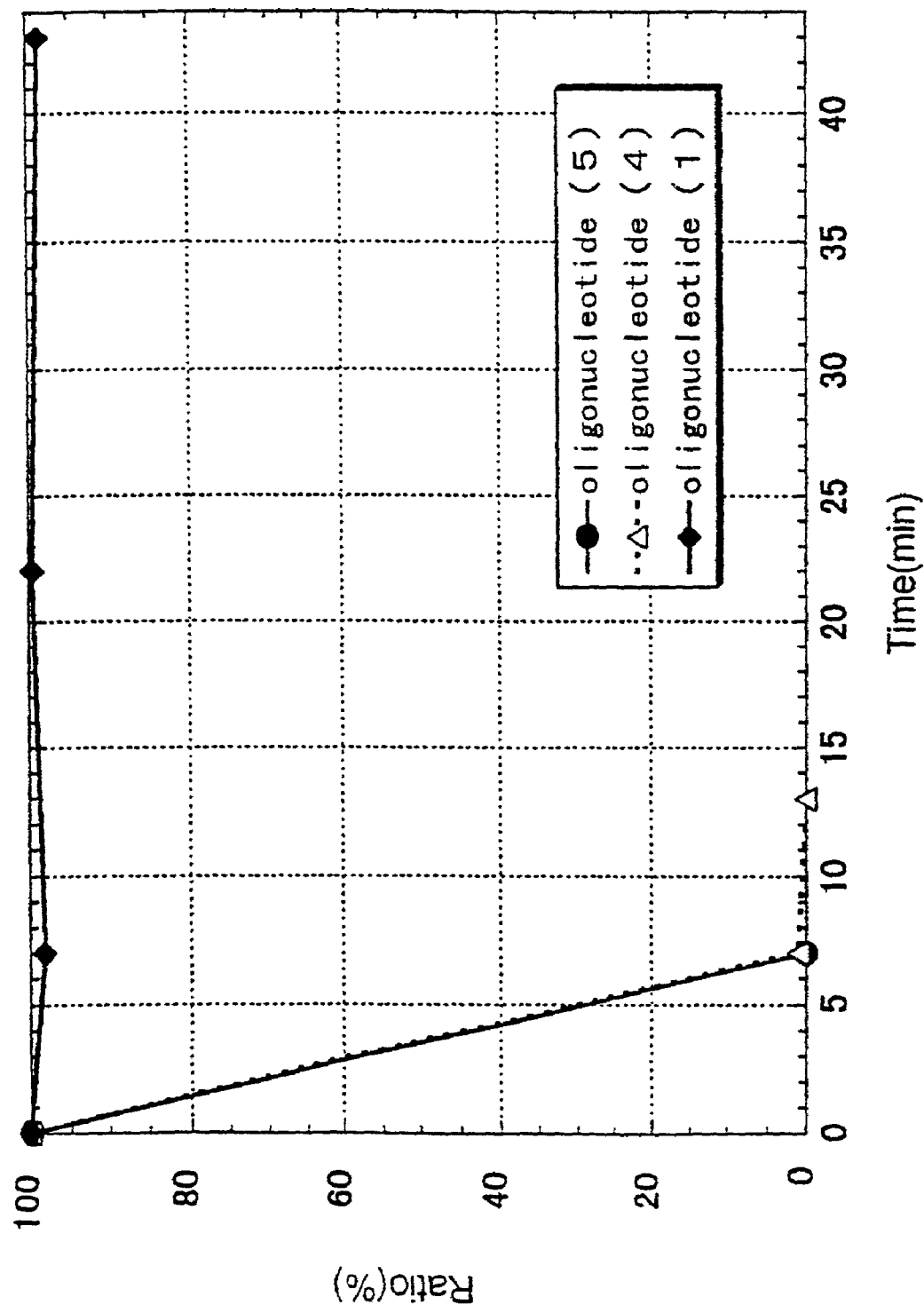

BICYCLONUCLEOSIDE ANALOGUES

This application is a continuation-in-part application of International Application No. PCT/JP00/04902, filed Jul. 21, 2000.

BACKGROUND OF THE INVENTION

1. Field of the Invention

This invention relates to novel bicyclonucleoside analogues which are useful for synthesis of non-natural oligonucleotide analogues which exhibit excellent anti-sense or anti-gene activity and in vivo stability.

This invention relates to novel oligonucleotide analogues which have one or more of said bicyclonucleoside moieties.

Further, this invention relates to novel modified bicyclonucleoside analogues which exhibit anti-AIDS activity.

2. Background Art

Oligonucleotides having excellent anti-sense or anti-gene activities and in vivo stability have been expected to be useful medicaments.

However, it is well known that natural oligonucleotides are rapidly decomposed by various nucleases in the blood or cells.

To solve these problems, numerous non-natural oligonucleotide analogues have been synthesized, and it has been tried to develop them as medicaments. For example, oligonucleotides wherein the oxygen atom binding to the phosphorus atom of the phosphodiester linkage is substituted by a sulfur atom, a methyl group, or a boron atom, are known. Further, oligonucleotides whose sugar and/or base moieties are chemically modified are also known.

More concretely, ISIS Co. has developed a thioate oligonucleotide, ISIS2922, as a therapeutic agent for retinitis infected by human cytomegalovirus and this has been sold as "VITRAVENE" (trade name in the United States).

Any non-natural oligonucleotide analogues described above, however, have not been fully satisfactory due to their insufficient potency of anti-sense or anti-gene activity, (i.e., ability to form complementary strands with mRNA or DNA) and stability to various nucleases, and due to side effects caused by non-selective binding to various proteins in vivo. Thus it has been desired to develop non-natural oligonucleotide analogues having more potent anti-sense or anti-gene activities, in vivo stability, and fewer side effects.

Compounds having a dioxabicyclo[2,2,1]heptane moiety which is related to that of the present invention and which is shown below are described in WO98/39352. These compounds differ from the compounds of the present invention in the substituent at the 3' position of ribose. Further, it has not been known that these compounds exhibit anti-AIDS activity.

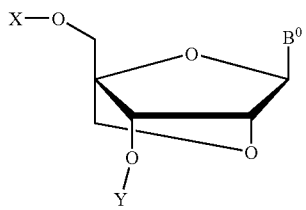

wherein $B^o$ indicates a pyrimidine or purine nucleic acid base or their analogues, X and Y are the same or different and each represents a hydrogen atom, an alkyl group, an alkenyl group, an alkynyl group, a cycloalkyl group, an aralkyl group, an aryl group, an acyl group or a silyl group.

An objective of the present invention is to provide novel bicyclonucleoside analogues which are useful for synthesis of non-natural oligonucleotides which exhibit excellent anti-sense or anti-gene activity and in vivo stability.

An objective of the present invention is also to provide novel oligonucleotide analogues having 1 or more relevant bicyclonucleoside moieties.

Furthermore, another objective of the present invention is to provide novel bicyclonucleoside analogues having anti-AIDS activity.

The present inventors have performed painstaking research to complete these objectives, and found that novel bicyclonucleoside analogues having a 2'-O,4'-C-methylene moiety are important intermediate compounds to synthesize non-natural oligonucleotides which have excellent anti-sense or anti-gene activity, as well as in vivo stability. Further, the present inventors found that the novel oligonucleotide analogues having one or more of said bicyclonucleoside moieties exhibit excellent anti-sense or anti-gene activity as well as in vivo stability. Further, said bicyclonucleoside analogues have excellent anti-AIDS activity. Thus the present inventors have completed the present invention.

SUMMARY OF THE INVENTION

1) The novel bicyclonucleoside analogues are the compounds represented by the general formula (1) or their pharmaceutically acceptable salts,

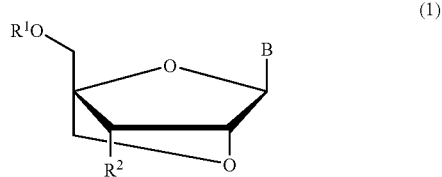

wherein $R^1$ represents a hydrogen atom, a protecting group for a hydroxy group in nucleic acid synthesis, a phosphoric acid group, a phosphoric acid group protected with a protecting group in nucleic acid synthesis, or a group represented by the formula $—P(R^{4a})R^{4b}$, wherein $R^{4a}$ and $R^{4b}$ are the same or different and each represents a hydroxy group, a hydroxy group protected with a protecting group in nucleic acid synthesis, a mercapto group, a mercapto group protected with a protecting group in nucleic acid synthesis, an amino group, an amino group protected with a protecting group in nucleic acid synthesis, an alkoxy group having 1–6 carbon atoms, an alkylthio group having 1–6 carbon atoms, a cyanoalkoxy group having 1–7 carbon atoms, or an amino group substituted by an alkyl group having 1–6 carbon atoms, $R^2$ represents an azido group, an amino group, or a group represented by the formula $—NH—R^3$, wherein $R^3$ represents a protecting group for an amino group in nucleic acid synthesis, a phosphoric acid group, a phosphoric acid group protected with a protecting group in nucleic acid synthesis, or a group represented by the formula $—P(R^{4a})R^{4b}$, wherein $R^{4a}$ and $R^{4b}$ are the same or different and each represents a hydroxy group, a hydroxy group protected with a protecting group in nucleic acid synthesis, a mercapto group, a mercapto group protected with a protecting group in nucleic acid synthesis, an amino group, an amino group protected with a protecting group in nucleic acid synthesis, an alkoxy group having 1–6 carbon atoms, an alkylthio group having 1–6 carbon atoms, a cyanoalkoxy group having 1–7 carbon atoms or an amino group substituted by an alkyl group having 1–6 carbon atoms, B represents a purine-9-yl group or a 2-oxo-1,2-dihydropyrimidin-1-yl group each of which is optionally substituted with 1 or more substituents selected from the following α group.

α Group:
  a hydroxy group,
  a hydroxy group protected with a protecting group in nucleic acid synthesis,
  an alkoxy group having 1–6 carbon atoms,
  a mercapto group,
  a mercapto group protected with a protecting group in nucleic acid synthesis,
  an alkylthio group having 1–6 carbon atoms,
  an amino group,
  an amino group protected with a protecting group in nucleic acid synthesis,
  an amino group substituted by an alkyl group having 1–6 carbon atoms,
  an alkyl group having 1–6 carbon atoms, and
  a halogen atom.

Among the compounds of the present invention, preferred compounds are as follows;

2) Compounds wherein $R^1$ represents a hydrogen atom, an aliphatic acyl group, an aromatic acyl group, a silyl group, a methyl group substituted by 1 to 3 aryl groups, or a methyl group substituted by 1 to 3 aryl groups wherein the aryl rings are substituted by a lower-alkyl group, a lower-alkoxy group, a halogen atom or a cyano group.

3) Compounds wherein $R^1$ represents a hydrogen atom, a silyl group, a methyl group substituted by 1 to 3 aryl groups, or a methyl group substituted by 1 to 3 aryl groups wherein the aryl rings are substituted by a lower-alkyl group, a lower-alkoxy group, a halogen atom or a cyano group.

4) Compounds wherein $R^1$ represents a hydrogen atom, a trimethylsilyl group, a t-butyldimethylsilyl group, a t-butyldiphenylsilyl group, a benzyl group, a triphenylmethyl group, a 4-methoxybenzyl group, a 4-methoxyphenyldiphenylmethyl group, a 4,4'-dimethoxytriphenylmethyl group, or a 4,4',4"-trimethoxytriphenylmethyl group.

5) Compounds wherein $R^2$ represents an azido group, an amino group, or a group represented by the formula —NH—$R^3$, wherein $R^3$ represents an aliphatic acyl group, an aromatic acyl group, a methyl group substituted by 1 to 3 aryl groups, a methyl group substituted by 1 to 3 aryl groups wherein the aryl rings are substituted by lower-alkyl group, lower-alkoxy group, halogen atom, or cyano group, a silyl group, a phosphoroamidite group, a phosphonyl group, a phosphoric acid group or a phosphoric acid group substituted by a protecting group in nucleic acid synthesis, 6) Compounds wherein $R^2$ represents an azido group, an amino group, or a group represented by the formula —NH—$R^3$, wherein $R^3$ represents an acetyl group, a trifluoroacetyl group, a benzoyl group, a benzyl group, a p-methoxybenzyl group, a tert-butyldiphenylsilyl group, a group represented by the formula —P(OC$_2$H$_4$CN)(N(CH(CH$_3$)$_2$)$_2$), a group represented by a formula —P(OCH$_3$)(N(CH(CH$_3$)$_2$)$_2$), a phosphonyl group, or a 2-chlorophenyl- or a 4-chlorophenylphosphoric acid group, 7) Compounds wherein $R^2$ represents an azido group or an amino group.

8) Compounds where B represents 6-aminopurin-9-yl (i.e., adeninyl), 6-amino-purin-9-yl wherein the amino group is protected with a protecting group in nucleic acid synthesis, 2,6-diaminopurin-9-yl wherein one or both amino group(s) are protected with a protecting group in nucleic acid synthesis, 2-amino-6-chloropurin-9-yl, 2-amino-6-chloropurin-9-yl wherein the amino group is protected with a protecting group in nucleic acid synthesis, 2-amino-6-fluoropurin-9-yl, 2-amino-6-fluoropurine-9-yl wherein the amino group is protected with a protecting group in nucleic acid synthesis, 2-amino-6-bromopurine-9-yl, 2-amino-6-bromopurin-9-yl wherein the amino group is protected with a protecting group in nucleic acid synthesis, 2-amino-6-hydroxypurin-9-yl (i.e., guaninyl), 2-amino-6-hydroxypurin-9-yl wherein the amino group is protected with a protecting group in nucleic acid synthesis, 6-amino-2-methoxypurin-9-yl, 6-amino-2-methoxypurin-9-yl wherein the amino group is protected with a protecting group in nucleic acid synthesis, 6-amino-2-chloropurin-9-yl, 6-amino-2-chloropurin-9-yl wherein the amino group is protected with a protecting group in nucleic acid synthesis, 6-amino-2-fluoropurin-9-yl, 6-amino-2-fluoropurin-9-yl wherein the amino group is protected with a protecting group in nucleic acid synthesis, 2,6-dimethoxypurin-9-yl, 2,6-dichloropurin-9-yl, 6-mercaptopurin-9-yl, 6-mercaptopurine-9-yl wherein the mercapto group is protected with a protecting group in nucleic acid synthesis, 2-oxo-4-amino-1,2-dihydropyrimidin-1-yl (i.e., cytosinyl), 2-oxo-4-amino-1,2-dihydropyrimidin-1-yl wherein the amino group is protected with a protecting group in nucleic acid synthesis, 4-amino-2-oxo-5-fluoro-1,2-dihydropyrimidin-1-yl, 4-amino-2-oxo-5-fluoro-1,2-dihydropyrimidin-1-yl wherein the amino group is protected with a protecting group in nucleic acid synthesis, 4-amino-2-oxo-5-chloro-1,2-dihydropyrimidin-1-yl, 4-amino-2-oxo-5-chloro-1,2-dihydropyrimidin-1-yl wherein the amino group is protected with a protecting group in nucleic acid synthesis, 2-oxo-4-methoxy-1,2-dihydropyrimidin-1-yl, 2-oxo-4-mercapto-1,2-dihydropyrimidin-1-yl, 2-oxo-4-mercapto-1,2-dihydropyrimidin-1-yl wherein the mercapto group is protected with a protecting group in nucleic acid synthesis, 2,4-dihydroxypyrimidin-1-yl (i.e., uracilyl), 2,4-dihydroxy-5-methylpyrimidin-1-yl (i.e., thyminyl), 4-amino-5-methyl-2-oxo-1,2-dihydropyrimidin-1-yl, or 4-amino-5-methyl-2-oxo-1,2-dihydropyrimidin-1-yl group wherein the amino group is protected with a protecting group in nucleic acid synthesis.

9) Compounds wherein B represents 6-benzoylaminopurin-9-yl, adeninyl, 2-benzoylamino-6-hydroxypurin-9-yl, guaninyl, 2-oxo-4-benzoylamino-1,2-dihydropyrimidin-1-yl, cytosinyl, uracilyl or thyminyl.

Compounds in which $R^1$ is selected from the above 2) to 4) and $R^2$ is selected from the above 5) to 7) and B is selected from the above 8) or 9) are also preferred. Compounds where $R^1$ is selected from 2), $R^2$ is selected from 5), and B is selected from 8), and where $R^1$ is selected from 3), $R^2$ is selected from 6), and B is selected from 8), and where $R^1$ is selected from 4), $R^2$ is selected from 6), and B is selected from 9) are particularly preferred.

The novel oligonucleotide analogues of the present invention are as follows:

(1) Oligonucleotide analogues and pharmacetuically acceptable salts thereof having 1 or more structural units of formula (1a), provided that when an oligonucleotide has two or more structural units of formula (1a), each B is the same or different

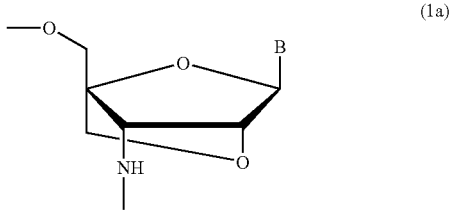

wherein
B represents a purin-9-yl group or a 2-oxo-1,2-dihydropyrimidin-1-yl group which may be substituted with substituents selected from α group below.
α Group:
  a hydroxy group,
  a hydroxy group protected with a protecting group in nucleic acid synthesis,
  an alkoxy group having 1–6 carbon atoms,
  a mercapto group,
  a mercapto group protected with a protecting group in nucleic acid synthesis,
  an alkylthio group having 1–6 carbon atoms,
  an amino group,
  an amino group protected with a protecting group in nucleic acid synthesis,
  an amino group substituted by alkyl group having 1–6 carbon atoms,
  an alkyl group having 1–6 carbon atoms, and
  a halogen atom.

Herein, "oligonucleotide analogues" represent non-natural oligonucleotides in which nucleoside units of a natural oligonucleotide are substituted with 1 or more nucleoside moieties having the above structure (1a). For example, the oligonucleotide analogues involve modified sugar derivatives, thioate derivatives in which phosphodiester-binding sites are thioated, esters in which the phosphoric acid moiety is esterified, and amide derivatives in which an amino group in a purine base is amidated as other nucleoside or nucleotide moieties.

Among the novel oligonucleotide analogues of the present invention, preferred oligonucleotide analogues are compounds and their pharmaceutically acceptable salts, wherein:
2) B is a 6-aminopurin-9-yl group (i.e., an adeninyl group), a 6-aminopurin-9-yl group wherein the amino group is protected with a protecting group in nucleic acid synthesis, a 2,6-diaminopurin-9-yl group, a 2-amino-6-chloropurin-9-yl group, a 2-amino-6-chloropurin-9-yl group wherein the amino group is protected with a protecting group in nucleic acid synthesis, a 2-amino-6-fluoropurin-9-yl group, a 2-amino-6-fluoropurin-9-yl group wherein the amino group is protected with a protecting group in nucleic acid synthesis, a 2-amino-6-bromopurin-9-yl group, a 2-amino-6-bromopurin-9-yl group wherein the amino group is protected with a protecting group in nucleic acid synthesis, a 2-amino-6-hydroxypurin-9-yl group (i.e., a guaninyl group), a 2-amino-6-hydroxypurin-9-yl group wherein the amino group is protected with a protecting group in nucleic acid synthesis, a 2-amino-6-hydroxypurin-9-yl group wherein the amino group and hydroxy group are protected with a protecting group in nucleic acid synthesis, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group (i.e., a cytosinyl group), a 2-oxo-4-amino-1,2-dihydropyrimidin-1-yl group wherein the amino group is protected with a protecting group in nucleic acid synthesis, a 2-oxo-4-amino-5-fluoro-1,2-dihydropyrimidin-1-yl group, a 2-oxo-4-amino-5-fluoro-1,2-dihydropyrimidin-1-yl group wherein the amino group is protected with a protecting group in nucleic acid synthesis, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group (i.e., an uracinyl group), a 2-oxo-4-hydroxy-5-methyl-1,2-dihydropyrimidin-1-yl group (i.e., a thyminyl group), a 4-amino-5-methyl-2-oxo-1,2-dihydropyrimidin-1-yl group (i.e., a 5-methylcytosinyl group), or a 4-amino-5-methyl-2-oxo-1,2-dihydropyrimidin-1-yl group wherein the amino group is protected with a protecting group in nucleic acid synthesis, and 3) compounds and their pharmaceutically acceptable salts in which B is a 6-benzoylaminopurin-9-yl group, an adeninyl group, a 2-isobutyrylamino-6-hydroxypurin-9-yl group, a guaninyl group, a 2-oxo-4-benzoylamino-1,2-dihydropyrimidin-1-yl group, a cytosinyl group, a 2-oxo-5-methyl-4-benzoylamino-1,2-dihydropyrimidin-1-yl group, a 5-methylcytosinyl group, an uracinyl group or a thyminyl group.

BRIEF DESCRIPTION OF THE DRAWING

The Figure is a graph which demonstrates the time course of changes in the amount of oligonucleotide in the presence of nucleases.

DETAILED DESCRIPTION OF THE INVENTION

The "protecting group for a hydroxy group in nucleic acid synthesis" in the definition of $R^1$ above has no limitation, as far as the protecting group can protect the hydroxy group stably in nucleic acid synthesis. Examples of protecting groups are as follows: "An aliphatic acyl group", for example, an alkylcarbonyl group such as formyl, acetyl, propionyl, butyryl, isobutyryl, pentanoyl, pivaloyl, valeryl, isovaleryl, octanoyl, decanoyl, 8-methylnonanoyl, 3-ethyloctanoyl, 3,7-dimethyloctanoyl, undecanoyl, tridecanoyl, hexadecanoyl, 14-methylpentadecanoyl, 13,13-dimethyltetradecanoyl, 1-methylheptadecanoyl, nonadecanoyl, eicosanoyl and henicosanoyl, a carboxylated alkylcarbonyl group such as succinoyl, glutaroyl, and adipoyl, a halogeno-lower-alkylcarbonyl group such as chloroacetyl, dichloroacetyl, trichloroacetyl, and trifluoroacetyl, a lower-alkoxy-lower-alkylcarbonyl group such as methoxyacetyl, and an unsaturated alkylcarbonyl group such as (E)-2-methyl-2-butenoyl; "an aromatic acyl group", for example, an arylcarbonyl group such as benzoyl, α-naphthoyl, and β-naphthoyl, a halogenoarylcarbonyl group such as 2-bromobenzoyl, 4-chlorobenzoyl, a lower-alkylated-arylcarbonyl group such as 2,4,6-trimethylbenzoyl, and 4-toluoyl, a lower-alkoxylated arylcarbonyl group such as 4-anisoyl, a carboxylated arylcarbonyl group such as 2-carboxybenzoyl, 3-carboxybenzoyl, and 4-carboxybenzoyl, a nitrated arylcarbonyl group such as 4-nitrobenzoyl, and 2-nitrobenzoyl; a lower-alkoxycarbonylated arylcarbonyl group such as 2(methoxycarbonyl) benzoyl, an arylated arylcarbonyl group such as 4-phenylbenzoyl; "a tetrahydropyranyl or tetrahydrothiopyranyl group" such as tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl; "a tetrahydrofuranyl or a tetrahydrothiofuranyl group" such as tetrahydrofuran-2-yl, and tetrahydrothiofuran-2-yl; "silyl groups", for example, a tri-lower-alkyl silyl group such as trimethylsilyl, triethylsilyl, isopropyldimethylsilyl, t-butyldimethylsilyl, methyldiisopropylsilyl, methyldi-t-butylsilyl, and triisopropylsilyl, a tri-lower-alkyl silyl group substituted by 1–2 aryl groups such as diphenylmethylsilyl, t-butyldiphenylsilyl, diphenylisopropylsilyl, and phenyldiisopropylsilyl; "a lower-alkoxymethyl group" such as methoxymethyl, 1,1-dimethyl-1-methoxymethyl, ethoxymethyl, propoxymethyl, isopropoxymethyl, butoxymethyl, and t-butoxymethyl; "a lower-alkoxylated lower-alkoxymethyl group" such as 2-methoxyethoxymethyl; "a halogeno-lower-alkoxymethyl group" such as 2,2,2-trichloroethoxymethyl, and bis(2-chloroethoxy)methyl; "a lower-alkoxylated ethyl group" such as 1-ethoxyethyl, and 1-(isopropoxy)ethyl; "a halogenated ethyl group" such as 2,2,2-trichloroethyl; "a methyl group substituted by 1 to 3 aryl groups" such as benzyl, α-naphthylmethyl, β-naphthylmethyl, diphenylmethyl, triphenylmethyl, α-naphthyldiphenylmethyl, and 9-anthrylmethyl; "a methyl group substituted by 1 to 3 aryl groups wherein the aryl ring is substituted by lower-alkyl, lower-alkoxy, halogen or cyano groups" such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 4,4',4"-trimethoxytriphenylmethyl, 2-nitrobenzyl, 4-nitrobenzyl, 4-chlorobenzyl, 4-bromobenzyl, and 4-cyanobenzyl; "a lower-alkoxycarbonyl group" such as methoxycarbonyl, ethoxycarbonyl, t-butoxycarbonyl, and isobutoxycarbonyl; "a lower-alkoxycarbonyl group substituted by a halogen atom or a tri-lower-alkylsilyl group" such as 2,2,2-trichloroethoxycarbonyl, and 2-trimethylsilylethoxycarbonyl, "an alkenyloxycarbonyl group" such as vinyloxycarbonyl, and aryloxycarbonyl; "an aralkyloxycarbonyl group wherein the aryl ring may be substituted by 1 or 2 lower-alkoxy or nitro groups" such as benzyloxycarbonyl, 4-methoxybenzyloxycarbonyl, 3,4-dimethoxydibenzyloxycarbonyl, 2-nitrobenzyloxycarbonyl, and 4-nitrobenzyloxycarbonyl.

Preferred protecting groups are an aliphatic acyl group, an aromatic acyl group, a methyl group substituted by 1 to 3 aryl groups, a methyl group substituted by 1 to 3 aryl groups wherein the aryl ring is substituted by lower-alkyl, lower-alkoxy group, halogen atom or cyano group, or a silyl group. More preferred protecting groups are acetyl group, benzoyl group, benzyl group, p-methoxybenzyl group, dimethoxytrityl group, monomethoxytrityl group or tert-butyldiphenylsilyl group.

Protecting groups in nucleic acid synthesis described as "a phosphoric acid group protected with a protecting group in nucleic acid synthesis" in the above definition of $R^1$ and $R^3$ have no limitation, as far as the protecting group can protect phosphoric acid groups in nucleic acid synthesis. Examples of the protecting groups are "a lower-alkyl group" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl; "a cyanated lower-alkyl group" such as 2-cyanoethyl, and 2-cyano-1,1-dimethylethyl; "an ethyl group substituted by a silyl group" such as 2-methyldiphenylsilylethyl, 2-trimethylsilylethyl, and 2-triphenylsilylethyl; "a halogenated lower-alkyl group" such as 2,2,2-trichloroethyl, 2,2,2-tribromoethyl, 2,2,2-trifluoroethyl, and 2,2,2-trichloro-1,1-dimethylethyl; "a lower-alkenyl group" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 2-methyl-1-butenyl, 3-methyl-2-butenyl, 1-ethyl-2-butenyl, 3-butenyl, 3-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, and 5-hexenyl; "a cycloalkyl group" such as cyclopropyl, cyclobutyl, cyclopentyl, cyclohexyl, cycloheptyl, norbornyl, and adamantyl; "a cyanated lower-alkenyl group" such as 2-cyanobutenyl; "an aralkyl group" such as benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl, and 6-naphthylhexyl, "an aralkyl group wherein the aryl ring is substituted by nitro group, and/or halogen atom" such as 4-chlorobenzyl, 2-(4-nitrophenyl)ethyl, o-nitrobenzyl, 4-nitrobenzyl, and 2,4-dinitrobenzyl, 4-chloro-2-nitrobenzyl, "an aryl group" such as phenyl, indenyl, naphthyl, phenanthrenyl, and anthracenyl; "an aryl group substituted by lower-alkyl group, halogen atom, and/or nitro group" such as 2-methylphenyl, 2,6-dimethylphenyl, 2-chlorophenyl, 4-chlorophenyl, 2,4-dichlorophenyl, 2,5-dichlorophenyl, 2-bromophenyl, 4-nitrophenyl, 4-chloro-2-nitrophenyl.

Preferred protecting groups are "a lower alkyl group", "a lower-alkyl group substituted by a cyano group", "an aralkyl group", "an aralkyl group wherein the aryl ring is substituted by nitro group and/or halogen atom", or "an aryl group substituted by lower-alkyl group, halogen atom, and/or nitro group".

More preferred groups are a 2-cyanoethyl group, a 2,2,2-trichloroethyl group, a benzyl group, a 2-chlorophenyl group or a 4-chlorophenyl group.

"Alkyl groups having 1–6 carbon atoms" in the definition of the above α group are, for example, straight or branched chain alkyl groups having 1–6 carbon atoms such as methyl, ethyl, n-propyl, isopropyl, n-butyl, isobutyl, s-butyl, tert-butyl, pentyl, and hexyl. Preferred groups are alkyl groups having 1–4 carbon atoms, and more preferred alkyl groups are alkyl groups having 1–2 carbon atoms, and the most preferred group is a methyl group.

The "protecting group for an amino group in nucleic acid synthesis" described in the definition of $R^2$ above has no limitation, as far as it can protect amino groups in nucleic acid synthesis. These protecting groups are as follows: "An aliphatic acyl group" for example, an alkylcarbonyl group such as formyl, acetyl, propionyl, butyryl, isobutyryl, pentanoyl, pivaloyl, valeryl, isovaleryl, octanoyl, decanoyl, 8-methylnonanoyl, 3-ethyloctanoyl, 3,7-dimethyloctanoyl, undecanoyl, tridecanoyl, hexadecanoyl, 14-methylpentadecanoyl, 13,13-dimethyltetradecanoyl, 1-methylheptadecanoyl, nonadecanoyl, eicosanoyl and henicosanoyl; a carboxylated-alkylcarbonyl group such as succinoyl, glutaroyl, and adipoyl; a halogeno-lower-alkylcarbonyl group such as chloroacetyl, dichloroacetyl, trichloroacetyl, and trifluoroacetyl; a lower-alkoxy-lower-alkylcarbonyl group such as methoxyacetyl, an unsaturated-alkylcarbonyl group such as (E)-2-methyl-2-butenoyl; "An aromatic acyl group", for example, an arylcarbonyl group such as benzoyl, α-naphthoyl, and β-naphthoyl; a halogeno-arylcarbonyl group such as 2-bromobenzoyl, and 4-chlorobenzoyl; a lower-alkylated-arylcarbonyl group such as 2,4,6-trimethylbenzoyl, and 4-toluoyl; a lower-alkoxylated-arylcarbonyl group such as 4-anisoyl; a carboxylated-arylcarbonyl group such as 2-carboxybenzoyl, 3-carboxybenzoyl, and 4-carboxybenzoyl; a nitrated-arylcarbonyl group such as 4-nitrobenzoyl, and 2-nitrobenzoyl; a lower-alkoxycarbonylated-arylcarbonyl group such as 2-(methoxycarbonyl)benzoyl, an arylated-arylcarbonyl group such as 4-phenylbenzoyl; "a lower-alkoxycarbonyl group" such as methoxycarbonyl, ethoxycarbonyl, t-butoxycarbonyl, and isobutoxycarbonyl; "a lower-alkoxycarbonyl group substituted by halogen atom or tri-lower-alkylsilyl group" such as 2,2,2-trichloroethoxycarbonyl, and 2-trimethylsilylethoxycarbonyl; "an alkenyloxycarbonyl group" such as vinyloxycarbonyl, and aryloxycarbonyl; "an aralkyloxycarbonyl group wherein the aryl ring may be substituted by 1–2 lower-alkoxy or nitro groups" such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl.

Among these, preferred groups are "an aliphatic acyl group", "an aromatic acyl group", or "an aralkyloxycarbonyl group wherein the aryl ring may be substituted by 1–2 lower-alkoxy or nitro groups".

More preferred groups are "an aliphatic acyl group" or "an aralkyloxycarbonyl group wherein the aryl ring may be substituted by 1–2 lower-alkoxy or nitro groups".

A particularly preferred group is a trifluoroacetyl group or benzyloxycarbonyl group.

"Phosphoramidite group" described above represents a group of formula $-P(OR^{3a})(NR^{3b}_2)$ (wherein $R^{3a}$ represents an alkyl group having 1–6 carbon atoms or cyanoalkyl group having 1–7 carbon atoms, while $R^{3b}$ represents an alkyl group having 1–6 carbon atoms).

Preferred groups are those represented by the formula $-P(OC_2H_4CN)(N(CH(CH_3)_2)_2)$ or the formula $-P(OCH_3)(N(CH(CH_3)_2)_2)$ "Halogen atom" described in the above definition of the α group is a fluorine, chlorine, bromine, or iodine atom, and preferred atoms are fluorine or chlorine atoms.

"Alkyl group having 1–6 carbon atoms" described in the above definition of $R^{4a}$, $R^{4b}$ and α group is, for example, a straight or branched chain alkyl group having 1–6 carbon atoms, such as methyl, ethyl, n-propyl, isopropyl, n-butyl, isobutyl, s-butyl, tert-butyl, pentyl and hexyl. Preferred groups are methyl or ethyl groups.

"Hydroxy group protected with a protecting group in nucleic acid synthesis" described in the above definition of $R^{4a}$, $R^{4b}$ and α group is a similar group to that described previously in the "protecting group for a hydroxy group in nucleic acid synthesis" in the above definition of $R^1$. Preferred groups are "an aliphatic acyl group" and "an aromatic acyl group", and the most preferred group is a benzoyl group.

"Mercapto group protected with a protecting group in nucleic acid synthesis" described in the above definitions of $R^{4a}$, $R^{4b}$ and α group is, for example, "a disulfide-forming group", for example an alkylthio group such as methylthio, ethylthio and tert-butylthio, and an arylthio group such as benzylthio, in addition to the groups described in the "protecting group for a hydroxy group in nucleic acid synthesis" in the definition of $R^1$.

Among these, preferred groups are "an aliphatic acyl group" or "an aromatic acyl group", and the most preferred group is a benzoyl group.

The "amino group protected with a protecting group in nucleic acid synthesis" described in the above definitions of $R^{4a}$, $R^{4b}$ and α group is a similar group to those described in the "protecting group for an amino group in nucleic acid synthesis", which has been already described in the definition of $R^2$. Preferred groups are "aliphatic acyl groups" or "aromatic acyl groups", and the most preferred group is a benzoyl group.

"Alkoxy group having 1–6 carbon atoms" described in the above definitions of $R^{4a}$, $R^{4b}$ and α group is, for example, a straight or branched chain alkoxy group having 1–6 carbon atoms, such as methoxy, ethoxy, n-propoxy, isopropoxy, n-butoxy, isobutoxy, s-butoxy, tert-butoxy, pentyloxy, and hexyloxy. Preferred groups are methoxy or ethoxy groups.

"Alkylthio group having 1–6 carbon atoms" described in the above definitions of $R^{4a}$, $R^{4b}$ and α group is, for example, a methylthio, ethylthio, propylthio, isopropylthio, butylthio, isobutylthio, s-butylthio, tert-butylthio, pentylthio or hexylthio group. Preferred groups are methylthio or ethylthio groups.

"Amino group substituted by an alkyl group having 1–6 carbon atoms" described in the above definitions of $R^{4a}$, $R^{4b}$ and α group is, for example, a methylamino, ethylamino, propylamino, isopropylamino, butylamino, isobutylamino, s-butylamino, tert-butylamino, pentylamino, hexylamino, dimethylamino, diethylamino, dipropylamino, diisopropylamino, dibutylamino, diisobutylamino, di(s-butyl)amino, di(tert-butyl)amino, dipentylamino, or dihexylamino group. Preferred groups are methylamino, ethylamino, dimethylamino or diethylamino groups.

"Cyanoalkoxy group having 1–7 carbon atoms" described in the above definition of $R^{4a}$ and $R^{4b}$ is, for example, a cyanomethoxy, cyanoethoxy, cyanopropyloxy, cyanobutyloxy, cyanopentyloxy, or cyanohexyloxy group, and the preferred group is a 2-cyanoethoxy group.

"Pharmaceutically acceptable salts thereof" described above indicates the salts of the oligonucleoside analogues (1) and the oligonucleotide analogues having the above chemical structure (1a). Among these salts, preferred salts are, for example, metal salts such as alkali metal salts, e.g., sodium salts, potassium salts, lithium salts; alkaline earth metal salts, e.g. calcium salts and magnesium salts; aluminium salts, iron salts, zinc salts, copper salts, nickel salts and cobalt salts; amine salts such as inorganic salts, e.g. ammonium salts; organic salts, e.g., t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts and tris(hydroxymethyl)aminomethane salts; inorganic acid salts such as hydrohalogenic acid salts, e.g., hydrofluoric acid salts, hydrochloric acid salts, hydrobromic acid salts and hydroiodic acid salts; nitric acid salts, perchloric acid salts, sulfuric acid salts and phosphoric acid salts; organic acid salts such as lower alkanesulfonic acid salts, e.g., methanesulfonic acid salts, trifluoromethanesulfonic acid salts and ethanesulfonic acid salts; arylsulfonic acid salts, e.g., benzenesulfonic acid salts and p-toluenesulfonic acid salts; acetic acid salts, malic acid salts, fumaric acid salts, succinic acid salts, citric acid salts, tartaric acid salts, oxalic acid salts and maleic acid salts; and amino acid salts such as glycine salts, lysine salts, arginine salts, ornithine salts, glutamic acid salts and aspartic acid salts.

Among these salts, sodium salt, potassium salt and triethylamine salt are preferred for oligonucleotide analogues containing nucleoside structure (1a), and the free form of nucleoside is preferred for nucleoside analogues (1).

Nucleoside analogues (1) and oligonucleotide analogues having the above structure (1a) in the present invention absorb or adsorb water to form hydrates when they are left in the atmosphere. These hydrates are included in the present invention.

Nucleoside analogues (1) and oligonucleotide analogues involving the above structure (1a) in the present invention absorb certain solvents to form solvates. These solvates are included in the present invention.

"The nucleoside analogue" refers to a non-natural type of a "nucleoside" in which a purine or pyrimidine group is attached to a sugar.

"The oligonucleotide analogue" refers to a non-natural type of an "oligonucleotide" derivative in which from 2 or more and up to 100 and preferably 2 to 50 and more preferably 10 to 30 "nucleosides", which may be the same or different, are bonded through a phosphodiester bond and such analogues may preferably include sugar derivatives in which the sugar moiety is modified; thioate derivatives in which the phosphodiester bond moiety is thioated (phosphorothioate bond); ester products in which a terminal phosphate moiety is esterified; and amide products in which an amino group on a purine base is amidated, phosphoramide derivatives in which the phosphodiester is amidated (phosphoramide bond), more preferably the sugar derivatives in which the sugar moiety (ribose or deoxyribose) is modified and the thioate derivatives in which the phosphodiester moiety is thioated, and phosphoramide derivatives in which the phosphodiester is amidated (phoisphoramide bond).

Naturally occurring oligonucleotides are those which occur in nature, for example, ribose and deoxyribose phosphodiester oligonucleotides having adenine, guanine, cytosine, thymine and uracil nucleobases. As used herein, "oligonucleotide analogues" are oligonucleotides that contain modified sugar, internucleoside linkage and/or nucleobase moieties. Such oligonucleotide analogs are typically structurally distinguishable from, yet functionally interchangeable with, naturally occurring or synthetic wild type oligonucleotides. Thus, non-naturally occurring oligonucleotides include all such structures which function effectively to mimic the structure and/or function of a desired RNA or DNA strand, for example, by hybridizing to a target.

The nucleosides other than formula (1a) in the oligonucleotide analogues of the present invention are any of the known nucleosides or not yet known nucleosides that are functionally interchangeable with naturally-occurring nucleosides. Preferably such nucleosides have the structure of a nucleobase and a sugar defined as follows.

Representative nucleobases include adenine, guanine, cytosine, uracil, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudouracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see especially pages 622 and 623, and in the *Concise Encyclopedia of Polymer Science and Engineering*, J. I. Kroschwitz Ed., John Wiley & Sons, 1990, pages 858–859, and Cook, *Anti-Cancer Drug Design,* 1991, 6, 585–607, each of which publications are hereby incorporated by reference in their entirety). The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Preferred 2'-groups of the sugar include H, OH, F, and O——, S——, or N-alkyl groups. One particularly preferred group includes 2'-methoxyethoxy[2'--O——CH$_2$CH$_2$OCH$_3$, also known as 2'-O-(2-methoxyethyl) or 2'-MOE] (Martin et al., *Helv. Chim. Acta,* 1995, 78, 486), i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in U.S. Pat. No. 6,127,533, the entire contents of which are herein incorporated by reference. Other preferred modifications include 2'-methoxy (2'-O——CH$_3$) and 2'-aminopropoxy (2'-OCH$_2$CH$_2$CH$_2$NH$_2$).

Sugars of nucleosides having O-substitutions on the ribosyl ring are also amenable to the present invention. Representative substitutions for ring O include S, CH$_2$, CHF, and CF$_2$, see, e.g., Secrist, et al., Abstract 21, Program & Abstracts, Tenth International Roundtable, "Nucleosides, Nucleotides and their Biological Applications", Park City, Utah, Sep. 16–20, 1992, which is hereby incorporated by reference in its entirety.

Internucleoside linkages may be any of the known internucleoside linkages, or may be any internucleoside linkage not yet known that can be incorporated into an oligonucleotide according to synthetic chemistry with which the process according to the invention is compatible. In certain preferred embodiments, the other internucleoside linkages are phosphodiester, phosphoramide or phosphorothioate linkages. In the case of phosphorothioate internucleoside linkages, the linkages may be phosphorothioate mixed enantiomers or stereoregular phosphorothioates (see Iyer et al., *Tetrahedron Asymmetry* 6: 1051–1054 (1995)).

Additional modifications may also be made at other positions on the oligonucleotide, particularly the 3' position of the sugar, on the 3' terminal nucleotide and the 5' position of 5' terminal nucleotide. For example, one additional modification of the oligonucleotides of the present invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyloxycholesterol moiety (Crooke et al., *J. Pharmacol. Exp. Ther.,* 1996, 277, 923).

Non-limiting examples of nucleosides other than of the formula (2) are as follows: adenosine, guanosine, cytidine, 5-methylcytidine, uridine, 5-methyluridine, inosine, 5(1-propynyl) cytidine, 5(1-propynyl) uridine, 2'-deoxyadenosine, 2'-deoxyguanosine, 2'-deoxycytidine, 5-methyl-2'-deoxycytidine, 2'-deoxyuridine, thymidine, 2'-deoxyinosine, 2'-deoxy-5-(1-propynyl)cytidine, 2'-deoxy-5-(1-propynyl) uridine, 2'-O-methyladenosine, 2-O-methylguanosine, 2'-O-methylcytidine, 5-methyl-2'-O-methylcytidine, 21'-O-methyluridine, 5-methyl-2'-O-methyluridine, 2'-O-methylinosine, 5-(1-propynyl)-2'-O-methylcytidine, 5-(1-propynyl)-2'-O-methyluridine, 2'-O-allyladenosine, 21'-O-allylguanosine, 2'-O-allylcytidine, 5-methyl-2'-O-allylcytidine, 2'-O-allyluridine, 5-methyl-2'-O-allyluridine, 2'-O-allylinosine, 5-(1-propynyl)-2'-O-allylcytidine, 5-(1-propynyl)-2'-O-allyluridine, 2'-O-propargyladenosine, 21-O-propargylguanosine, 2'-O-propargylcytidine, 5-methyl-2'-O-propargylcytidine, 2'-O-propargyluridine, 5-methyl-2'-O-propargyluridine, 2'-O-propargylinosine, 5-(1-propynyl)-2'-O-propargylcytidine, 5-(1-propynyl)-2'-O-allyluridine, 2'-O-(2-methoxyethyl)adenosine, 2'-O-(2-methoxyethyl)guanosine, 2'-O-(2-methoxyethyl)cytidine, 5-methyl-2'-O-(2-methoxyethyl)cytidine, 2'-O-(2-methoxyethyl)uridine, 5-methyl-2'-O-(2-methoxyethyl) uridine, 2'-O-(2-methoxyethyl)inosine, 5-(1-propynyl)-2'-O-(2-methoxyethyl)cytidine, 5-(1-propynyl)-2'-O-(2-methoxyethyl)uridine, 2'-O-(2-dimethylaminooxyethyl)adenosine, 2'-O-(2-dimethylaminooxyethyl)guanosine, 2'-O-(2-dimethylaminooxyethyl) cytidine, 5-methyl-2-O-(2-dimethylaminooxyethyl)cytidine, 2'-O-(2-dimethylaminooxyethyl) uridine, 5-methyl-2'-O-(2-dimethylaminooxyethyl) uridine, 2'-O-(2-dimethylaminooxyethyl)inosine, 5-(1-propynyl)-2'-O-(2-dimethylaminooxyethyl)cytidine, 5-(1-propynyl)-2'-O-(2-dimethylaminooxyethyl)uridine, 2'-fluoro-2'-deoxyadenosine, 2'-fluoro-2'-deoxyguanosine, 2'-fluoro-2'-deoxycytidine, 5-methyl-2'-fluoro-2'-deoxycytidine, 2'-fluoro-2'-deoxyuridine, 5-methyl-2'-fluoro-2'-deoxyuridine 2'-fluoro-2'-deoxyinosine, 5-(1-propynyl)-2'-fluoro-2'-deoxyuridine, 5-(1-propynyl)-2'-fluoro-2'-deoxyuridine, 2'-amino-2'-deoxyadenosine, 2'-amino-2'-deoxyguanosine, 2'-amino-2-deoxycytidine, 5-methyl-2'-amino-2'-deoxycytidine, 2'-amino-2'-deoxyuridine, 5-methyl-2'-amino-2'-deoxyuridine, 2'-amino-2'-deoxyinosine 5(1-propynyl)-2'-amino-2'-deoxyuridine, and 5-(1-propynyl)-2'-amino-2'-deoxyuridine.

In some preferred embodiments of the oligonucleotide analogues according to the present invention, several adjacent oligonucleotide analogues comprise two regions, which are the first and the second regions. Hereinafter "the first region" comprises one or more structural units of the formula (1a) and each nucleoside is connected by a phosphodiester bond; hereinafter the "second region" comprises one or more of a 2'-deoxynucleoside (e.g., 2'-deoxyadenosine, 2'-deoxyguanosine, 2'-deoxycytidine, thymidine, 2'-deoxyuridine, 5-substituted-2'-deoxycytidine or 5-substituted-2'-deoxyuridine) and each nucleoside is connected by a phosphodiester bond or a phosphorothioate bond.

In certain particularly preferred oligonucleotide analogues, the total number of nucleosides is from 5 to 100, more preferably 10 to 50, and the oligonucleotide analogues comprise the second region whose number of nucleoside residues is about half of the total number of nucleoside residues flanked on both sides by the first region, whose number of nucleoside is about a quarter of the total number of nucleoside residues. In this case, each nucleoside of the second region is preferably connected by a phosphorothioate bond and the bonds between the first region and the second region are phosphodiester bonds or phosphorothioate bonds.

In other certain particularly preferred oligonucleotide analogues, the total number of nucleosides is from 5 to 100, and the entire oligonucleotide analogue comprises (a) one or more of the structural units of the formula (1a) and one or more nucleosides selected from the group consisting of (b) a 2'-deoxynucleoside (e.g. 21-deoxyadenosine, 2'-deoxyguanosine, 21-deoxycytidine, thymidine, 2'-deoxyuridine, 5-substituted-2'-deoxycytidine or 5-substituted-2'-deoxyuridine) and (c) a 2'-O-methylribonucleoside (e.g., 2'-O-methyladenosine, 2'-O-methylguanosine, 2'-O-methylcytidine, 5-methyl-2'-O-methyluridine, 2'-O-methyluridine, 5-substituted-2'-O-methylcytidine or 5-substituted-2'-O-methyluridine). In this case, each every other nucleoside is a nucleoside analogue of the formula (1a) and the bonds between each nucleoside are preferably phosphodiester bonds.

Some typical examples of compound (1) of the present invention are exemplified by Tables 1 and 2 hereinbelow.

Abbreviations used in Table 1 and Table 2 are as follows; Bn: a benzyl group, Bz: a benzoyl group, Me: a methyl group, PMBn: a p-methoxybenzyl group, MMTr: a 4-methoxytriphenylmethyl group, DMTr: a 4,4'-dimethoxytriphenylmethyl group, TMTr: a 4,4'4"-trimethoxytriphenylmethyl group, TMS: a trimethylsilyl group, TBDMS: a tertbutyldimethylsilyl group, TBDPS: a tert-butyldiphenylsilyl group.

TABLE 1

[Chemical structure of compound (1')]

| Exemplification Compound number. | R¹ | R² | Rᵃ | Rᵇ |
|---|---|---|---|---|
| 1-1 | H | NH₂ | H | H |
| 1-2 | H | NH₂ | H | OH |
| 1-3 | H | NH₂ | H | SH |
| 1-4 | H | NH₂ | H | NH₂ |
| 1-5 | H | NH₂ | H | OMe |
| 1-6 | H | NH₂ | F | H |
| 1-7 | H | NH₂ | F | NH₂ |
| 1-8 | H | NH₂ | Cl | H |
| 1-9 | H | NH₂ | Cl | NH₂ |
| 1-10 | H | NH₂ | Cl | Cl |
| 1-11 | H | NH₂ | Br | H |
| 1-12 | H | NH₂ | Br | NH₂ |
| 1-13 | H | NH₂ | OH | H |
| 1-14 | H | NH₂ | OH | OH |
| 1-15 | H | NH₂ | OH | NH₂ |
| 1-16 | H | NH₂ | OMe | OMe |
| 1-17 | H | NH₂ | OMe | NH₂ |
| 1-18 | H | NH₂ | NH₂ | H |
| 1-19 | H | NH₂ | NH₂ | F |
| 1-20 | H | NH₂ | NH₂ | Cl |
| 1-21 | H | NH₂ | NH₂ | Br |
| 1-22 | H | NH₂ | NH₂ | OH |
| 1-23 | H | NH₂ | NH₂ | NH₂ |
| 1-24 | H | NH₂ | NH₂ | OMe |
| 1-25 | H | N₃ | H | H |
| 1-26 | H | N₃ | H | OH |
| 1-27 | H | N₃ | H | SH |
| 1-28 | H | N₃ | H | NH₂ |
| 1-29 | H | N₃ | H | OMe |
| 1-30 | H | N₃ | F | H |
| 1-31 | H | N₃ | F | NH₂ |
| 1-32 | H | N₃ | Cl | H |
| 1-33 | H | N₃ | Cl | NH₂ |
| 1-34 | H | N₃ | Cl | Cl |
| 1-35 | H | N₃ | Br | H |
| 1-36 | H | N₃ | Br | NH₂ |
| 1-37 | H | N₃ | OH | H |
| 1-38 | H | N₃ | OH | OH |
| 1-39 | H | N₃ | OH | NH₂ |
| 1-40 | H | N₃ | OMe | OMe |
| 1-41 | H | N₃ | OMe | NH₂ |
| 1-42 | H | N₃ | NH₂ | H |
| 1-43 | H | N₃ | NH₂ | F |
| 1-44 | H | N₃ | NH₂ | Cl |
| 1-45 | H | N₃ | NH₂ | Br |
| 1-46 | H | N₃ | NH₂ | OH |
| 1-47 | H | N₃ | NH₂ | NH₂ |
| 1-48 | H | N₃ | NH₂ | OMe |
| 1-49 | H | N₃ | H | NHBz |
| 1-50 | H | NH₂ | H | NHBz |
| 1-51 | H | N₃ | Cl | NHBz |
| 1-52 | H | N₃ | OH | NHBz |
| 1-53 | H | N₃ | OMe | NHBz |
| 1-54 | H | N₃ | NHBz | H |
| 1-55 | H | N₃ | NHBz | Cl |
| 1-56 | H | N₃ | NHBz | OH |
| 1-57 | H | NH₂ | NHBz | OH |
| 1-58 | H | N₃ | NHBz | NHBz |

TABLE 1-continued

| Exemplification Compound number. | R¹ | R² | Rᵃ | Rᵇ |
|---|---|---|---|---|
| 1-59 | H | N₃ | NHBz | OMe |
| 1-60 | Bn | N₃ | H | NHBz |
| 1-61 | Bn | N₃ | NHCOCH(CH₃)₂ | OH |
| 1-62 | PMBn | N₃ | H | NHBz |
| 1-63 | PMBn | N₃ | NHCOCH(CH₃)₂ | OH |
| 1-64 | MMTr | N₃ | H | NHBz |
| 1-65 | MMTr | N₃ | NHCOCH(CH₃)₂ | OH |
| 1-66 | DMTr | N₃ | H | NHBz |
| 1-67 | DMTr | N₃ | NHCOCH(CH₃)₂ | OH |
| 1-68 | TMTr | N₃ | H | NHBz |
| 1-69 | TMTr | N₃ | NHCOCH(CH₃)₂ | OH |
| 1-70 | TMS | N₃ | H | NHBz |
| 1-71 | TMS | N₃ | NHCOCH(CH₃)₂ | OH |
| 1-72 | TBDMS | N₃ | H | NHBz |
| 1-73 | TBDMS | N₃ | NHCOCH(CH₃)₂ | OH |
| 1-74 | TBDPS | N₃ | H | NHBz |
| 1-75 | TBDPS | N₃ | NHBz | OH |
| 1-76 | Bn | NH₂ | H | NHBz |
| 1-77 | Bn | NH₂ | NHCOCH(CH₃)₂ | OH |
| 1-78 | PMBn | NH₂ | H | NHBz |
| 1-79 | PMBn | NH₂ | NHCOCH(CH₃)₂ | OH |
| 1-80 | MMTr | NH₂ | H | NHBz |
| 1-81 | MMTr | NH₂ | NHCOCH(CH₃)₂ | OH |
| 1-82 | DMTr | NH₂ | H | NHBz |
| 1-83 | DMTr | NH₂ | NHCOCH(CH₃)₂ | OH |
| 1-84 | TMTr | NH₂ | H | NHBz |
| 1-85 | TMTr | NH₂ | NHCOCH(CH₃)₂ | OH |
| 1-86 | TMS | NH₂ | H | NHBz |
| 1-87 | TMS | NH₂ | NHCOCH(CH₃)₂ | OH |
| 1-88 | TBDMS | NH₂ | H | NHBz |
| 1-89 | TBDMS | NH₂ | NHCOCH(CH₃)₂ | OH |
| 1-90 | TBDPS | NH₂ | H | NHBz |
| 1-91 | TBDPS | NH₂ | NHCOCH(CH₃)₂ | OH |
| 1-93 | TBDPS | (MMTr)NH | NHCOCH(CH₃)₂ | OH |
| 1-94 | H | (MMTr)NH | H | NHBZ |
| 1-95 | H | (MMTr)NH | NHCOCH(CH₃)₂ | OH |
| 1-96 | P(OCH₂CH₂CN)-(N(iPr)₂) | (MMTr)NH | H | NHBZ |
| 1-97 | P(OCH₂CH₂CN)-(N(iPr)₂) | (MMTr)NH | NHCOCH(CH₃)₂ | OH |
| 1-98 | P(OCH₃)-N(iPr)₂ | (MMTr)NH | H | NHBZ |
| 1-99 | P(OCH₃)-N(iPr)₂ | (MMTr)NH | NHCOCH(CH₃)₂ | OH |
| 1-100 | TBDPS | (DMTr)NH | H | NHBZ |
| 1-101 | TBDPS | (DMTr)NH | NHCOCH(CH₃)₂ | OH |
| 1-102 | H | (DMTr)NH | H | NHBZ |
| 1-103 | H | (DMTr)NH | NHCOCH(CH₃)₂ | OH |
| 1-104 | P(OCH₂CH₂CN)-(N(iPr)₂) | (DMTr)NH | H | NHBz |
| 1-105 | P(OCH₂CH₂CN)-(N(iPr)₂) | (DMTr)NH | NHCOCH(CH₃)₂ | OH |
| 1-106 | P(OCH₃)-N(iPr)₂ | (DMTr)NH | H | NHBZ |
| 1-107 | P(OCH₃)-N(iPr)₂ | (DMTr)NH | NHCOCH(CH₃)₂ | OH |
| 1-108 | TBDPS | (Tfa)NH | H | NHBz |
| 1-109 | TBDPS | (Tfa)NH | NHCOCH(CH₃)₂ | OH |

TABLE 1-continued (1')

| Exemplification Compound number. | R¹ | R² | R^a | R^b |
|---|---|---|---|---|
| 1-110 | H | (Tfa)NH | H | NHBZ |
| 1-111 | H | (Tfa)NH | NHCOCH(CH₃)₂ | OH |
| 1-112 | P(OCH₂CH₂CN)-(N(iPr)₂) | (Tfa)NH | H | NHBz |
| 1-113 | P(OCH₂CH₂CN)-(N(iPr)₂) | (Tfa)NH | NHCOCH(CH₃)₂ | OH |
| 1-114 | P(OCH₃)-N(iPr)₂ | (Tfa)NH | H | NHBZ |
| 1-115 | P(OCH₃)-N(iPr)₂ | (Tfa)NH | NHCOCH(CH₃)₂ | OH |
| 1-116 | TBDPS | (Cbz)NH | H | NHBz |
| 1-117 | TBDPS | (Cbz)NH | NHCOCH(CH₃)₂ | OH |
| 1-118 | H | (Cbz)NH | H | NHBz |
| 1-119 | H | (Cbz)NH | NHCOCH(CH₃)₂ | OH |
| 1-120 | P(OCH₂CH₂CN)-(N(iPr)₂) | (Cbz)NH | H | NHBz |
| 1-121 | P(OCH₂CH₂CN)-(N(iPr)₂) | (Cbz)NH | NHCOCH(CH₃)₂ | OH |
| 1-122 | P(OCH₃)-N(iPr)₂ | (Cbz)NH | H | NHBz |
| 1-123 | P(OCH₃)-N(iPr)₂ | (Cbz)NH | NHCOCH(CH₃)₂ | OH |
| 1-124 | DMTr | NHP(CH2CH2CN)-(N(iPr)₂) | H | NHBz |
| 1-125 | DMTr | NHP(OCH₃)-(N(iPr)₂) | H | NHBz |
| 1-126 | DMTr | NHP(CH2CH2CN)-(N(iPr)₂) | NHCOCH(CH₃)₂ | OH |
| 1-127 | DMTr | NHP(OCH₃)-(N(iPr)₂) | NHCOCH(CH₃)₂ | OH |
| 1-128 | MMTr | NHP(CH2CH2CN)-(N(iPr)₂) | H | NHBz |
| 1-129 | MMTr | NHP(OCH₃)-(N(iPr)₂) | H | NHBz |
| 1-130 | MMTr | NHP(CH2CH2CN)-(N(iPr)₂) | NHCOCH(CH₃)₂ | OH |
| 1-131 | MMTr | NHP(OCH₃)-(N(iPr)₂) | NHCOCH(CH₃)₂ | OH |

TABLE 2

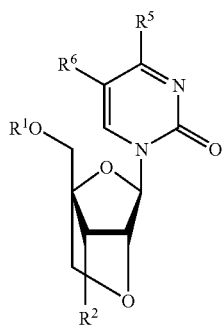

(1")

| Exemplification Compound number. | R¹ | R² | R⁵ | R⁶ |
|---|---|---|---|---|
| 2-1 | H | NH₂ | H | H |
| 2-2 | H | NH₂ | Cl | H |
| 2-3 | H | NH₂ | OH | H |
| 2-4 | H | NH₂ | OH | Me |
| 2-5 | H | NH₂ | SH | H |
| 2-6 | H | NH₂ | NH₂ | H |
| 2-7 | H | NH₂ | NH₂ | F |
| 2-8 | H | NH₂ | NH₂ | Cl |
| 2-9 | H | NH₂ | NH₂ | Me |
| 2-10 | H | NH₂ | OMe | H |
| 2-11 | H | N₃ | H | H |
| 2-12 | H | N₃ | Cl | H |
| 2-13 | H | N₃ | OH | H |
| 2-14 | H | N₃ | OH | Me |
| 2-15 | H | N₃ | SH | H |
| 2-16 | H | N₃ | NH₂ | H |
| 2-17 | H | N₃ | NH₂ | F |
| 2-18 | H | N₃ | NH₂ | Cl |
| 2-19 | H | N₃ | NH₂ | Me |
| 2-20 | H | N₃ | OMe | H |
| 2-21 | H | N₃ | NHBz | H |
| 2-22 | H | NH₂ | NHBz | H |
| 2-23 | H | N₃ | NHBz | F |
| 2-24 | H | N₃ | NHBz | Cl |
| 2-25 | H | N₃ | NHBz | Me |
| 2-26 | Bn | N₃ | OH | H |
| 2-27 | Bn | N₃ | OH | Me |
| 2-28 | Bn | N₃ | NHBz | H |
| 2-29 | PMBn | N₃ | OH | H |
| 2-30 | PMBn | N₃ | OH | Me |
| 2-31 | PMBn | N₃ | NHBz | H |
| 2-32 | MMTr | N₃ | OH | H |
| 2-33 | MMTr | N₃ | OH | Me |
| 2-34 | MMTr | N₃ | NHBz | H |
| 2-35 | DMTr | N₃ | OH | H |
| 2-36 | DMTr | N₃ | OH | Me |
| 2-37 | DMTr | N₃ | NHBz | H |
| 2-38 | TMTr | N₃ | OH | H |
| 2-39 | TMTr | N₃ | OH | Me |
| 2-40 | TMTr | N₃ | NHBz | H |
| 2-41 | TMS | N₃ | OH | H |
| 2-42 | TMS | N₃ | OH | Me |
| 2-43 | TMS | N₃ | NHBz | H |
| 2-44 | TBDMS | N₃ | OH | H |
| 2-45 | TBDMS | N₃ | OH | Me |
| 2-46 | TBDMS | N₃ | NHBz | H |
| 2-47 | TBDPS | N₃ | OH | H |
| 2-48 | TBDPS | N₃ | OH | Me |
| 2-49 | TBDPS | N₃ | NHBz | H |
| 2-50 | Bn | NH₂ | OH | H |
| 2-51 | Bn | NH₂ | OH | Me |
| 2-52 | Bn | NH₂ | NHBz | H |
| 2-53 | PMBn | NH₂ | OH | H |
| 2-54 | PMBn | NH₂ | OH | Me |
| 2-55 | PMBn | NH₂ | NHBz | H |
| 2-56 | MMTr | NH₂ | OH | H |
| 2-57 | MMTr | NH₂ | OH | Me |

TABLE 2-continued

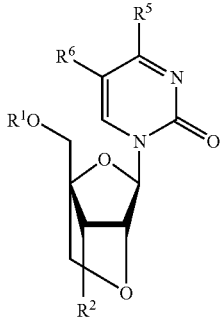

(1″)

| Exemplification Compound number. | R¹ | R² | R⁵ | R⁶ |
|---|---|---|---|---|
| 2-58 | MMTr | NH₂ | NHBz | H |
| 2-59 | DMTr | NH₂ | OH | H |
| 2-60 | DMTr | NH₂ | OH | Me |
| 2-61 | DMTr | NH₂ | NHBz | H |
| 2-62 | TMTr | NH₂ | OH | H |
| 2-63 | TMTr | NH₂ | OH | Me |
| 2-64 | TMTr | NH₂ | NHBz | H |
| 2-65 | TMS | NH₂ | OH | H |
| 2-66 | TMS | NH₂ | OH | Me |
| 2-67 | TMS | NH₂ | NHBz | H |
| 2-68 | TBDMS | NH₂ | OH | H |
| 2-69 | TBDMS | NH₂ | OH | Me |
| 2-70 | TBDMS | NH₂ | NHBz | H |
| 2-71 | TBDPS | NH₂ | OH | H |
| 2-72 | TBDPS | NH₂ | OH | Me |
| 2-73 | TBDPS | NH₂ | NHBz | H |
| 2-74 | TBDPS | (MMTr)NH | OH | H |
| 2-75 | TBDPS | (MMTr)NH | OH | Me |
| 2-76 | TBDPS | (MMTr)NH | NHBz | H |
| 2-77 | TBDPS | (MMTr)NH | NHBz | Me |
| 2-78 | H | (MMTr)NH | OH | H |
| 2-79 | H | (MMTr)NH | OH | Me |
| 2-80 | H | (MMTr)NH | NHBz | H |
| 2-81 | H | (MMTr)NH | NHBz | Me |
| 2-82 | P(OCH₂CH₂CN)-(N(iPr)₂) | (MMTr)NH | OH | H |
| 2-83 | P(OCH₂CH₂CN)-(N(iPr)₂) | (MMTr)NH | OH | Me |
| 2-84 | P(OCH₂CH₂CN)-(N(iPr)₂) | (MMTr)NH | NHBz | H |
| 2-85 | P(OCH₂CH₂CN)-(N(iPr)₂) | (MMTr)NH | NHBz | Me |
| 2-86 | P(OCH₃)-(N(iPr)₂) | (MMTr)NH | OH | H |
| 2-87 | P(OCH₃)-(N(iPr)₂) | (MMTr)NH | OH | Me |
| 2-88 | P(OCH₃)-(N(iPr)₂) | (MMTr)NH | NHBz | H |
| 2-89 | P(OCH₃)-(N(iPr)₂) | (MMTr)NH | NHBz | Me |
| 2-90 | TBDPS | (DMTr)NH | OH | H |
| 2-91 | TBDPS | (DMTr)NH | OH | Me |
| 2-92 | TBDPS | (DMTr)NH | NHBz | H |
| 2-93 | TBDPS | (DMTr)NH | NHBz | Me |
| 2-94 | H | (DMTr)NH | OH | H |
| 2-95 | H | (DMTr)NH | OH | Me |
| 2-96 | H | (DMTr)NH | NHBz | H |
| 2-97 | H | (DMTr)NH | NHBz | Me |
| 2-98 | P(OCH₂CH₂CN)-(N(iPr)₂) | (DMTr)NH | OH | H |
| 2-99 | P(OCH₂CH₂CN)-(N(iPr)₂) | (DMTr)NH | OH | Me |
| 2-100 | P(OCH₂CH₂CN)-(N(iPr)₂) | (DMTr)NH | NHBz | H |
| 2-101 | P(OCH₂CH₂CN)-(N(iPr)₂) | (DMTr)NH | NHBz | Me |

TABLE 2-continued

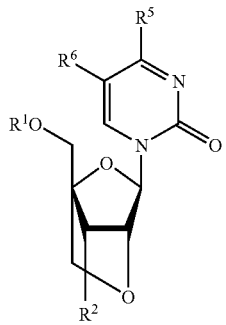

(1")

| Exemplification Compound number. | R¹ | R² | R⁵ | R⁶ |
|---|---|---|---|---|
| 2-102 | P(OCH₃)-(N(iPr)₂) | (DMTr)NH | OH | H |
| 2-103 | P(OCH₃)-(N(iPr)₂) | (DMTrDNH | OH | Me |
| 2-104 | P(OCH₃)-(N(iPr)₂) | (DMTr)NH | NHBz | H |
| 2-105 | P(OCH₃)-(N(iPr)₂) | (DMTr)NH | NHBz | Me |
| 2-106 | TBDPS | (Tfa)NH | OH | H |
| 2-107 | TBDPS | (Tfa)NH | OH | Me |
| 2-108 | TBDPS | (Tfa)NH | NHBz | H |
| 2-109 | TBDPS | (Tta)NH | NHBz | Me |
| 2-110 | H | (Tfa)NH | OH | H |
| 2-111 | H | (Tfa)NH | OH | Me |
| 2-112 | H | (Tfa)NH | NHBz | H |
| 2-113 | H | (Tfa)NH | NHBzMe | |
| 2-114 | P(OCH₂CH₂CN)-(N(iPr)₂) | (Tfa)NH | OH | H |
| 2-115 | P(OCH₂CH₂CN)-(N(iPr)₂) | (Tfa)NH | OH | Me |
| 2-116 | P(OCH₂CH₂CN)-(N(iPr)₂) | (Tfa)NH | NHBz | H |
| 2-117 | P(OCH₂CH₂CN)-(N(iPr)₂) | (Tfa)NH | NHBz | Me |
| 2-118 | P(OCH₃)-(N(iPr)₂) | (Tfa)NH | OH | H |
| 2-119 | P(OCH₃)-(N(iPr)₂) | (Tfa)NH | OH | Me |
| 2-120 | P(OCH₃)-(N(iPr)₂) | (Tfa)NH | NHBz | H |
| 2-121 | P(OCH₃)-(N(iPr)₂) | (Tfa)NH | NHBz | Me |
| 2-122 | TBDPS | (Cbz)NH | OH | H |
| 2-123 | TBDPS | (Cbz)NH | OH | Me |
| 2-124 | TBDPS | (Cbz)NH | NHBz | H |
| 2-125 | TBDPS | (Cbz)NH | NHBz | Me |
| 2-126 | H | (Cbz)NH | OH | H |
| 2-127 | H | (Cbz)NH | OH | Me |
| 2-128 | H | (Cbz)NH | NHBz | H |
| 2-129 | H | (Cbz)NH | NHBz | Me |
| 2-130 | P(OCH₂CH₂CN)-(N(iPr)₂) | (Cbz)NH | OH | H |
| 2-131 | P(OCH₂CH₂CN)-(N(iPr)₂) | (Cbz)NH | OH | Me |
| 2-132 | P(OCH₂CH₂CN)-(N(iPr)₂) | (Cbz)NH | NHBz | H |
| 2-133 | P(OCH₂CH₂CN)-(N(iPr)₂) | (Cbz)NH | NHBz | Me |
| 2-134 | P(OCH₃)-(N(iPr)₂) | (Cbz)NH | OH | H |
| 2-135 | P(OCH₃)-(N(iPr)₂) | (Cbz)NH | OH | Me |
| 2-136 | P(OCH₃)-(N(iPr)₂) | (Cbz)NH | NHBz | H |
| 2-137 | P(OCH₃)-(N(iPr)₂) | (Cbz)NH | NHBz | Me |

TABLE 2-continued

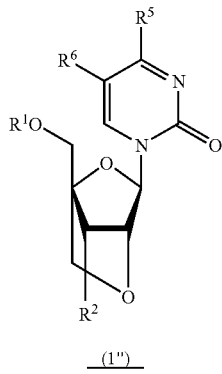

(1")

| Exemplification Compound number. | R$^1$ | R$^2$ | R$^5$ | R$^6$ |
|---|---|---|---|---|
| 2-138 | DMTr | NHP(OCH$_2$CH$_2$CN)-(N(iPr)$_2$) | OH | H |
| 2-139 | DMTr | NHP(OCH$_2$CH$_2$CN)-(N(iPr)$_2$) | OH | Me |
| 2-140 | DMTr | NHP(OCH$_2$CH$_2$CN)-(N(iPr)$_2$) | NHBz | H |
| 2-141 | DMTr | NHP(OCH$_2$CH$_2$CN)-(N(iPr)$_2$) | NHBz | Me |
| 2-142 | DMTr | NHP(OCH$_3$)-(N(iPr)$_2$) | OH | H |
| 2-143 | DMTr | NHP(OCH$_3$)-(N(iPr)$_2$) | OH | Me |
| 2-144 | DMTr | NHP(OCH$_3$)-(N(iPr)$_2$) | NHBz | H |
| 2-145 | DMTr | NHP(OCH$_3$)-(N(iPr)$_2$) | NHBz | Me |
| 2-146 | MMTr | NHP(OCH$_2$CH$_2$CN)-(N(iPr)$_2$) | OH | H |
| 2-147 | MMTr | NHP(OCH$_2$CH$_2$CN)-(N(iPr)$_2$) | OH | Me |
| 2-148 | MMTr | NHP(OCH$_2$CH$_2$CN)-(N(iPr)$_2$) | NHBz | H |
| 2-149 | MMTr | NHP(OCH$_2$CH$_2$CN)-(N(iPr)$_2$) | NHBz | Me |
| 2-150 | MMTr | NHP(OCH$_3$)-(N(iPr)$_2$) | OH | H |
| 2-151 | MMTr | NHP(OCH$_3$)-(N(iPr)$_2$) | OH | Me |
| 2-152 | MMTr | NHP(OCH$_3$)-(N(iPr)$_2$) | NHBz | H |
| 2-153 | MMTr | NHP(OCH$_3$)-(N(iPr)$_2$) | NHBz | Me |

Among the compounds listed in these Tables, preferred compounds are as follows (Exemplification compound numbers):

1-3, 1-4, 1-7, 1-9, 1-10, 1-16, 1-17, 1-19, 1-20, 1-21, 1-22, 1-23, 1-27, 1-28, 1 to 31, 1 to 33, 1 to 34, 1-40, 1-41, 1-43, 1-44, 1-45, 1-46, 1-47, 1-49, 1-50, 1-56, 1-57, 1-82, 1-83, 1-93, 1-94, 1-95, 1-96, 1-97, 1-98, 1-99, 2-3,2-4, 2-5,2-6, 2-7,2-8, 2-9,2-10, 2-13, 2-14, 2-15, 2-16, 2-17, 2-18, 2-19, 2-20, 2-21, 2-22, 2-48, 2-59, 2-60, 2-61, 2-74, 2-75, 2-76, 2-77, 2-78, 2-79, 2-80, 2-81, 2-82, 2-83, 2-84, 2-85, 2-86, 2-87, 2-88 and 2-89.

More preferred compounds are as follows (Exemplification compound numbers):

1-4, 1-22, 1-28, 1-46, 1-49, 1-50, 1-56, 1-57, 1-82, 1-83, 1-96, 1-97, 1-98, 1-99, 2-3,2-4, 2-6,2-13, 2-14, 2-16, 2-21, 2-22, 2-48, 2-59, 2-60, 2-61, 2-82, 2-83, 2-86, 2-87, 2-88 and 2-89.

Particularly preferred compounds are as follows (Exemplification compound numbers):

2-4: 3'-amino-3'-deoxy-2'-O,4'-C-methylene-5-methyluridine, 2-14: 3'-azido-3'-deoxy-2'-O,4'-C-methylene-5-methyluridine, 2-36: 3'-azido-3'-deoxy-5'-O-(4,4'-dimethoxytrityl)-2'-O,4'-C-methylene-5-methyluridine, 2-48: 3'-azido-5'-O-tert-butyldiphenylsilyl-3'-deoxy-2'-O,4'-C-methylene-5-methyluridine and 2-60: 3'-amino-3'-deoxy-5'-O-(4,4'-dimethoxytrityl)-2'-O,4'-C-methylene-5-methyluridine.

2-83: 3'-amino-3'-deoxy-N(4-monomethoxytrityl)-2'-O,4-C-methylene-5-methyluridine-5-O-(2-cyanoethyl-N, N-disopropyl)-phosphoramidite.

The compounds of the present invention can be synthesized in accordance with method A described below.

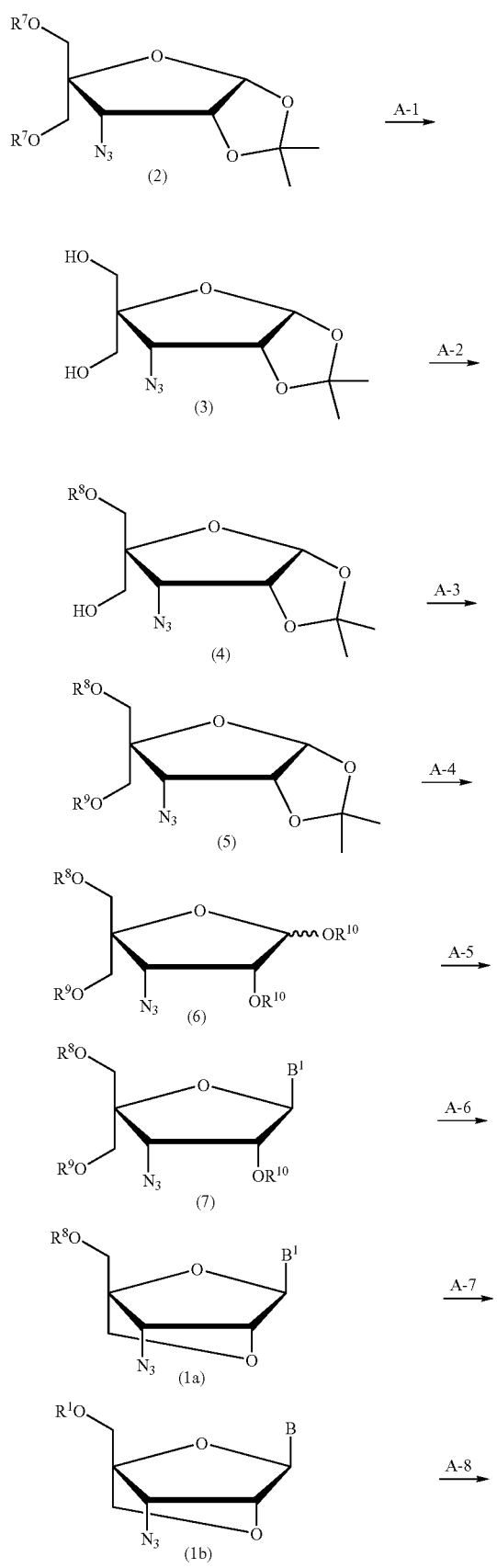

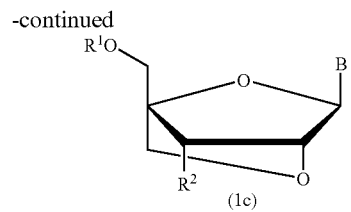

In the processes described above, $R^1$, $R^2$ and B are as defined previously.

$R^7$ represents a protecting group for a hydroxy group, and preferred groups are aromatic acyl groups, for example, aryl carbonyl groups such as benzoyl, α-naphthoyl, and β-naphthoyl; lower-alkylated-arylcarbonyl groups such as 2,4,6-trimethylbenzoyl, and 4-toluoyl, and arylated-arylcarbonyl groups such as 4-phenylbenzoyl. The most preferred group is a benzoyl group.

$R^8$ represents a protecting group for a hydroxy group and preferred groups are "silyl groups", for example, a tri-lower-alkylsilyl group such as trimethylsilyl, triethylsilyl, isopropyldimethylsilyl, t-butyldimethylsilyl, methyldiisopropylsilyl, methyldi-t-butylsilyl and triisopropylsilyl; and a tri-lower-alkylsilyl group substituted by 1–2 aryl groups such as diphenylmethylsilyl, t-butyldiphenylsilyl, diphenylisopropylsilyl and phenyldiisopropylsilyl; "a methyl group substituted by 1 to 3 aryl groups" such as benzyl, α-naphthylmethyl, β-naphthylmethyl, diphenylmethyl, triphenylmethyl, α-naphthyldiphenylmethyl and 9-anthrylmethyl; "a methyl group substituted by 1 to 3 aryl groups wherein the aryl ring is substituted by lower-alkyl, lower-alkoxy, a halogen atom or cyano group" such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 4,4',4"-trimethoxytriphenylmethyl, 2-nitorobenzyl, 4-nitrobenzyl, 4-chlorobenzyl, 4-bromobenzyl and 4-cyanobenzyl.

More preferred groups are a trimethylsilyl group, a t-butyldimethylsilyl group, a t-butyldiphenylsilyl group, a benzyl group, a triphenylmethyl group, a 4-methoxybenzyl group, a 4-methoxyphenyldiphenylmethyl group, a 4,4'-dimethoxytriphenylmethyl group or a 4,4',4"-trimethoxytriphenylmethyl group.

$R^9$ represents a leaving group and preferred groups are a lower-alkylsulfonyl group such as methanesulfonyl and ethanesulfonyl groups, a lower-alkylsulfonyl group substituted by halogen atoms such as trifluoromethanesulfonyl group, and an arylsulfonyl group such as p-toluenesulfonyl group.

Among these groups more preferred groups are methanesulfonyl group or p-toluenesulfonyl group.

$R^{10}$ represents a protecting group for a hydroxy group and preferred groups are "aliphatic acyl groups", for example, alkylcarbonyl groups such as formyl, acetyl, propionyl, butyryl, isobutyryl, pentanoyl, pivaloyl, valeryl, isovaleryl, octanoyl, decanoyl, 1-methylheptadecanoyl, nonadecanoyl, eicosanoyl and henicosanoyl, carboxylated alkylcarbonyl groups such as succinoyl, glutaroyl and adipoyl groups, halogeno-lower-alkylcarbonyl groups such as chloroacetyl, dichloroacetyl, trichloroacetyl and trifluoroacetyl groups, lower-alkoxy-lower-alkylcarbonyl groups such as a methoxyacetyl group, and unsaturated alkylcarbonyl groups such as a (E)-2-methyl-2-butenoyl group; "aromatic acyl groups", for example, arylcarbonyl groups such as benzoyl, α-naphthoyl and β-naphthoyl, halogenoarylcarbonyl groups such as 2-bromobenzoyl and 4-chlorobenzoyl groups, lower-alkylated arylcarbonyl groups such as 2,4,6-trimethylbenzoyl and 4-toluoyl groups, lower-alkoxylated arylcarbonyl groups such as 4-anisoyl group, carboxylated arylcarbonyl groups such as 2-carboxybenzoyl, 3-carboxybenzoyl and 4-carboxybenzoyl groups, nitrated arylcarbonyl groups such as 4-nitrobenzoyl and 2-nitrobenzoyl groups, lower-alkoxycarbonylated arylcarbonyl groups such as 2(methoxycarbonyl) benzoyl group, and arylated arylcarbonyl groups such as 4-phenylbenzoyl group.

Among these groups, more preferred groups are "aliphatic acyl groups" and a particularly preferred group is an acetyl group.

$B^1$ represents purine-9-yl or 2-oxo-1,2-dihydropyrimidin-1-yl group which may have 1 or more substituents selected from α1 group below.

α1 Group:
  a hydroxy group,
  a hydroxy group protected with a protecting group in nucleic acid synthesis,
  an alkoxy groups having 1–6 carbon atoms,
  a mercapto group,
  a mercapto group protected with a protecting group in nucleic acid synthesis,
  an alkylthio group having 1–6 carbon atoms,
  an amino group protected with a protecting group in nucleic acid synthesis,
  an amino groups substituted by an alkyl group having 1–6 carbon atoms,
  an alkyl group having 1–6 carbon atoms and halogen atoms.

Method A is a process to synthesize the compounds of formulae (1a), (1b) and (1c) from the starting compound (2) through introduction of a substitutent B and ring closure.

Here the starting compound (2) is synthesized from commercially available diacetone-D-glucose using a similar method to that described in the literature (O. T. Schmidt, Methods in Carbohydr. Chem., 4, 318 (1964); J. S. Brimacombe and O. A. Ching, Carbhyd. Res., 8, 82 (1968); T. F. Tam and B. Fraser-Reid, Can. J. Chem., 57, 2818 (1979); S. A. Suzhkov, Nucleosides & Nucleotides, 13, 2283 (1994)).

Details of each process of method A will be described below.

[Method A]

(Process A-1)

A compound (3) is prepared in this step, which comprises deprotection of a primary alcohol protecting group of starting compound (2) in the presence of a base in an inert solvent.

The solvent employed has no limitation, insofar as the solvent is one normally used for hydrolysis, and can be water; organic solvents, for example alcohols such as methanol, ethanol and n-propanol, and ethers such as tetrahydrofuran and dioxane; or a mixture of water and the organic solvents described above. Preferred solvents are alcohols.

The base employed has no limitation unless it affects other moieties of the compound. Preferred bases are metal alkoxides such as sodium methoxide; alkali metal carbonates such as sodium carbonate, potassium carbonate and lithium carbonate; alkali metal hydroxides such as sodium hydroxide, potassium hydroxide, lithium hydroxide and barium hydroxide, or ammonia such as aqueous ammonia solution and concentrated ammonia-methanol. Preferred bases are alkali metal carbonates.

The reaction temperature and reaction time depend upon the starting material, solvent and base employed and have no limitation. Ordinarily the reaction temperature is between 0° C. and 15° C. and the reaction time is from 1 hr to 10 hrs.

After termination of the reaction, the desired compound (3) is collected from the reaction mixture by conventional methods. For example, the reaction mixture is neutralized and concentrated, and to the residue is added water and an organic solvent immiscible with water, such as ethyl acetate. After washing with water, the organic phase including the desired compound is isolated, and dried over anhydrous sodium sulfate or the like. The desired compound is obtained by evaporation of the solvents.

The compound obtained is, if necessary, purified by conventional methods, such as recrystallization and/or silica gel column chromatography.

(Process A-2)

A compound (4) is prepared in this process which comprises reaction of compound (3) obtained in process A-1 with a hydroxy-protecting agent in the presence of a base in an inert solvent.

The solvent employed has no limitation, as far as it does not inhibit the reaction and dissolves the starting materials to some extent and is, for example, an aliphatic hydrocarbon such as hexane and heptane; an aromatic hydrocarbon such as benzene, toluene and xylene; a halogenated hydrocarbon such as methylene chloride, chloroform, carbon tetrachloride, dichloroethane, chlorobenzene and dichlorobenzene; an ester such as ethyl formate, ethyl acetate, propyl acetate, butyl acetate and diethyl carbonate; an ether such as diethyl ether, diisopropyl ether, tetrahydrofuran, dioxane, dimethoxyethane and diethylene glycol dimethyl ether; a nitrile such as acetonitrile and isobutyronitrile; an amide such as formamide, N,N-dimethylformamide, N,N-dimethylacetamide, N-methyl-2-pyrrolidone N-methyl-pyrrolidinone, and hexamethylphosphorotriamide. The preferred solvent is methylene chloride.

The base employed has no limitation, as far as it is used as abase in conventional reactions. For example, it can be an organic base such as N-methylmorpholine, triethylamine, tributylamine, diisopropylethylamine, dicyclohexylamine, N-methylpiperidine, pyridine, 4-pyrolidinopyridine, picoline, 4-(N,N-dimethylamino) pyridine, 2,6-di(tert-butyl)-4-methylpyridine, quinoline, N,N-dimethylaniline and N,N-diethylaniline. The preferred base is triethylamine.

The hydroxyl-protecting reagents employed are, for example, silyl halides such as t-butyldimethylsilyl chloride, trimethylsilyl chloride, triethylsilyl chloride, triethylsilyl bromide, triisopropylsilyl chloride, dimethylisopropylsilyl chloride, diethylisopropylsilyl chloride, t-butyldiphenylsilyl chloride, diphenylmethylsilyl chloride, and triphenylsilyl chloride; tritylhalides such as 4-methoxytriphenylmethyl chloride, 4,4'-dimethoxytriphenylmethyl chloride and 4,4', 4"-trimethoxytriphenylmethyl chloride; and aralkyl halides such as benzyl chloride, benzyl bromide and p-methoxybenzylbromide. The preferred hydroxyl-protecting reagent is t-butyldiphenylsilyl chloride.

The reaction temperature is usually between −20° C. and the reflux temperature of the solvent employed. The preferred temperature is between 0° C. and the reflux temperature of the solvent employed.

The reaction time depends upon mainly the reaction temperature, the starting compound, the base and the solvent employed. Ordinarily it is from 10 min to 3 days, and the preferred reaction time is from 1 hr to 24 hrs.

After the reaction is terminated, the desired compound (4) in the present reaction is collected from the reaction mixture, according to conventional methods. For example, the reaction mixture is neutralized, and water and an organic solvent immiscible with water, such as ethyl acetate, are added to the neutralized reaction mixture. After washing with water, the organic phase including the desired compound is separated, and dried over anhydrous sodium sulfate or the like. The desired compound is obtained by evaporation of the solvent.

The compound obtained is, if necessary, and particularly if a product in which $R^8$ is introduced to the hydroxy group at undesired positions is obtained, further purified by conventional methods, such as recrystallization and silica gel column chromatography.

(Process A-3)

A compound (5) is prepared in this process which comprises reaction of compound (4) obtained in process A-2 with a leaving-group introducing reagent in the presence of base in an inert solvent.

The solvent employed is, for example, an aliphatic hydrocarbon such as hexane, heptane, ligroin and petroleum ether; an aromatic hydrocarbon such as benzene, toluene and xylene; a halogenated hydrocarbon such as methylene chloride, chloroform, carbon tetrachloride, dichloroethane, chlorobenzene and dichlorobenzene; an ester such as ethyl formate, ethyl acetate, propyl acetate, butyl acetate and diethyl carbonate; an ether such as diethyl ether, diisopropyl ether, tetrahydrofuran, dioxane, dimethoxyethane, and diethylene glycol dimethyl ether; a ketone such as acetone, methyl ethyl ketone and methyl isobutyl ketone, isophorone, and cyclohexanone; a nitro compound such as nitroethane and nitrobenzene; a nitrile such as acetonitrile and isobutyronitrile; an amide such as formamide, N,N-dimethylformamide, N,N-dimethylacetamide, N-methyl-2-pyrrolidone, N-methylpyrrolidinone, and hexamethylphosphorotriamide; a sulfoxide such as sulfolane; or a pyridine.

Among these solvents, the preferred solvent is methylene chloride.

Preferred basic catalysts employed are bases such as triethylamine, pyridine and dimethylaminopyridine.

The leaving-group introducing reagent employed is, for example, an alkylsulfonyl halide such as methanesulfonyl chloride and ethanesulfonyl bromide; or an arylsulfonyl halide such as p-toluenesulfonyl chloride.

Preferred leaving-group introducing reagents are methanesulfonyl chloride and p-toluenesulfonyl chloride.

The reaction temperature depends upon the starting compound, solvent, leaving-group introducing reagent and base employed. Usually the temperature is between 0° C. and 50° C., and the preferred temperature is between 10° C. and 40° C.

The reaction time depends upon the starting compound, solvent, leaving-group introducing reagent and base employed. Usually the reaction time is from 10 min to 24 hrs, and the preferred reaction time is from 1 hr to 15 hrs.

After termination of the reaction, the desired compound (5) of this reaction is collected from the reaction mixture according to conventional methods. For example, the reaction mixture is neutralized and concentrated. Water and an organic solvent immiscible with water, such as ethyl acetate, are added to the residue. After washing with water, the organic phase including the desired compound is separated, dried over anhydrous sodium sulfate or the like, and then the desired compound can be obtained by evaporation of the solvents.

The compound obtained is, if necessary, purified by conventional methods, such as recrystallization, silica gel column chromatography and the like.

(Process A-4)

A compound (6) is prepared in this process which comprises reaction of compound (5) obtained in process A-3 with an acid anhydride in the presence of an acid catalyst in a solvent.

The solvent employed is, for example, an ether such as diethylether, dioxane and tetrahydrofuran; a nitrile such as acetonitrile and isobutyronitrile; an amide such as formamide, N,N-dimethylformamide, N,N-dimethyl-acetamide, N-methyl-2-pyrrolidone, N-methylpyrrolidinone and hexamethylphosphorotriamide; or an organic acid such as acetic acid. The preferred solvent is acetic acid.

The acid catalyst employed in process A-4 is, for example, an inorganic acid such as hydrochloric acid, sulfuric acid, or nitric acid. The preferred acid is sulfuric acid (particularly concentrated sulfuric acid).

The acid anhydride employed is, for example, a lower-aliphatic acid anhydride such as acetic acid anhydride, propionic acid an hydride and the like. The preferred acid anhydride is acetic anhydride.

The reaction temperature depends upon the starting compound, solvent, acid catalyst and acid anhydride employed. Usually the reaction temperature is between 0° C. and 50° C., and the preferred reaction temperature is between 10° C. and 40° C.

The reaction time depends upon the starting compound, solvent, acid catalyst, acid anhydride and the reaction temperature employed. Usually the reaction time is from 10 min to 12 hrs, and the preferred reaction time is from 30 min to 6 hrs.

After termination of the reaction, the desired compound (6) of this reaction is collected from the reaction mixture according to conventional methods. For example, water and an organic solvent immiscible with water, such as ethyl acetate, is added to the reaction mixture. After washing with water, the organic phase including the desired compound is isolated, dried over anhydrous sodium sulfate or the like, and then the desired compound can be obtained by evaporation of the solvent.

The compound obtained is, if necessary, further purified by conventional methods, such as recrystallization, silica gel column chromatography and the like.

(Process A-5)

A compound of (7) is prepared in this process which comprises reaction of compound (6) obtained in process A-4 with a trimethylsilyl derivative of an optionally substituted purine or pyrimidine, which is prepared in accordance with the literature (H. Vorbrueggen, K. Krolikiewicz and B. Bennua, Chem Ber., 114, 1234–1255 (1981)), in the presence of an acid catalyst in an inert solvent.

The solvent employed is an aromatic hydrocarbon such as benzene, toluene and xylene; a halogenated hydrocarbon such as methylene chloride, chloroform, carbon tetrachloride, 1,2-dichloroethane, chlorobenzene and dichlorobenzene; a nitrile such as acetonitrile and isobutyronitrile; an amide such as formamide, N,N-dimethylformamide, N,N-dimethylacetamide, N-methyl-2-pyrrolidone, N-methyl-pyrrolidinone and hexamethylphosphorotriamide; or carbon disulfide. The preferred solvent is 1,2-dichloroethane.

The acid catalyst employed is, for example, a Lewis acid catalyst such as $AlCl_3$, $SnCl_4$, $TiCl_4$, $ZnCl_2$, $BF_3$ and trimethylsilyl trifluoromethanesulfonate. The preferred acid catalyst is tin tetrachloride ($SnCl_4$).

The reaction temperature depends upon the starting compound, solvent and acid catalyst employed. Usually the reaction temperature is between 0° C. and 100° C., and the preferred reaction temperature is between 30° C. and 80° C.

The reaction time depends upon the starting compound, solvent, acid catalyst, and reaction temperature employed. Usually the reaction time is from 1 hr to 3 days, and the preferred reaction time is from 1 hr to 2 days.

After termination of the reaction, the desired compound (7) of this reaction is collected from the reaction mixture according to conventional methods. For example, the reaction mixture is neutralized, and water and an organic solvent immiscible with water, such as ethyl acetate or methylene chloride, is added to the resulting mixture. After washing with water, the organic phase including the desired compound is separated, dried over anhydrous sodium sulfate or the like, and then the desired compound can be obtained by evaporation of the solvent.

The compound obtained is, if necessary, purified by conventional methods, for example recrystallization, silica gel column chromatography, and the like.

(Process A-6)

A compound (1c) is prepared in this process which comprises a cyclization reaction of compound (7) obtained in process A-5 in the presence of a basic catalyst in an inert solvent.

The solvent employed has no limitation as far as it does not inhibit the reaction and it dissolves the starting compound to some extent. Preferred solvents are alcohols such as methanol, ethanol, n-propanol, isopropanol, n-butanol, isobutanol, t-butanol, isoamyl alcohol, diethylene glycol, glycerin, octanol, cyclohexanol and methyl cellosolve. The most preferred solvent is methanol.

The basic catalyst employed is, for example, an alkali metal hydroxide such as sodium hydroxide and potassium hydoxide; an alkali metal carbonate such as sodium carbonate and potassium carbonate; an alkali metal alkoxide such as sodium methoxide and sodium ethoxide; or aqueous ammonia solution and the like. Preferred basic catalysts are alkaline metal carbonates and the most preferred basic catalyst is sodium carbonate.

The reaction temperature depends upon the starting compound, solvent, and basic catalyst employed. Usually the reaction temperature is between 0° C. and 50° C., and the preferred reaction temperature is between 10° C. and 30° C.

The reaction time depends upon the starting compound, solvent, basic catalyst, and the reaction temperature employed. Usually the reaction time is from 1 hr to 3 days, and the preferred reaction time is from 3 hr to 2 days.

After termination of the reaction, the desired compound (1a) of this reaction is collected from the reaction mixture according to conventional methods. For example, the reaction mixture is concentrated, and water and an organic solvent immiscible with water, such as ethyl acetate, are added to the residue. After washing with water, the organic phase including the desired compound is separated, dried over anhydrous sodium sulfate or the like, and then the desired compound can be obtained by evaporation of the solvent.

The compound obtained is, if necessary, purified by conventional methods, for example recrystallization, silica gel column chromatography, and the like.

(Process A-7)

A compound (1b) is prepared in this process which comprises reaction of compound (1a) obtained in process A-6 with a deprotecting agent in an inert solvent. In the case that deprotection is unnecessary, the next process can be conducted without this process.

The process of deprotection depends upon the protecting groups employed, and the deprotecting reagent has no limitation unless it has an adverse effect on the reaction. For instance, the deprotection can be carried out according to methods described in the literature of "Protective Groups in Organic Synthesis" (Theodora W. Greene, 1981, A Wiley-Interscience Publication).

When different kinds of protecting groups exist, some of these methods are appropriately combined and each of these carried out in turn.

Particularly when the protecting groups are (1) "aliphatic acyl or aromatic acyl groups", (2) "a methyl group substituted by 1 to 3 aryl groups" or a "methyl groups substituted by 1 to 3 aryl rings wherein the aryl ring is substituted by lower-alkyl, lower-alkoxy, cyano group or halogen atom", (3) "silyl groups", the protecting groups can be deprotected with the following methods.

(1) When the protecting groups are aliphatic acyl or aromatic acyl groups, they are usually deprotected by reaction with bases in inert solvents.

The solvents employed have no limitation as far as they are usually used in hydrolysis. For instance, water; organic solvents, for example, alcohols such as methanol, ethanol, and n-propanol; ethers such as tetrahydrofuran and dioxane, or a mixture of water and above organic solvents are used. The preferred solvents are alcohols.

The bases employed have no limitation unless they affect other moieties of the compounds. Preferred bases are metal alkoxides such as sodium methoxide; alkali metal carbonates such as sodium carbonate, potassium carbonate and lithium carbonate; alkali metal hydroxides such as sodium hydroxide, potassium hydoxide, lithium hydroxide and barium hydroxide; or ammonia such as aqueous ammonia solutions and concentrated ammonium-ethanol. Preferred bases are alkali metal carbonates.

The reaction temperature and the reaction time depend upon the starting compound, solvent, base employed. Usually the reaction temperature is between 0° C. and 150° C. and the reaction time is from 1 hr. to 10 hrs. in order to suppress production of by-products.

After termination of the reaction, the desired compound (1b) of this reaction is collected from the reaction mixture according to conventional methods. For example, the reaction mixture is concentrated, and water and an organic solvent immiscible with water, such as ethyl acetate, are added to the residue. After washing with water, the organic phase including the desired compound is separated, dried over anhydrous sodium sulfate or the like, and then the desired compound can be obtained by evaporation of the solvent.

The compound obtained is, if necessary, purified by conventional methods, for example recrystallization, silica gel column chromatography and the like.

(2) In the case that the protecting group is "a methyl group substituted by 1 to 3 aryl groups" or "a methyl group substituted by 1 to 3 aryl groups wherein aryl ring is substituted by lower-alkyl, lower-alkoxy group, halogen atom or a cyano group", deprotection is carried out by a reducing reagent in an inert solvent.

Preferred solvents employed are alcohols such as methanol, ethanol and isopropanol; ethers such as diethyl ether, tetrahydrofuran and dioxane; aromatic hydrocarbons such as toluene, benzene and xylene; aliphatic hydrocarbons such as hexane and cyclohexane; esters such as ethyl acetate and propyl acetate; organic acids such as acetic acid; or mixtures of these organic solvents and water.

The reducing reagents employed have no limitation if they are usually used in catalytic reactions. Preferred reducing agents are palladium-carbon, Raney nickel, platinum oxide, platinum black, rhodium-aluminium oxide, triphenylphosphine-rhodium chloride and palladium-barium sulfate.

The reaction pressure has no limitation. Usually this process is performed under 1 to 10 atmosphere.

The reaction temperature is between 0° C. and 60° C., and the preferred reaction temperature is between 20° C. and 40° C.

The reaction time is from 10 min. to 24 hrs. and the preferred reaction time is from 1 to 3 hrs.

After termination of the reaction, the desired compound (1b) of this reaction is collected from the reaction mixture according to conventional methods. For example, the reducing reagent is removed, and water and an organic solvent immiscible with water, such as ethyl acetate, are added to the reaction mixture. After washing with water, the organic phase including the desired compound is separated, dried over anhydrous sodium sulfate or the like, and then the desired compound can be obtained by evaporation of the solvent.

The compound obtained is, if necessary, further purified by conventional methods, for example recrystallization, silica gel column chromatography and the like.

When the protecting group is "a methyl group substituted by 3 aryl groups", i.e., when the protecting group is a trityl group, deprotection can also be carried out using an acid.

In this case, the following solvents are used, for example, aromatic hydrocarbons such as benzene, toluene and xylene; halogenated hydrocarbons such as methylene chloride, chloroform, carbon tetrachloride, 1,2-dichloroethane, chlorobenzene and dichlorobenzene; alcohols such as methanol, ethanol, isopropanol and tert-butanol; nitriles such as acetonitrile and isobutyronitrile; amides such as formamide, N,N-dimethyl formamide, N,N-dimethylacetamide, N-methyl-2-pyrrolidone, N-methyl-pyrrolidinone, and hexamethylphosphorotriamide; and organic acids such as acetic acid. Preferred solvents are organic acids (particularly acetic acid) and alcohols (particularly tert-butanol).

The preferred acid to use is acetic acid or trifluoroacetic acid.

The reaction temperature is between 0° C. and 60° C., and the preferred reaction temperature is between 20° C. and 40° C.

The reaction time is from 10 min to 24 hrs and the preferred reaction time is from 1 to 3 hrs.

After termination of the reaction, the desired compound (1b) of this reaction is collected from the reaction mixture according to conventional methods. For example, the reaction mixture is neutralized, and water and an organic solvent immiscible with water, such as ethyl acetate, are added to the resulting mixture. After washing with water, the organic phase including the desired compound is separated, dried over anhydrous sodium sulfate or the like, and then the desired compound can be obtained by evaporation of the solvent.

The compound obtained is, if necessary, further purified by conventional methods, for example recrystallization, silica gel column chromatography and the like.

(3) In the case that the protecting group is "a silyl group", the protecting group is usually deprotected by treatment with compounds which produce fluorine anion, such as tetrabutylammonium fluoride, hydrofluoric acid, hydrofluoric acid-pyridine, and potassium fluoride, or organic acids such as acetic acid, methanesulfonic acid, para-toluenesulfonic acid, trifluoroacetic acid, and trifluoromethanesulfonic acid, or inorganic acids such as hydrochloric acid.

When the protecting group is deprotected with fluorine anion, the reaction is, in some cases, accelerated by addition of an organic acid such as formic acid, acetic acid or propionic acid.

The solvents used have no limitation as far as they do not inhibit the reaction and they dissolve the starting materials to some extent. However, preferred solvents are ethers such as diethyl ether, diisopropylether, tetrahydrofuran, dioxane, dimethoxyethane and diethylene glycol dimethyl ether; nitriles such as acetonitrile and isobutyronitrile; water; organic acids such as acetic acid, and mixtures of these solvents described above.

The reaction temperature is between 0° C. and 100° C., and the preferred reaction temperature is between 20° C. to 70° C.

The reaction time is from 5 min. to 48 hrs. and the preferred reaction time is from 1 to 24 hrs.

After termination of the reaction, the desired compound (1b) of this reaction is collected from the reaction mixture according to conventional methods. For example, the solvents are evaporated and then the compound is purified by silica gel column chromatography.

(Process A-8)

A compound (1c) is prepared in this process which comprises catalytic reduction of the azido group in compound (1b) obtained in process A-7 to an amino group in the presence of hydrogen and a catalyst in an inert solvent and, if necessary, protection of the amino group.

The solvents employed have no limitation as far as they do not have an adverse effect on this reaction. Preferred solvents are alcohols such as methanol, ethanol and isopropanol; ethers such as diethylether, tetrahydrofuran and dioxane; aromatic hydrocarbons such as toluene, benzene and xylene; aliphatic hydrocarbons such as hexane and cyclohexane; esters such as ethyl acetate and propyl acetate; amides such as formamide, dimethylformamide, dimethylacetamide, N-methyl-2-pyrrolidone and hexamethylphosphorotriamide; aliphatic acids such as formic acid and acetic acid; water; or mixtures of these solvents described above.

The catalysts employed have no limitation if they are usually used in catalytic reductions. Preferred catalysts are palladium on carbon, palladium black, Raney nickel, platinum oxide, platinum black, rhodium-aluminium oxide, triphenylphosphine-rhodium chloride, palladium-barium sulfate.

The reaction pressure has no limitation, but is usually between 1 and 10 atmospheres.

The reaction temperature and reaction time depends upon the starting compound, solvent, and catalyst employed. Usually the reaction temperature is between 0° C. and 100° C. (preferred reaction temperature is between 20° C. and 40° C.), and the reaction time is from 5 min. to 48 hrs. (preferred reaction time is from 30 min. to 10 hrs.).

After termination of the reaction, the desired compound (1c) of this reaction is collected from the reaction mixture according to conventional methods. For example, the desired compound can be obtained through removal of the catalysts by filtration and by evaporation of solvent from the filtrate.

If desired, the amino group can be protected in accordance with the methods described in the above literature (Protective Groups in Organic Synthesis).

A N3'-P5' type oligonucleotide analogue of this invention in which the nitrogen atom at 3' position and the oxygen atom at 5' position are combined through phosphoric acid can be prepared using compound (1d) of this invention according to method B described below.

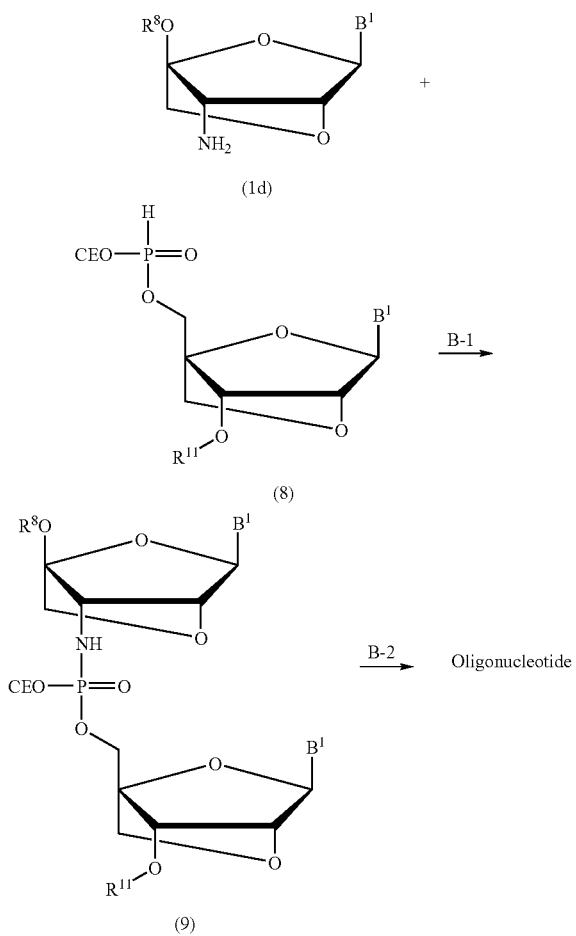

In the processes described above, $B^1$ and $R^8$ are as defined previously. However $B^1$ in the formula (1d) and $B^1$ in the formula (8) may be the same or different.

$R^{11}$ represents a resin such as succinyl Controlled Pore Glass or Tentagel, which is usually employed for the synthesis of oligonucleotides.

CEO represents a 2-cyanoethoxy group.

Each process of method B will be described below in detail.

(Process B-1)

A compound (9) is prepared in this process which comprises an oxidative phosphorylation coupling reaction of compound (1d) with compound (8). This process is performed as described in the literature (1) (Nucleic Acids Research, Vol. 23, No. 14, pp. 2661–2668, 1995).

The hydroxy group at the 5' position of the compound (1d) is protected in compound (1c) in Process A-8, and if an amino group exists in the base B, said amino group of compound (1d) is protected.

Further, the compound (8) can be prepared from the compound (1c) obtained in "Process A-8", in accordance with the literature (1).

(Process B-2)

This process is to produce an oligonucleotide from compound (9) obtained in the "Process B-1".

The process comprises deprotection of the hydroxyl-protecting group $R^8$ of compound (9) by a procedure of process A-7, phosphorylation in accordance with the literature (1), reaction with compound (1d) in a method similar to that described in the Process B-1, followed by repetition of these reactions to give the desired oligonucleotide.

The sequence length of the oligonucleotides obtained is usually 2–50 nucleoside units, and the preferred length is 10–30 nucleoside units.

The oligonucleotide analogues obtained are resistant to various nucleases. Thus they remain in the body for a long time after administration. Further, the oligonucleotide analogues, for instance, form stable double strands with mRNA, and inhibit biosynthesis of proteins which contribute to pathogenesis, or inhibit transcription to mRNA by forming triplets with the DNA double strands in genomes, or inhibit proliferation of viruses.

Thus the oligonucleotide analogues of the present invention can supress specified genome functions, and are expected to be therapeutic agents used for the treatment of diseases, such as anti-neoplasm agents, anti-viral agents, or the like.

The term "strand displacement" relates to a process whereby an oligonucleotide binds to its complementary target sequence in a double stranded or RNA so as to displace the other strand from said target strand Several diagnostic and molecular biology procedures have been developed that utilize panels of different oligonucleotides to simultaneously analyze a target nucleic acid for the presence of a plethora of possible mutations. Typically, the oligonucleotide panels are immobilized in a pre-determined pattern on a solid support such that the presence of a particular mutation in the target nucleic acid can be revealed by the position on the solid support where it hybridizes. One important prerequisite for the successful use of panels of different oligonucleotides in the analysis of nucleic acids is that they are all specific for their particular target sequence under the single applied hybridization condition. Since the affinity and specificity of standard oligonucleotides for their complementary target sequences depend heavily on their sequence and size this criteria has been difficult to fulfill so far.

In a preferred embodiment of the present invention, therefore, oligonucleotide analogues are used as a means to increase affinity and/or specificity of the probes and as a means to equalize the affinity of different oligonucleotides for their complementary sequences. As disclosed herein such affinity modulation can be accomplished by, e.g., replacing selected nucleosides in the oligonucleotide with a unit of formula (1a) carrying a similar nucleobase.

In another preferred embodiment of the present invention, the high affinity and specificity of oligonucleotide analogues is exploited in the sequence specific capture and purification of natural or synthetic nucleic acids. In one aspect, the natural or synthetic nucleic acids are contacted with oligonucleotide analogues immobilized on a solid surface. In this case hybridization and capture occurs simultaneously. The captured nucleic acids may be, for instance, detected, characterized, quantified or amplified directly on the surface by a variety of methods well known in the art or it may be released from the surface, before such characterization or amplification occurs, by subjecting the immobilized, modified oligonucleotide and captured nucleic acid to dehybridizing conditions, such as, for example, heat or by using buffers of low ionic strength.

The solid support may be chosen from a wide range of polymer materials such as, for instance, CPG (controlled pore glass), polypropylene, polystyrene, polycarbonate or polyethylene and it may take a variety of forms such as, for instance, a tube, a microtiter plate, a stick, a bead, a filter, etc. The oligonucleotide analogues may be immobilized to the solid support via its 5' or 3' end (or via the terminus of linkers attached to the 5' or 3' end) by a variety of chemical or photochemical methods usually employed in the immobilization of oligonucleotides or by non-covalent coupling such as for instance via binding of a biotinylated oligonucleotide analogues to immobilized streptavidin. One preferred method for immobilizing oligonucleotide analogues on different solid supports is a photochemical method using a photochemically active anthraquinone covalently attached to the 5' or 3' end of the oligonucleotide analogues (optionally via linkers) as described in WO 96/31557. Thus, the present invention also provides a surface carrying an oligonucleotide analogue.

In another aspect, the oligonucleotide analogue carries a ligand covalently attached to either the 5' or 3' end. In this case the oligonucleotide analogue is contacted with natural or synthetic nucleic acids in solution whereafter the hybrids formed are captured onto a solid support carrying molecules that can specifically bind the ligand.

In still another aspect, oligonucleotide analogues capable of performing "strand displacement" are used in the capture of natural and synthetic nucleic acids without prior denaturation. Such modified oligonucleotides are particularly useful in cases where the target sequence is difficult or impossible to access by normal oligonucleotides due to the rapid formation of stable intramolecular structures.

Examples of nucleic acids containing such structures are rRNA, tRNA, snRNA and scRNA.

In another preferred embodiment of the present invention, oligonucleotide analogues designed with the purpose of high specificity are used as primers in the sequencing of nucleic acids and as primers in any of the several well known amplification reactions, such as the PCR reaction. As shown herein, the design of the oligonucleotide analogues determines whether it will sustain a exponential or linear target amplification. The products of the amplification reaction can be analyzed by a variety of methods applicable to the analysis of amplification products generated with normal DNA primers. In the particular case where the oligonucleotide analogue primers are designed to sustain a linear amplification the resulting amplicons will carry single stranded ends that can be targeted by complementary probes without denaturation.

Such ends could for instance be used to capture amplicons by other complementary oligonucleotide analogues attached to a solid surface.

In another aspect, oligonucleotide analogues capable of "strand displacement" are used as primers in either linear or exponential amplification reactions. The use of such oligos is expected to enhance overall amplicon yields by effectively competing with amplicon re-hybridization in the later stages of the amplification reaction. Demers, et al. (*Nucl. Acid Res.*, 1995, Vol 23, 3050–3055) discloses the use of high-affinity, non-extendible oligos as a means of increasing the overall yield of a PCR reaction. It is believed that the oligomers elicit these effect by interfering with amplicon re-hybridization in the later stages of the PCR reaction. It is expected that oligonucleotide analogue blocked at their 3' end will provide the same advantage. Blocking of the 3' end can be achieved in numerous ways like for instance by exchanging the 3' hydroxyl group with hydrogen or phosphate. Such 3' blocked oligonucleotide analogues can also be used to selectively amplify closely related nucleic acid sequences in a way similar to that described by Yu et al. (*Biotechniques*, 1997, 23, 714–716).

In recent years, novel classes of probes that can be used in, for example, real-time detection of amplicons generated by target amplification reactions have been invented.

One such class of probes have been termed "Molecular Beacons". These probes are synthesized as partly self-complementary oligonucleotides containing a fluorophor at one end and a quencher molecule at the other end. When free in solution, the probe folds up into a hairpin structure (guided by the self-complimentary regions) which positions the quencher in sufficient closeness to the fluorophor to quench its fluorescent signal. Upon hybridization to its target nucleic acid, the hairpin opens thereby separating the fluorophor and quencher and giving off a fluorescent signal.

Another class of probes have been termed "Taqman probes". These probes also contain a fluorophor and a quencher molecule. Contrary to the "Molecular Beacons", however, the ability of the quenchers to quench the fluorescent signal from the fluorophor is maintained after hybridization of the probe to its target sequence. Instead, the fluorescent signal is generated after hybridization by physical detachment of either the quencher or the fluorophor from the probe by the action of the 5' exonuclease activity of a polymerase which has initiated synthesis from a primer located 5' to the binding site of the Taqman probe.

High affinity for the target site is an important feature in both types of probes and consequently such probes tends to be fairly large (typically 30 to 40 mers). As a result, significant problems are encountered in the production of high quality probes.

In a preferred embodiment, therefore, the oligonucleotide analogue is used to improve production and subsequent performance of "Taqman probes" and "Molecular Beacons" by reducing their size, whilst retaining the required affinity.

In a further aspect, the oligonucleotide analogues are used to construct new affinity pairs (either fully or partially modified oligonucleotides). The affinity constants can easily be adjusted over a wide range and a vast number of affinity pairs can be designed and synthesized.

One part of the affinity pair can be attached to the molecule of interest (e.g., proteins, amplicons, enzymes, polysaccharides, antibodies, haptens, peptides, PNA, etc.) by standard methods, while the other part of the affinity pair can be attached to e.g., a solid support such as beads, membranes, microtiter plates, sticks, tubes, etc. The solid support may be chosen from a wide range of polymer materials such as for instance polypropylene, polystyrene, polycarbonate or polyethylene. The affinity pairs may be used in selective isolation, purification, capture and detection of a diversity of the target molecules mentioned above.

The principle of capturing oligonucleotide analogue by ways of interaction with another complementary oligonucleotide analogue (either fully or partially modified) can be used to create an infinite number of novel affinity pairs.

In another preferred embodiment, the high affinity and specificity of the oligonucleotide analogues are exploited in the construction of probes useful in in-situ hybridization. For instance, an oligonucleotide analogue could be used to reduce the size of traditional DNA probes, whilst maintaining the required affinity thereby increasing the kinetics of the probe and its ability to penetrate the sample specimen. The ability of the oligonucleotide analogues to "strand displace" double stranded nucleic acid structures are also of considerable advantage in in-situ hybridization, because it facilitates hybridization without prior denaturation of the target DNA/RNA.

The present invention also provides a kit for the isolation, purification, amplification, detection, identification, quantification, or capture of natural or synthetic nucleic acids, wherein the kit comprises a reaction body and one or more oligonucleotide analogues as defined herein. The oligonucleotide analogues are preferably immobilized onto said reaction body (e.g., by using the immobilizing techniques described above).

For the kits according to the invention, the reaction body is preferably a solid support material, e.g., selected from borosilicate glass, soda-lime glass, polystyrene, polycarbonate, polypropylene, polyethylene, polyethyleneglycol terephthalate, polyvinyl acetate, polyvinylpyrrolidinone, polymethylmethacrylate and polyvinylchloride, preferably polystyrene and polycarbonate. The reaction body may be in the form of a specimen tube, a vial, a slide, a sheet, a film, a bead, a pellet, a disc, a plate, a ring, a rod, a net, a filter, a tray, a microtiter plate, a stick, or a multi-bladed stick.

The kits are typically accompanied by a written instruction sheet stating the optimal conditions for the use of the kit.

"Antigene activity" is the ability to inhibit gene expression by forming a triplex with a DNA duplex. "Antisense activity" is the ability to inhibit gene expression by forming a duplex with a sense sequence. A triplex with a DNA duplex means the state that an oligonucleotide fits into the groove of a DNA duplex strand, known as a "major groove".

The oligonucleotides of the present invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the present invention. Seemingly diverse organisms such as bacteria, yeast, protozoa, algae, all plants and all higher animal forms, including warm-blooded animals, including humans, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

Some representative therapeutic indications and other uses for the compounds of the invention are as follows:

One of the most significant health problems is the inadequate treatment of pain. The impact of pain places great burden in economic terms as well as in human suffering. Neuropathic pain is one of the most difficult pains to treat and cure. The primary site of this abnormal and ectopic site is the dorsal root ganglion (DRG) of the injured site. In the DRG, two main types of sodium currents, termed TTX-sensitive and TTX-resistant, have been identified. The blockage of the sodium channel PN3/SNS, which is TTX-resistant, is a candidate for pain relief. Antisense compounds targeted to PN3/SNS are described in Porreca et al. *Proc. Natl. Acad. Sci.* 1999, 96, 7640–7644.

Another therapeutic indication of particular interest with respect to the present invention is psoriasis. Psoriasis is a common chronic and recurrent disease characterized by dry, well-circumscribed, silvery, scaling papules and plaques of various sizes. The disease varies in severity from a few lesions to widespread dermatosis with disabling arthritis or exfoliation. The ultimate cause of psoriasis is presently not known, but the thick scaling that occurs is probably due to increased epidermal cell proliferation (*The Merck Manual of Diagnosis and Therapy*, 15th Ed., pp. 2283–2285, Berkow et al., eds., Rahway, N.J., 1987). Inhibitors of Protein Kinase C (PKC) have been shown to have both antiproliferative and anti-inflammatory effects in vitro. Some antipsoriasis drugs, such as cyclosporin A and anthralin, have been shown to inhibit PKC, and inhibition of PKC has been suggested as a therapeutic approach to the treatment of psoriasis (Hegemann, L. and G. Mahrle, *Pharmacology of the Skin*, H. Mukhtar, ed., pp. 357–368, CRC Press, Boca Raton, Fla., 1992). Antisense compounds targeted to Protein Kinase C (PKC) proteins are described in U.S. Pat. No. 5,620,963 to Cook et al. and U.S. Pat. No. 5,681,747 to Boggs et al.

A further therapeutic indication of interest to the present invention are inflammatory disorders of the skin. These occur in a variety of forms including, for example, lichen planus, toxic epidermal necrolyis (TEN), ertythema multiforme and the like (*The Merck Manual of Diagnosis and Therapy*, 15th Ed., pp. 2286–2292, Berkow et al., eds., Rahway, N.J., 1987). Expression of ICAM-1 has been associated with a variety of inflammatory skin disorders such as allergic contact dermatitis, fixed drug eruption, lichen planus and psoriasis (Ho et al., *J. Am. Acad. Dermatol.*, 1990, 22, 64; Griffiths et al., *Am. J. Pathology*, 1989, 135, 1045; Lisby et al., *Br. J. Dermatol.*, 1989, 120, 479; Shiohara et al., *Arch. Dermatol.*, 1989, 125, 1371; Regezi et al., Oral Surg. Oral Med. Oral Pathol., 1996, 81, 682). Moreover, intraperitoneal administration of a monoclonal antibody to ICAM-1 decreases ovalbumin-induced eosinophil infiltration into skin in mice (Hakugawa et al., J. Dermatol., 1997, 24, 73). Antisense compounds targeted to ICAM-1 are described in U.S. Pat. Nos. 5,514,788, 5,591, 623 and 6,111,094.

Other antisense targets for skin inflammatory disorders are VCAM-1 and PECAM-1. Intraperitoneal administration of a monoclonal antibody to VCAM-1 decreases ovalbumin-induced eosinophil infiltration into the skin of mice (Hakugawa et al., *J. Dermatol.*, 1997, 24, 73). Antisense compounds targeted to VCAM-1 are described in U.S. Pat. Nos. 5,514,788 and 5,591,623. PECAM-1 proteins are glycoproteins which are expressed on the surfaces of a variety of cell types (for reviews, see Newman, *J. Clin. Invest.*, 1997, 99, 3 and DeLisser et al., *Immunol. Today*, 1994, 15, 490). In addition to directly participating in cell-cell interactions, PECAM-1 apparently also regulates the activity and/or expression of other molecules involved in cellular interactions (Litwin et al., *J. Cell Biol.*, 1997, 139, 219) and is thus a key mediator of several cell: cell interactions. Antisense compounds targeted to PECAM-1 are described in U.S. Pat. No. 5,955,443.

Another type of therapeutic indication of interest for using oligonucleotides of the present invention encompasses a variety of cancers of the skin. Representative skin cancers include benign tumors (warts, moles and the like) and malignant tumors such as, for example, basal cell carcinoma, squamous cell carcinoma, malignant melanoma, Paget's disease, Kaposi's sarcoma and the like (*The Merck Manual of Diagnosis and Therapy*, 15th Ed., pp. 2301–2310, Berkow et al., eds., Rahway, N.J., 1987). A number of molecular targets involved in tumorigenesis, maintenance of the hyperproliferative state and metastasis are targeted to prevent or inhibit skin cancers, or to prevent their spread to other tissues.

The ras oncogenes are guanine-binding proteins that have been implicated in cancer by, e.g., the fact that activated ras oncogenes have been found in about 30% of human tumors generally; this figure approached 100% in carcinomas of the exocrine pancreas (for a review, see Downward, *Trends in Biol. Sci.*, 1990, 15, 469). Antisense compounds targeted to H-ras and K-ras are described in U.S. Pat. No. 5,582,972 to Lima et al., U.S. Pat. No. 5,582,986 to Monia et al. and U.S. Pat. No. 5,661,134 to Cook et al., and in published PCT application WO 94/08003.

Protein Kinase C (PKC) proteins have also been implicated in tumorigenesis. Antisense compounds targeted to Protein Kinase C (PKC) proteins are described in U.S. Pat. No. 5,620,963 to Cook et al. and U.S. Pat. No. 5,681,747 to Boggs et al. Also of interest are AP-1 subunits and JNK proteins, particularly in regard to their roles in tumorigenesis and metastasis. The process of metastasis involves a sequence of events wherein (1) a cancer cell detaches from its extracellular matrices, (2) the detached cancer cell migrates to another portion of an animal's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, *Sci. Amer.*, 1996, 275, 72). However, many human tumors have elevated levels of activity of one or more matrix metalloproteinases (MMPs) (Stetler-Stevenson et al., *Annu. Rev. Cell Biol.*, 1993, 9, 541; Bernhard et al., *Proc. Natl. Acad. Sci.* (U.S.A.), 1994, 91, 4293. The MMPs are a family of enzymes which have the ability to degrade components of the extracellular matrix (Birkedal-Hansen, *Current Op. Biol.*, 1995, 7, 728). In particular, one member of this family, matrix metalloproteinase-9 (MMP-9), is often found to be expressed only in tumors and other diseased tissues (Himelstein et al., *Invasion & Metastasis*, 1994, 14, 246).

Several studies have shown that regulation of the MMP-9 gene may be controlled by the AP-1 transcription factor (Kerr et al., *Science*, 1988, 242, 1242; Kerr et al., *Cell*, 1990, 61, 267; Gum et al., *J. Biol. Chem.*, 1996, 271, 10672; Hua et al., *Cancer Res.*, 1996, 56, 5279). Inhibition of AP-1 function has been shown to attenuate MMP-9 expression (U.S. Pat. No. 5,985,558). AP-1 is a heterodimeric protein having two subunits, the gene products of fos and jun. Antisense compounds targeted to c-fos and c-jun are described in U.S. Pat. No. 5,985,558.

Furthermore, AP-1 is itself activated in certain circumstances by phosphorylation of the Jun subunit at an amino-terminal position by Jun N-terminal kinases (JNKs). Thus, inhibition of one or more JNKs is expected to result in decreased AP-1 activity and, consequentially, reduced MMP expression. Antisense compounds targeted to JNKs are described in U.S. Pat. No. 5,877,309.

Infectious diseases of the skin are caused by viral, bacterial or fungal agents. In the case of Lyme disease, the tick borne causative agent thereof, the spirochete Borreliaburgdorferi, up-regulates the expression of ICAM-1, VCAM-1 and ELAM-1 on endothelial cells in vitro (Boggemeyer et al., *Cell Adhes. Comm.*, 1994, 2, 145). Furthermore, it has been proposed that the mediation of the disease by the anti-inflammatory agent prednisolone is due in part to mediation of this up-regulation of adhesion molecules (Hurtenbach et al., Int. *J. Immunopharmac.*, 1996, 18, 281). Thus, potential targets for therapeutic mediation (or prevention) of Lyme disease include ICAM-1, VCAM-1 and ELAM-1 (supra).

Other infectious disease of the skin which are tractable to treatment using the compositions and methods of the invention include disorders resulting from infection by bacterial, viral or fungal agents (*The Merck Manual of Diagnosis and Therapy*, 15th Ed., pp. 2263–2277, Berkow et al., eds., Rahway, N.J., 1987).

With regard to infections of the skin caused by fungal agents, U.S. Pat. No. 5,691,461 describes antisense compounds for inhibiting the growth of *Candida albicans*.

With regard to infections of the skin caused by viral agents, U.S. Pat. Nos. 5,166,195, 5,523,389 and 5,591,600 concern oligonucleotide inhibitors of Human Immunodeficiency Virus (HIV) U.S. Pat. No. 5,004,810 is directed to oligomers capable of hybridizing to herpes simplex virus Vmw65 mRNA and inhibiting its replication. U.S. Pat. Nos. 5,194,428 and 5,580,767 disclose antisense compounds having antiviral activity against influenza virus. U.S. Pat. No. 4,806,463 relates to antisense compounds and methods using them to inhibit HTLV-III replication. U.S. Pat. Nos. 4,689,320, 5,442,049, 5,591,720 and 5,607,923 are directed to antisense compounds as antiviral agents specific to cytomegalovirus (CMV). U.S. Pat. No. 5,242,906 describes antisense compounds useful in the treatment of latent Epstein-Barr virus (EBV) infections. U.S. Pat. Nos. 5,248,670, 5,514,577 and 5,658,891 provide antisense compounds useful in the treatment of herpes virus infections. U.S. Pat. Nos. 5,457,189 and 5,681,944 disclose antisense compounds useful in the treatment of papilloma virus infections. The antisense compounds disclosed in the aforesaid U.S. patents, all of which U.S. patents are herein incorporated by reference, may be used with (or replaced by) the compositions of the present invention to effect prophylactic, palliative or therapeutic relief from diseases caused or exacerbated by the indicated pathogenic agents.

Antisense oligonucleotides of the present invention may also be used to determine the nature, function and potential relationship of various genetic components of the body to disease or body states in animals. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development, since the "knock-out" mutation would produce a lethal phenotype. Moreover, the loss-of-function phenotype cannot be transiently introduced during a particular part of the animal's life cycle or disease state; the "knock-out" mutation is always present. "Antisense knockouts," that is, the selective modulation of expression of a gene by antisense oligonucleotides, rather than by direct genetic manipulation, overcomes these limitations (see, for example, Albert et al., *Trends in Pharmacological Sciences,* 1994, 15, 250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. Antisense oligonucleotides have been systemically administered to rats in order to study the role of the N-methyl-D-aspartate receptor in neuronal death, to mice in order to investigate the biological role of protein kinase C-a, and to rats in order to examine the role of the neuropeptide Y1 receptor in anxiety (Wahlestedt et al., *Nature,* 1993, 363:260; Dean et al., *Proc. Natl. Acad. Sci. U.S.A.,* 1994, 91:11762; and Wahlestedt et al., *Science,* 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.,* 1994, 15:250). By providing compositions and methods for the simple nonparenteral delivery of oligonucleotides and other nucleic acids, the present invention overcomes these and other shortcomings.

With the growing insight of the potential biological role of triple helical nucleic acids and the therapeutic potential of oligonucleotide-directed triplex formation in the control of gene expression according to the antigene strategy, research in triple helical structures has been considerably stimulated. Thus, in the antigene approach, oligonucleotides are targeted to the unique gene that specifies a disease-related protein and stall transcription by binding to the major groove of the double stranded DNA target. Articles which contain a good review of this are Thuong & Mine in *Angew. Chem. Int. Ed. Engl.* 1993 32, pages 666–690 and "Prospects for the Therapeutic Use of Antigene Oligonucleotides", Maher, L. J. (1996) *Cancer Investigation* 14(1), 66–82 each of which are hereby incorporated by reference in their entirety.

A review of the development of the antigene strategies for designing drugs that will bind to selected sites on the nucleic acids (DNA and RNA) is found in an article by J. S. Cohen and M. E. Hogan in *Scientific American,* December 1994, pages 50–55 and in the monograph by Soyfer, V. N. & Potaman, V N. (1996). "Triple-helical nucleic acids", Springer-Verlag, New York.

One of the diseases of interest as an antigene therapeutical target is cancer. The type I insulin-like growth factor receptor (IGF-IR) plays an important role in the maintenance of the malignant phenotype of cancer (Rubin, R. & Baeserga, R. *Lab. Invest.* 73, 311(1995)). A large number of cancers and cancer-derived cell lines overexpress the IGF-IR (Le-Roith, D et al, *Endocr. Rev.* 16, 143(1995)). Antisense expression vectors directed against the IGF-IR have proven effective in suppressing tumor growth of C6 rat glioblastoma (Baeserga, R. et al, *Cancer Res.* 54, 2218(1994)), hamster mesothelioma (Resnicoff, M. et al, *Cancer Immunol. Immunother.* 42, 64(1996)), and rat prostate cancer (Pass, H. et al, *Cancer Res.* 56, 4044(1996)). An antigene molecule expressed in rat C6 glioblastoma cells inhibited IGF-I transcription and tumorigenic potential of the cell (Rininsland, F. et al, *Proc. Natl. Acad. Sci. USA* 94, 5854(1997)). A compound inhibiting the expression of IGF-IR by means of antigene activity would be a medicament for the above described types of cancer.

Antigene drugs can be used to treat the following diseases:
Anti-Virus
  HIV (Giovannangeli, C. et al., *Proc. Natl. Acad. Sci. USA,* (1992) 89, 8631–8635)
Anti-Cancer
  human multidrug-resistance mdrl gene
    (Morassutti, C. et al., *Antisense Nucleic Acid Drug Dev,* (1999) 9, 261–270)
  human HER-2/neu gene
    (Ebbinghaus, S. W. et al., *Biochemistry,* (1999) 38, 619–628)
  human c-myc gene
    (Catapano, C. V. et al., *Biochemistry,* (2000) 39, 5126–5138)

Non-oral formulations or liposome formulations of the oligonucleotide analogues of this invention can be prepared, for instance, by addition of conventional adjuvants such as buffers and/or stabilizers. The nucleotide analogues may be blended with conventional pharmaceutical carriers to prepare ointments, creams, liquids or plasters.

Dosage forms of the oligonucleotide analogue having one, or two or more structures of the formula (1a) of the present invention may be tablets, capsules, granules, powders or syrup for oral administration, or injections or suppositories for parenteral administration. These dosage forms are prepared by well-known methods using carriers such as excipients (for example, organic excipients such as sugar derivatives, e.g. lactose, sucrose, glucose, mannitol and sorbitol; starch derivatives, e.g. corn starch, potato starch, α-starch and dextrin; cellulose derivatives, e.g. crystalline cellulose; gum arabic; dextran; and Pullulan; and inorganic excipients such as silicate derivatives, e.g. light silicic anhydride, synthesized aluminium silicate, calcium silicate and magnesium aluminate meta silicate; phosphates, e.g. calcium hydrogen phosphate; carbonates, e.g. calcium carbonate; and sulfates, e.g. calcium sulfate), lubricants (for example, stearic acid, stearic acid metal salts such as calcium stearate and magnesium stearate; talc; colloidal silica; waxes such as bee gum and spermaceti; boric acid; adipic acid; sulfates, e.g. sodium sulfate; glycol; fumaric acid; sodium benzoate; DL-leucine; fatty acid sodium salt; laurylsulfates such as sodium laurylsulfate and magnesium laurylsulfate; silicic acids such as silicic anhydride and silicic acid hydrate; and the above starch derivatives), binders (for example, hydroxypropyl cellulose, hydroxypropyl methyl cellulose, polyvinyl pyrrolidone, Macrogol and compounds similar to the above excipients), disintegrants (for example, cellulose derivatives, such as low-substituted hydroxypropyl cellulose, carboxymethyl cellulose, calcium carboxymethyl cellulose and internally bridged sodium carboxymethyl cellulose; and chemically modified starch-celluloses such as carboxymethyl starch, sodium carboxymethyl starch and bridged polyvinylpyrrolidone), stabilizers (paraoxybenzoates such as methylparaben and propylparaben; alcohols such as chlorobutanol, benzyl alcohol and phenylethyl alcohol; benzalkonium chloride; phenol derivatives such as phenol and cresol; thimerosal; dehydroacetic acid; and sorbic acid), corrigents (for example, sweeteners, souring agents, flavors, etc. usually used), diluents, etc.

More particularly, pharmaceutical compositions containing the active ingredient of the present invention may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the present invention may be in the form of a sterile injectable preparation, such as a sterile injectable aqueous or oleaginous suspension. This suspension may be formulated according to known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Formulations suitable for administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Their doses are different according to the symptoms of the disease, the age of the patient, such as a human patient and the route of administration. For instance, the lowest dose of the oligonucleotide analogue is 0.001 mg/kg of the body weight (preferably 0.01 mg/kg of the body weight), and the highest dose is 100 mg/kg of the body weight (preferably 10 mg/kg of the body weight) as a single dose. It is desirable to administer the oligonucleotide analogue from one to several times throughout the day depending on the symptoms of the patient.

The present invention will be described below in more detail by way of the following Examples and Reference examples. However, the present invention is not limited to those examples.

BEST MODE FOR CARRYING OUT THE INVENTION

EXAMPLE 1

3'-Azido-5'O-tert-butyldiphenylsilyl-3'-deoxy-2'-0, 4'-C-methyl ene-5-methyluridine Exemplification Compound Number 2–48

Potassium carbonate (41 mg, 0.29 mmol) was added to a methanol solution (7 ml) of the compound obtained in Reference example 5 (200 mg, 0.27 mmol) at 0° C. and the mixture was stirred for 4.5 hrs at room temperature. Further potassium carbonate (34 mg, 0.25 mmol) was added to the mixture, which was stirred for 23 hrs. After the methanol was evaporated, the residue was partitioned between ethyl acetate and water. The extract was washed with saturated aqueous sodium chloride solution. The organic phase was dried over anhydrous sodium sulfate. The solvents were evaporated and the residue was purified by silica gel column chromatography (ethyl acetate:n-hexane=2:1) to give the title compound as colorless crystals (142 mg, 0.27 mmol, 100%).

mp 93–95° C. IR vmax (KBr): 3169, 3047, 2956, 2888, 2859, 2117, 1696, 1275, 1109 $^1$H-NMR (CDCl$_3$) δ: 1.12 (9H, s), 1.65 (3H, s), 3.78, 3.84 (2H, AB, J=8 Hz), 3.90, 4.08 (2H, AB, J=12.5 Hz), 4.02 (1H, s), 4.67 (1H, s), 5.67 (1H, s), 7.54 (1H, s), 7.39–7.48 (6H, m), 7.67–7.71 (4H, m), 8.46 (1H, br s). $^{13}$C-NMR (CDCl$_3$) δ: 12.3, 19.5, 27.0, 58.7, 60.3, 71.4, 77.2, 78.6, 87.2, 90.1, 110.8, 128.0, 130.1, 130.2, 131.7, 132.3, 133.7, 135.1, 135.4, 149.6, 163.6.

EXAMPLE 2

3'-Azido-3'-deoxy-2'-O,4'-C-methylene-5-methyluridine

Exemplification Compound Number 2–14

Anhydrous tetrabutylammonium fluoride (10 M in THF, 290 μl, 0.29 mmol) was added to an anhydrous tetrahydrofuran solution (5 ml) of the compound obtained in Example 1 (140 mg, 0.26 mmol) in a stream of nitrogen gas and the solution was stirred for 1 hr at room temperature. The solvent was evaporated and the residue was purified by silica gel column chromatography (ethyl acetate:n-hexane=25:1) and the title compound was obtained as a white powder (65.7 mg, 0.22 mmol, 85%).

mp 94–96° C.

IR vmax (KBr): 3163, 3046, 2118, 1692, 1468, 1273, 1062 cm$^{-1}$. $^1$H-NMR (CD$_3$OD) δ: 1.89 (3H, s), 3.76, 3.86 (2H, AB, J=8 Hz), 3.85, 3.95 (2H, AB, J=13 Hz), 4.03 (1H, s), 4.58 (1H, s), 5.58 (1H, s), 7.70 (1H, s). $^{13}$C-NMR (CD$_3$OD) δ: 12.8, 57.3, 61.2, 72.4, 79.8, 88.3, 91.0, 110.8, 136.3, 151.5, 166.1.

EXAMPLE 3

3'-Amino-3'-deoxy-2'-0,4'-C-methylene-5-methyluridine

Exemplification Compound Number 2–4

An ethanol solution (3 ml) of the compound obtained in Example 2 (64 mg, 0.22 mmol) was added to 10% palladium-carbon (28 mg) suspended in anhydrous tetrahydrofuran solution (5 ml) in a stream of hydrogen gas, and the mixture was stirred for 0.5 hr at room temperature. The reaction mixture was filtered and the solvent of the filtrate was evaporated and the title compound was obtained as a white powder (59 mg, 0.22 mmol, 100%).

mp 243–246° C. IR vmax (KBr): 3459, 3365, 1699, 1447, 1273, 1054 cm$^{-1}$. $^1$H-NMR (C$_5$D$_5$N) δ: 1.83 (3H, s), 3.62 (1H, s), 3.92, 4.14 (2H, AB, J=8 Hz), 4.24 (2H, s), 4.54 (1H, s), 5.97 (1H, s), 7.90 (1H, s). $^{13}$C-NMR (C$_5$D$_5$N) δ: 12.8, 54.2, 57.2, 71.6, 81.4, 91.1, 109.5, 150.8, 164.3.

EXAMPLE 4

3'-Azido-3'-deoxy-5'-0-(4,4'-dimethoxytrityl)-2'-0,4'-C-methyl ene-5-methyluridine Exemplification Compound Number 2–36

Dimethoxytritylchloride (415 mg, 1.22 mmol) and dimethylaminopyridine (12.5 mg, 0.10 mmol) was added to a pyridine solution (6 ml) of the compound obtained in Example 2 (300 mg, 1.02 mmol) in a stream of nitrogen gas and the solution was stirred for 20.5 hr at room temperature. Saturated aqueous sodium hydrogen carbonate solution was added to the reaction mixture and the resulting mixture was extracted with dichloromethane. The organic phase was washed with water and saturated aqueous sodium chloride solution, and dried over anhydrous sodium sulfate. The solvent was evaporated under reduced pressure and the residue was purified by silica gel column chromatography (n-hexane:ethyl acetate=2:1→1:1) and the title compound was obtained as a pale yellow foam (462 mg, 0.78 mmol, 76%).

mp 125–128° C. $^1$H-NMR (CDCl$_3$) δ: 1.66 (3H, s), 3.32, 3.65 (2H, ABq, J=11 Hz), 3.78 (2H, s), 3.80 (6H, s), 4.13 (1H, s), 4.63 (1H, s), 5.67 (1H, s), 6.86 (4H, dd, J=2 Hz, 9 Hz), 7.23–7.45 (9H, m), 7.73 (1H, s), 8.04 (1H, brs).

EXAMPLE 5

3'-Amino-3'-deoxy-5'-0-(4,4'-dimethoxytrityl)-2'-0, 4'-C-methyl ene-5-methyluridine Exemplification Compound Number 2–60

Triphenylphosphine (94.0 ml, 0.36 mmol) was added to a pyridine solution (2.5 ml) of the compound obtained in Example 4 (110 mg, 0.18 mmol) in a stream of nitrogen and the mixture was stirred for 3.5 hr at room temperature. 28% solution of aqueous ammonia (5.5 ml) was added to the reaction mixture which was stirred for 24 hrs at room temperature. The solvent was evaporated under reduced pressure and the crude product was purified by silica gel column chromatography (chloroform: ethanol=20:1) and the title compound was obtained as a pale yellow foam (462 mg, 0.78 mmol, 76%).

mp 131–134° C. $^1$H-NMR (Pyridine-d$_5$) δ: 1.89 (3H, s), 3.71 (6H, s), 3.77 (1H, s), 3.84 (2H, s), 3.99, 4.10 (2H, ABq, J=8 Hz), 4.69 (1H, s), 6.04 (1H, s), 7.03–7.87 (13H, m), 8.58 (1H, s)

EXAMPLE 6

3'-Amino-3'-deoxy-5'-0-(4,4'-dimethoxytrityl)-2'-0, 4'-C-methyl ene-5-methyluridinyl-(3'→5')-3'-O-(tert-butyldimethylsilyl)thymidine 2-cyanoethyl ester A carbon tetrachloride solution (0.3 ml) of the compound obtained in Example 5 (10.0 mg, 18 µmol), and a solution of triethylamine (0.05 ml, 0.36 mmol) in acetonitrile (0.2 ml), were added to an acetonitrile solution (0.3 ml) of the compound obtained in Reference Example 6 (14.5 mg, 0.28 µmol) in a stream of nitrogen gas, and the solution was stirred for 14.5 hr at room temperature. The solvent was evaporated under reduced pressure and the crude product was purified by silica gel column chromatography (n-hexane:ethyl acetate=1:1→0:1) and the title compound was obtained as a white powder (13.0 mg, 12.5 µmol, 71%).

mp 101–105° C. $^{31}$P-NMR (CDCl$_3$) δ: 7.68, 8.24. Mass (FAB): m/z 1043(M$^+$+H).

EXAMPLE 7

3'-Amino-3'-deoxy-5'-0-(4,4'-dimethoxytrityl)-2'-0, 4'-C-methyl ene-5-methyluridinyl-(3'→5')-3'-O—-(tert-butyldimethylsilyl)thymidine methyl ester A carbon tetrachloride solution (0.3 ml) of the compound obtained in Example 5 (10.0 mg, 18 µmol), and a solution of triethylamine (0.05 ml, 0.36 mmol) in acetonitrile (0.2 ml), were added to an acetonitrile solution (0.3 ml) of the compound obtained in Reference Example 7 (22.1 mg, 51 µmol) in a stream of nitrogen gas, and the solution was stirred for 18 hrs at room temperature. Water was added to the reaction mixture and the resulting mixture was extracted with ethyl acetate. The organic phase was washed with saturated aqueous sodium chloride solution and dried over anhydrous sodium sulfate. The solvent was evaporated and the crude product was purified by silica gel column chromatography (dichloromethane: methanol=20:1, 30:1) and the title compound was obtained as a white powder (6.9 mg, 6.87 µmol, 39%).

mp 118–122° C. $^{31}$P-NMR (CDCl$_3$) δ: 11.20, 11.30. Mass (FAB): m/z 1026(M$^+$+Na)

EXAMPLE 8

3'-Amino-3'-deoxy-5'-0-(4,4'-dimethoxytrityl)-2'-0, 4'-C-methyl ene-5-methyluridinyl-(3'→5')-thymidine Methyl ester A tetrahydrofuran solution of tetrabutylammonium fluoride (1.0 M, 15 µl, 15 µmol) was added to tetrahydrofuran solution (1 ml) of the compound obtained in Example 7 (13.9 mg, 14 µmol) in a stream of nitrogen gas, and the solution was stirred for 3 hrs at room temperature. The solvent was evaporated under reduced pressure and the crude product was purified by silica gel column chromatography (ethyl acetate:ethanol=5:1) and the title compound was obtained as a colorless powder (9.7 mg, 10.9 µmol, 78%).

mp 157–160° C. $^{31}$P-NMR (CDCl$_3$) δ: 11.20, 11.30. Mass (FAB): m/z 1026(M$^+$+Na)

EXAMPLE 9

3'-Amino-3'-deoxy-5'-0-(4,4'-dimethoxytrityl)-2'-0, 4'-C-methyl ene-5-methyluridinyl-(3'→5')-2'-[cyanoethoxy(diisopropylamino) phosphino]thymidine methyl ester Tetrahydrofuran (0.2 ml) was added to an acetonitrile solution (0.6 ml) of the compound obtained in Example 8 (10.0 mg, 11 µmol) and diisopropylammonium tetrazolide (15.5 mg, 77 µmol), then 2-cyanoethyldiisopropylchlorophosphoroamidite (39.8 mg, 132 µmol), were added in a stream of nitrogen gas and the solution was stirred for 25 hrs at room temperature. The solvent was evaporated under reduced pressure. The residue compound was purified by silica gel column chromatography (ethyl acetate:triethylamine=99:1→ethyl acetate:ethanol:triethylamine=100:10:1). The product was reprecipitated with dichloroethane and n-hexane and the title compound was obtained as a white powder (3.8 mg, 3.5 µmol, 31%).

mp 113–116° C. $^{31}$P-NMR (CD$_3$OD) δ: 8.67, 8.77, 9.07, 9.28, 148.53, 148.93, 148.99, 149.03.

EXAMPLE 10

Synthesis of Oligonucleotide Analogues

By using a DNA synthesizer (manufactured by Pharmacia Co., Gene Assembler Plus), oligonucleotides were automatically synthesized in 0.2 µmol scale. Solvents and concentrations of reagents and phosphoramidite in each process of the production are identical to those in production of natural oligonucleotides. The solvents, reagents and phosphoramidites of natural nucleosides employed were those supplied from Pharmacia. The DMTr group of Universal QCPG (0.2 µmol, manufactured by Glen Research) was deprotected with trichloroacetic acid, and the hydroxy group produced was treated with the compound obtained in Example 9 or amidites used in the synthesis of natural nucleotides. This condensation process was repeated to obtain oligonucleotide analogues of desired sequences. The synthetic cycle was as follows;

Synthesis Cycle
1) Detritylation trichloroacetate/dichloromethane; 60 sec.
2) Coupling phosphoramidite (25 eq) tetrazole/acetonitrile; 2 min or 30 min.
3) Capping 1-methylimidazole/acetonitrile, anhydrous acetic acid/2,4,6-collidine/acetonitrle; 36 sec.
4) Oxidation iodine/water/pyridine/acetonitrile; 60 sec.

When the compound obtained in Example 9 was reacted in the above cycle 2, the reaction time was 30 min, and when other phosphoramidites were employed, the reaction time was 2 min. After the oligonucleotide having the desired sequence was synthesized, the synthetic cycle was conducted until cycle 1 described above, the dimethoxytrityl group at the 5' position was deprotected, and then, following conventional methods, the oligomer was cut off from its supporting substance with concentrated aqueous ammonia solution, the protecting group of cyanoethyl group on the phosphorus atom was deprotected, and the protecting groups on the nucleic acid bases were deprotected.

The oligomer was purified by reverse phase HPLC and the desired oligonucleotide was obtained.

According to this method, the oligonucleotide analogue 5'-tttttttttnt-3' (SEQ ID NO: 1 in the SEQUENCE LISTING), of which n in base number 11 was 3'-amino-3'deoxy-2'-O,4'-C-methylene-5-methyluridine (hereinafter called "oligonucleotide (1)") was obtained. (yield 8.5 nmol, 4.3%)

The obtained oligonucleotide analogues were purified by reverse phase HPLC (HPLC: Model 302, column manufactured by GILSON; CHEMCO CHEMCOBOND 5-ODS-H (7.8×300 mm); 0.1 M aqueous triethylamine acetate solution (TEAA), pH 7; 10→12.5% $CH_3CN$/40 min, linear gradient; 50° C.; 2.5 ml/min; 254 nm), and the fraction eluted at 25.4 min was collected.

EXAMPLE 11

Synthesis of Oligonucleotide Analogues

By using 5'O-dimethoxytrityl-N-4-benzoyl-5-methyl-2'deoxycytidine-3'-O-(2-cyanoethyl)N,N-diisopropylphosphoramidite (manufactured by Pharmacia CO.), a nucleotide analogue having the sequence represented as 5'-tttttmtntmt-mtmt-3' (SEQ ID NO: 2 in the SEQUENCE LISTING), in which m represents 5-methyl 2'-deoxycytidine and n represents 3'-amino-3'-deoxy-2'-O,4'-C-methylene-5-methyluridine, (hereinafter called "oligonucleotide (2)" was obtained (yield 7.1 nmol, 3.5%).

The modified oligonucleotide analogue which was obtained was purified with reverse phase HPLC (HPLC: Model 302, Column manufactured by GILSON; CHEMCO CHEMCOBOND 5-ODS-H (7.8×300 mm); 0.1 M aqueous solution of triethylamine acetate (TEAA), pH 7; 10→12% $CH_3CN$/40 min, linear gradient; 50° C.; 2.5 ml/min; 254 nm), and the fraction eluted at 22.5 min was collected.

EXAMPLE 12

3'-Amino-3'-deoxy-5'-O-tert-buthyldiphenylsilyl-2'-O,4'-C-methylene-5-methyl Uridine Exemplification Compound Number 2–72

Triphenylphosphine was added to an pyridine solution of compound obtained in Example 1 (50 mg, 0.09 mmol) in a stream of nitrogen gas and the solution was stirred for 100 minutes at room temperature. 28% ammonium in water (5 ml) was added to the solution and the resulting solution was stirred for 20 hours at room temperature. The solvent was evaporated and the residue was purified by silica gel column chromatography (chloroform:methanol=30:1) and the title compound was obtained as a white powder (49 mg, 100%).

mp 89–92° C. $^1$H-NMR(CDCl$_3$)δ: 1.12 (9H, s), 1.70 (3H, s), 3.33 (1H, s), 3.75, 3.80 (2H, ABq, J=8 Hz), 3.95, 4.07 (2H, ABq, J=8 Hz), 7.26–7.73 (10H, m), 8.08 (1H, s)

EXAMPLE 13

3'-Amino-3'-deoxy-5'-O-tert-buthyldiphenylsilyl-3'-N-(4-monomethoxytrithyl)-2'-O,4'-C-methylene-5-methyl Uridine Exemplification Compound Number 2–75

4-methoxytrithylchloride was added to an anhydrous pyridine solution of compound obtained Example 12 (102 mg, 0.20 mmol) in a stream of nitrogen gas and the solution was stirred for 10 hours at room temperature. Satuated aqueous $NaHCO_3$ solution was added to the solution and the mixture was partitioned. The organic phase was washed with satuated aqueous sodium chloride solution and dried over anhydrous sodium sulfate. The solvents were evaporated and the residue was purified by silica gel column chromatography (ethyl acetate n-hexane=1:3) to give the title compound as colorless powder (154 mg, 98%).

mp 102–105° C. $^1$H-NMR(CDCl$_3$)δ: 1.13 (9H, s), 1.62 (3H, s), 1.94 (1H, d, J=10 Hz), 2.48 (1H, s), 2.74(1H, d, J=10 Hz), 3.73 (3H, s), 3.83, 3.91 (2H, ABq, J=8 Hz), 4.25, 4.35 (2H, ABq, J=12 Hz), 5.36 (1H, s), 6.70 (2H, d, J=9 Hz), 7.02–7.75 (22H, m), 8.05 (1H, s)

EXAMPLE 14

3'-Amino-3'-deoxy-3'-N-(4-monomethoxytrithyl)-2'-O,4'-C-methyl ene-5-methyl Uridine Exemplification Compound Number 2–79

Anhydrous tetrabuthylammonium fluoride (10 M in THF, 0.21 ml, 0.21 mmol) was added to an anhydrous tetrahydrofuran solution of compound obtained Example 13 (147 mg, 0.19 mmol) in a stream of nitrogen gas and the solution was stirred for 4 hours at room temperature. The solvent was evaporated and the residue was purified by silica gel column chromatography (ethyl acetate:n-hexane=1:1→2:1→1:0) to give the title compound as colorless powder (97 mg, 96%).

mp 136–141° C. $^1$H-NMR(CDCl$_3$) δ: 1.77 (3H, s), 1.98 (1H, d, J=11 Hz), 2.36 (1H, s), 2.92(1H, d, J=10 Hz), 3.77, 3.91 (2H, ABq, J=7 Hz), 3.78 (1H, s), 4.19, 4.33 (2H, ABq, J=14 Hz), 5.37 (1H, s), 6.78 (2H, d, J=9 Hz), 7.20–7.45 (12H, m), 7.94 (1H, s).

EXAMPLE 15

3'-Amino-3'-deoxy-3'-N-(4-monomethoxytrithyl)-2'-O,4'-C-methyl ene-5-methyl Uridine-5'-O-(2-cyanoethyl-N,N-diisopropyl)phosphoramidite Exemplification Compound Number 2–83

Tetrahydrofuran (1 ml) was added to mixture solution of an acetonitrile solution of compound obtained in Example 14 (95 mg, 0.18 mmol) and an acetonitrile solution of diisopropylamine tetrazolide (42.5 mg, 0.25 mmol) in a stream of nitrogen gas. 2-cyanoethyl-N,N,N,N-tetraisopropylphosphoramidite (126.9 mg, 0.43 mmol) was added to the solution and stirred for 3 hours at room temperature. The solvent was evaporated and the residue was purified by silica gel column chromatography (ethyl acetate:n-hexane 1:1) to give the title compound as colorless oil (140 mg, quant.)

$^{13}$P-NMR(CDCl$_3$) δ: 148.61, 148.76

EXAMPLE 16

Synthesis of Oligonucleotide Analogues

By using a DNA synthesizer (manufactured by Applied Biosystem Co., Expedite 8909), oligonucleotides were automatically synthesized in 0.2 μmol scale. Solvents and concentrations of reagents and phosphoramidites in each process of the production are identical to those in production of natural oligonucleotides. The solvents, reagents and phosphoramidites of natural nucleosides employed were those supplied from Applied Biosystem except for especially noted. Oligonucleotides were synthesized from 5' end toward 3' end of nucleotide different from the ordinal process synthesized from 3' end toward 5' end. 5'-O-amidite derivative of natural timidine (dT-5'-CE-phosphoramidite, catalog No. 10-0101-05) was supplied from Glen Research. The DMTr group of Universal QCPG (0.2 μmol, manufactured by Glen Research) was deprotected with trichloroacetic acid, and the hydroxy group produced was treated with the compound obtained in Example 15 or amidites used in the synthesis of natural nucleotides. This condensation process was repeated to obtain oligonucleotide analogues of desired sequences.

The synthetic cycle was as follows:
Synthesis Cycle
1) Detrithlation trichloroacetate/dichloromethane; 49 sec.
2) Coupling phosphoramidite (ca. 35 eq.) tetrazole/acetonitrile 1.5 min or 10.5 min.
3) Capping 1-methylimidazole/tetrahydrofuran/pyridine, anhydrous acetic acid/tetrahydrofuran; 15 sec.
4) Oxidation iodine/water/pyridine/tetrahydrofuran; 6 sec.
5) Capping 1-methylimidazole/tetrahydrofuran/pyridine, anhydrous acetic acid/tetrahydrofuran; 2.5 sec.

When the compound obtained in Example 15 was reacted in the above cycle 2, the reaction time was 10.5 min, and when other phosphoramidites were employed, the reaction time was 1.5 min. After the oligonucleotides having the desired sequence was synthesized, the synthetic cycle was conducted until cycle 1 described above, the dimethoxytrithyl group at the 5' position was deprotected, and then, following conventional methods, the oligomer was cut off from its supporting substance with concentrated aqueous ammonia solution, the protecting group of cyanoethyl group on the phosphorous atom was deprotected, and the protecting groups on the nucleic acid bases were deprotected.

The oligomer was purified by reverse phase HPLC and the desired oligonucleotide was obtained. According to this method, the oligonucleotide analogue 5'-nnnnnnnnnn-3' (SEQ ID NO: 7 in the SEQUENCE LISTING), of which n was 3'-amino-3'-deoxy-2'-O,4'-C-methylene-5-methyluridine was obtained. (yield 9.4 nmol, 4.6%) The obtained oligonucleotide analogues were purified by reverse phase HPLC (HPLC: Model 302, column manufactured by GILSON; CHEMCOSORB 300-5C18 (7.5×250 mm); 0.1 M aqueous triethylamine acetate solution (TEAA), pH 7; 8→10% CH$_3$CN/30 min, linear gradient; 50° C.; 2.5 ml/min 254 nm), and the fraction eluted at 9.7 min was collected.

EXAMPLE 17

Synthesis of Oligonucleotide Analogues

According to the procedure described in Example 16 a nucleotide analogue having the sequence represented as 5'-ntntntntnt-3' (SEQ ID NO: 8 in the SEQUENCE LISTING) was obtained (yield 20 nmol, 10%). The obtained oligonucleotide analogues were purified by reverse phase HPLC (HPLC: Model 302, column manufactured by GILSON; CHEMCOSORB 300-5C18 (7.5×250 mm); 0.1 M aqueous triethylamine acetate solution (TEAA), pH 7; 8→11% CH$_3$CN/45 min, linear gradient; 50° C.; 2.5 ml/min; 254 nm), and the fraction eluted at 19.6 min was collected.

EXAMPLE 18

Synthesis of Oligonucleotide Analogues

According to the procedure described in Example 16 a nucleotide analogue having the sequence represented as 5'-tntntntntn-3' (SEQ ID NO: 9 in the SEQUENCE LISTING) was obtained (yield 30=mol, 15%). The obtained oligonucleotide analogues were purified by reverse phase HPLC (HPLC: Model 302, column manufactured by GILSON; CHEMCOSORB 300-5C18 (7.5×250 mm); 0.1 M aqueous triethylamineacetate solution (TEAA), pH 7; 8→11% CH$_3$CN/45 min, linear gradient; 50° C.; 2.5 ml/min; 254 nm), and the fraction eluted at 22.2 min was collected.

REFERENCE EXAMPLE 1

3-Azido-3-deoxy-4-hydroxymethyl-1,2-O-isopropylidene-α-D-ribofuranose

Potassium carbonate (380 mg, 2.75 mmol) and water (15 ml) were added to a methanol solution (85 ml) of 3-azido-4-benzoyloxymethyl-5-O-benzoyl-3-deoxy-1,2-O-isopropylidene-α-D-ribofuranose (4.13 g, 9.15 mmol) prepared in accordance with the literature (Surzhykov S. A., Krayevsky A. A., Nucleosides Nucleotides, 13, 2283–2305 (1994)) at 0° C., and the mixture was stirred for 4.5 hrs at 0° C. Then the reaction mixture was neutralized with 10% hydrochloric acid solution at 0° C., and the methanol was evaporated. Water was added to the residue, then, after extraction with ethyl acetate, the extracts were washed with saturated aqueous sodium chloride solution. The organic phase was dried over anhydrous sodium sulfate. The solvent was evaporated. The white solid obtained was washed with cold n-hexane and the desired compound was obtained as a white powder (1.93 g, 7.87 mmol, 86%).

mp 113–115° C. (toluene). IR vmax (KBr): 3460, 3417, 2989, 2951, 2907, 2111 cm$^{-1}$. $^1$H-NMR (CDCl$_3$) δ: 1.62 (3H, s), 1.35 (3H, s) 2.65 (2H, br s), 3.81, 3.65 (2H, AB, J=12 Hz), 3.59, 4.00 (2H, AB, J=12.5 Hz), 4.28 (1H, d, J=5.5 Hz), 4.82 (1H, dd, J=4 Hz, 5.5 Hz), 5.85 (1H, d, J=4 Hz). $^{13}$C-NMR (CDCl$_3$) δ: 25.7, 26.2, 61.9, 62.1, 63.2, 79.9, 87.3, 104.4, 113.6.

REFERENCE EXAMPLE 2

3-Azido-5-O-tert-butyldiphenylsilyl-3-deoxy-4-hydroxydimethyl-1,2-O-isopropylidene-α-D-ribofuranose Triethylamine (3.5 g, 4.82 ml, 34.6 mmol) and t-butyldiphenylsilyl chloride (9.75 g, 9.22 ml, 35.46 mmol) were added to an anhydrous methylene chloride solution (73 ml) of the compound obtained in Reference Example 1 (2.56 mg, 10.5 mmol) and the solution was stirred for 24 hrs at room temperature. Then saturated aqueous sodium hydrogen carbonate solution was added to the reaction mixture, and the resulting mixture was extracted with ethyl acetate and the extracts washed with saturated aqueous sodium chloride solution. The organic phase was dried over anhydrous sodium sulfate. After the solvent was evaporated, the residue was purified by silica gel column chromatography (ethyl acetate:n-hexane=1:6). The desired compound was obtained as a white powder (3.13 g, 6.47 mmol, 62%).

mp 99.5–100.5° C. (n-hexane). IR νmax (KBr) 3504, 2936, 2852, 2111 cm$^{-1}$. $^1$H-NMR (CDCl$_3$) δ: 1.07 (9H, s), 1.36 (3H, s), 1.62 (3H, s), 3.62, 3.92 (2H, AB, J=12 Hz), 4.38 (1H, d, J=6 Hz), 4.84 (1H, dd, J=4 Hz, 5.5 Hz), 3.82, 3.70 (2H, AB, J=11 Hz), 4.84 (1H, dd, J=4 Hz, 5.5 Hz), 5.86 (1H, d, J=4 Hz), 7.36–7.44 (6H, m), 7.64–7.67 (4H, m). $^{13}$C-NMR (CDCl$_3$) δ: 19.2, 26.1, 26.3, 26.8, 62.2, 62.3, 65.2, 80.4, 88.0, 104.5, 113.7, 127.7, 127.8, 129.8, 129.9, 132.7, 132.8, 135.5.

REFERENCE EXAMPLE 3

3-Azido-5-O-tert-butyldiphenylsilyl-3-deoxy-4-(p-toluenesulfon yloxymethyl)-1,2-O-isopropylidene-α-D-ribofuranose Triethylamine (137 mg, 180 μl, 1.29 mmol), p-toluenesulfonylchloride (63.3 mg, 0.33 mmol) and 4-dimethylaminopyridine (4 mg, 0.03 mmol) were added to an anhydrous methylene chloride solution (2 ml) of the compound obtained in Reference Example 2 (100 mg, 0.21 mmol) at 0° C. in a stream of nitrogen gas, and the solution was stirred for 14 hrs at room temperature. Then saturated aqueous sodium hydrogen carbonate solution was added to the reaction mixture, the resulting mixture was extracted with ethyl acetate and the extracts washed with saturated sodium chloride solution. The organic phase was dried over anhydrous sodium sulfate. After the solvent was evaporated, the residue was purified by silica gel column chromatography (ethylacetate:n-hexane=1:6). The desired compound was obtained as a white powder (130 mg, 0.20 mmol, 98%).

mp 122–124° C. (ethyl acetate-n-hexane). IR νmax (KBr): 3069, 2935, 2114, 1366, 1183, 1109 cm$^{-1}$· $^1$H-NMR (CDCl$_3$) δ: 1.03 (9H, s), 1.27 (3H, s), 1.31 (3H, s), 2.41 (3H, s), 3.60, 3.72 (2H, AB, J=10.5 Hz), 4.33, 4.40 (2H, AB, J=10 Hz), 4.55 (1H, d, J=5.5 Hz), 5.00 (1H, dd, J=3.7 Hz, 5.5 Hz), 5.82 (1H, d, J=3.7 Hz), 7.23 (2H, d, J=8.5 Hz), 7.36–7.45 (6H, m), 7.61–7.63 (4H, m), 7.72 (2H, d, J=8.5 Hz). $^{13}$C-NMR (CDCl$_3$) δ: 19.1, 21.5, 25.9, 26.0, 26.7, 63.1, 64.7, 68.9, 80.1, 85.6, 104.4, 113.8, 127.8, 128.0, 129.6, 129.9, 132.4, 132.5, 135.4, 144.6.

REFERENCE EXAMPLE 4

3-Azido-5-O-tert-butyldiphenylsilyl-3-deoxy-4-(p-toluenesulfon yloxymethyl)-1,2-di-O-acetyl-D-ribofuranose Acetic anhydride (406 mg, 375 μl, 3.98 mmol) and concentrated sulfuric acid (6.5 mg, 3.5 μl, 0.066 mmol) were added to an acetic acid solution (3.5 ml) of the compound obtained in Reference Example 3 (230 mg, 0.36 mmol) in a stream of nitrogen gas and the solution was stirred for 5 hrs at room temperature. Then ice-water was added to the reaction mixture, and after stirring for 30 min, saturated aqueous sodium chloride solution was added. The resulting mixture was extracted with ethyl acetate. The organic phase was dried over anhydrous sodium sulfate. After the solvent was evaporated, the residue was purified by silica gel column chromatography (ethyl acetate:n-hexane=4:1). The desired compound, which is a mixture of α:β=approximately 3:7, was obtained as a colorless oil (230 mg, 0.34 mmol, 94%).

IR νmax (KBr): 3048, 2935, 2864, 2117, 1756.cm$^{-1}$. $^1$H-NMR (CDCl$_3$) [β form] δ: 1.06 (9H, s), 1.83 (3H, s), 2.08 (3H, s), 2.40 (3H, s), 3.54, 3.80 (2H, AB, J=11 Hz), 4.12, 4.26 (2H, AB, J=10 Hz), 4.37 (1H, d, J=5.5 Hz), 5.32 (1H, d, J=5.5 Hz), 5.98 (1H, s), 7.29 (2H, d, J=8 Hz), 7.37–7.46 (6H, m), 7.59–7.65 (4H, m), 7.76 (2H, d, J=8 Hz). [α form] δ: 1.05 (9H, s), 2.02 (3H, s), 2.13(3H, s), 2.39 (3H, s), 3.51, 3.68 (2H, AB, J=11 Hz), 4.12, 4.21 (2H, AB, J=10.5 Hz), 4.40 (1H, d, J=7 Hz), 5.32 (1H, m), 6.31 (1H, d, J=4.5 Hz), 7.25 (2H, d, J=8.5 Hz), 7.37–7.46 (6H, m), 7.59–7.65 (4H, m), 7.70 (2H, d, J=8.5 Hz). $^{13}$C-NMR (CDCl$_3$) δ: 19.0, 19.1, 20.0, 20.6, 20.9, 21.1, 21.5, 26.6, 61.0, 63.2, 65.1, 68.4, 68.8, 72.2, 75.5, 85.4, 86.5, 93.6, 96.0, 97.3, 127.8, 127.9, 128.0, 129.6, 129.9, 130.0, 132.0, 132.3, 132.4, 135.4, 144.7, 168.5, 169.2, 169.3, 169.4.

REFERENCE EXAMPLE 5

2'O-Acetyl-3'-azido-5'-O-tert-butyldiphenylsilyl-3'-deoxy-4'-(p-toluenesulfonyloxymethyl)-5-methyluridine O,O'-Bis(trimethylsilyl)thymine (240 mg, 0.93 mmol) and tin tetrachloride (253 mg, 114 μl, 0.97 mmol) were added to an anhydrous 1,2-dichloroethane solution (6 ml) of the compound obtained in Reference Example 4 (300 mg, 0.44 mmol) at 0° C. in a stream of nitrogen gas, and the solution was stirred for 43 hrs at room temperature. After the reaction mixture was diluted with dichloromethane in an ice bath, saturated aqueous sodium hydrogen carbonate solution was added to the reaction mixture, which was then extracted with dichloromethane. The extracts were washed with saturated aqueous sodium chloride solution. After the organic phase was dried over anhydrous sodium sulfate, the solvent was evaporated and the residue was purified by silica gel column chromatography (ethyl acetate:n-hexane=1:2-1:0). The desired compound was obtained as a white powder (300 mg, 0.4 mmol, 91%).

mp 158.5–159.5° C. (ethyl acetate-n-hexane). $^1$H-NMR (CDCl$_3$) δ: 1.11 (9H, s), 1.59 (3H, s), 2.15 (3H, s), 2.41 (3H, s), 3.80, 3.84 (2H, AB, J=11.5 Hz), 4.04, 4.10 (2H, AB, J=11 Hz), 4.47 (1H, d, J=6 Hz), 5.53 (1H, t, J=6.5 Hz), 5.94 (1H, d, J=7 Hz), 7.18 (1H, s), 7.28 (2H, d, J=7.5 Hz), 7.37–7.47 (6H, m), 7.61–7.65 (4H, m), 7.71 (2H, d, J=7.5 Hz), 9.68 (1H, br s). $^{13}$C-NMR (CDCl$_3$) δ: 11.8, 19.2, 20.9, 21.5, 26.9, 62.3, 65.9, 68.3, 74.2, 84.8, 86.1, 118.9, 127.9, 128.0, 129.7, 130.1, 131.5, 132.2, 135.2, 135.3, 135.5, 145.0, 150.4, 163.6, 169.9.

REFERENCE EXAMPLE 6

3'-O-(tert-Butyldimethylsilyl)thymidine-5'-(2-cyanoethyl)phosphonate

2-Cyanoethyltetraisopropylphosphorodiamidite (132 mg, 0.44 mmol) was added over 5 min to an acetonitrile solution (4 ml) of 3'-O-(tert-butyldimethylsilyl)thymidine (described in K. M. Fries, C. Joswing and R. F. Borch, J. Med. Chem., 38, 2672 (1995)) (100 mg, 0.34 mmol) in a stream of nitrogen gas and the solution was stirred for 2.2 hrs at room temperature. Then, an acetonitrile solution (0.88 ml) of tetrazole (30.8 mg, 0.44 mmol) was added and the solution was stirred for 1.5 hr at room temperature. Water was added to the reaction mixture, which was extracted with dichloroethane. The organic phase was washed with saturated aqueous sodium chloride solution, and then dried over anhydrous sodium sulfate. The solvent was evaporated under reduced pressure and the crude product was purified by silica gel column chromatography (chloroform:methanol=30:1, n-hexane:ethyl acetate=1:5→0:1). The title compound was obtained as a colorless oil (98.4 mg, 0.21 mmol, 70%).

$^1$H-NMR (CDCl$_3$) δ: 0.10 (6H, s), 0.90 (9H, s), 1.96 (3H, s), 2.16–2.28 (2H, m), 2.77–2.82 (2H, m), 4.09–4.41 (6H, m), 6.28 (1H, dd, J=7 Hz, 11 Hz), 6.98 (1H, d, J=720 Hz), 7.36 (1H, d, J=8 Hz), 8.20(1H, brs). $^{31}$P-NMR (CDCl$_3$) δ: 7.70, 8.94.

REFERENCE EXAMPLE 7

3'-O-(tert-butyldimethylsilyl)thymidine-5'-methylphosphonate

Chlorodiisopropylaminomethoxyphosphine (69.2 mg, 0.35 mmol) was added over 5 min to a dichloromethane solution (2 ml) of 3'-O-(tert-butyldimethylsilyl)thymidine (100 mg, 0.28 mmol) in a stream of nitrogen gas, and the solution was stirred for 1 hrs at room temperature. Then, an acetonitrile solution (2 ml) of tetrazole (56.0 mg, 0.80 mmol) was added and the solution was stirred for 40 min at room temperature. Water was added to the reaction mixture, which was extracted with dichloroethane, and the organic phase was washed with saturated aqueous sodium chloride solution and was dried over anhydrous sodium sulfate. The solvent was evaporated under reduced pressure and the crude product was purified by silica gel column chromatography (n-hexane:ethyl acetate=1:1→0:1, n-hexane:ethyl acetate=1:4). The title compound was obtained as a colorless oil (109 mg, 0.25 mmol, 91%).

$^{31}$P-NMR (CDCl$_3$) δ: 9.13, 10.07.

TEST EXAMPLE 1

Measurement of Tm for Determination of Activity of Triplet Formation

A sample solution of equimolar amounts of oligonucleotide (2), which forms a triplet, and a natural oligonucleotide with double stranded DNA (final concentration of each nucleotide is 1.5 µM) in 7 mM sodium phosphate buffer solution (pH 7.0) containing 140 mM KCl and 10 mMMgCl$_2$ (or a solution without 10 mMMgCl$_2$) was immersed in a boiling water bath. Then the solution was cooled slowly to room temperature over 12 hrs, and further cooled to 4° C. and left at 4° C. for 1 hr. The sample solution in a cell of a spectrophotometer (Du650 manufactured by Beckman Instrument Inc.) was warmed gradually from 5° C. to 85° C. (0.5° C./min) and the ultraviolet absorption of the sample was determined at 260 nm. Natural oligonucleotides which have double stranded DNA with the sequence of 5'-gctaaaaa-gaaagagagatcg-3' (SEQ ID NO: 3 in the SEQUENCE LISTING) and its complementary strand with the sequence of 5'-cgatctctctttcttttagc-3' (SEQ ID NO: 4) were used.

Further, a natural oligonucleotide which forms a triplet, with the sequence of 5'ttttmtttmtmtmt-3' (SEQ ID NO: 5), in which m is 5-methyl-2'deoxycytidine (hereinafter referred to as "oligonucleotide (3)") was used.

The results of Tm measurements of double stranded DNA with oligonucleotide (2) and (3) are shown in Table 3.

TABLE 3

| Tm (° C.) | Oligonucleotide (2) Obtained in Example 11 | Oligonucleotide (3) |
|---|---|---|
| With MgCl$_2$ | 55 | 44 |
| Without MgCl$_2$ | 44 | 32 |

As clearly demonstrated, the above-tested oligonucleotide analogues of the present invention showed higher Tm values in triplets than natural oligonucleotide analogues. This indicates that oligonucleotide analogues of the present invention showed high activity in triplet formation.

TEST EXAMPLE 2

Determination of Tolerance to Nucleases 0.2 µg of 3'-exonuclease (phosphodiesterase from Crotalus durissus (Boehringer Mannheim)) was added to 320 µl of buffer solution (50 mM Tris (pH 8.0) and 10 mM MgCl$_2$) containing various oligonucleotides (10 µg) and the mixture was kept at 37° C. After a predetermined time, the enzyme activity was quenched by heating (90° C.) a portion of the resulting mixture for 2 min. The remaining amount of oligonucleotide in the resulting mixture was determined by reverse phase HPLC and the change in the amount of oligonucleotide over time was determined in the presence of nucleases. The results are shown in the Figure.

The ordinate in the Figure indicates ratio (%) of the amount of oligonucleotide remaining to the amount at 0 min. The abscissa in the Figure indicates time (min) after the beginning of the reaction.

Oligonucleotides Employed in the Test
1. Oligonucleotide (1) obtained in Example 10.
2. The nucleotide with a sequence of 5'-tttttttttnt-3' (SEQ ID NO: 1 in the SEQUENCE LISTING) in which n is 2'O,4-C-methylene-5-methyluridine (hereinafter referred to as "oligonucleotide (4)").
3. Natural oligonucleotide with a sequence of 5'-tttttttttttt-3' (SEQ ID NO: 6 in the SEQUENCE LISTING) (hereinafter referred to as "oligonucleotide (5)").

The tested oligonucleotide analogues of the present invention demonstrated remarkable nuclease resistance compared to the natural oligonucleotide analogues. Further, the oligonucleotide analogues of this invention were shown to exert more potent resistance to nucleases than known non-natural oligonucleotide analogues.

The hybrid forming activity and anti-HIV activity of the oligonucleotide analogues of the present invention were able to be determined by using the following methods.

Method 1

The melting temperatures (Tm values) of the annealing products between antisense strands, which are the various oligonucleotide analogues obtained, and natural DNA- or RNA-based sense strands are measured to investigate the hybridizing ability of the oligonucleotide analogues of the present invention for complementary DNA and RNA.

Each sample solution (500 µl) with final concentrations of 100 mM sodium chloride, 10 mM sodium phosphate buffer (pH 7.2), 4 µM antisense strand, and 4 µM sense strand, respectively, are heated in a boiling water bath, and slowly cooled to room temperature over 10 hours. The sample solution in a cell chamber of a spectrophotometer (UV-2100PC, manufactured by Shimadzu Cor.,) is gradually cooled to 5° C., kept at 5° C. for a further period of 20 minutes, and then the measurement is started, in a stream of nitrogen gas in order to prevent condensation of moisture. The sample temperature is raised at a rate of 0.2° C./minute until 90° C., and the ultraviolet absorption at 260 nm is measured at intervals of 0.1° C. In order to prevent changes of the sample concentration with increases in the temperature, a cell with a cover is used, and a drop of a mineral oil is applied on the surface of the sample solution during measurement.

Method 2

Determination of Anti-HIV Activity

Anti-HIV activities of the oligonucleotide analogues of the present invention are determined by a similar method to that described by R. Pauwel et al. (J. Virological Method, 20, p. 309–321 (1988)). The cell precipitate is suspended in RPMI-1640 medium which does not contain serum. To the suspension is added HIV and the mixture is incubated at 37° C. for 1 hour. At the end of this time the resulting mixture is washed with RPMI-1640 medium containing 10% fetal bovine serum (hereinafter called "serum medium") and centrifuged (1000×g, 5 min). The HIV infected cell thus obtained and HIV non-infected cells are suspended in the serum medium so as to have a concentration of $4 \times 10^5$/ml, respectively. After 100 μl of the suspension is placed in each well of a 96-well plate for tissue culture, they are incubated for 5 days at 37° C. in the presence of carbon dioxide gas without stirring. HIV infected cells and non-infected cells without test compounds are similarly incubated. After the incubation, the living cells are counted by using MTT (3-(4,5-dimethylthiazol-2-yl)-2,5-diphenyltetrazolium bromide) and cell injury inhibitory activities of test compounds are determined. It is confirmed that Mycoplasma is not contained in the cell solution and virus solution incubated.

Inhibitory activity of cell injury in HIV non-infected cells without a test compound is expressed as 100%, and inhibitory activity of cell injury in HIV infected cells without a test compound is expressed as 0%. The concentration of the compound to inhibit cell injury by 50% ($EC_{50}$) is determined.

Novel bicyclonucleoside analogues of the present invention exhibit excellent anti-sense or anti-gene activities and are useful as intermediates for producing oligonucleotide analogues with in vivo stability.

Further, novel oligonucleotide analogues of the present invention are stable in vivo and useful as an anti-sense or anti-gene agents.

Moreover, novel bicyclonucleoside analogues have anti-HIV activity and are useful as a therapeutic or prophylactic agents for AIDS.

```
                          SEQUENCE LISTING

<160> NUMBER OF SEQ ID NOS: 9

<210> SEQ ID NO 1
<211> LENGTH: 12
<212> TYPE: DNA
<213> ORGANISM: Artificial
<220> FEATURE:
<223> OTHER INFORMATION: Description of Artificial Sequence: Synthesized
                        oligonucleotide for testing the nuclease
                        resistance
<220> FEATURE:
<221> NAME/KEY: modified_base
<222> LOCATION: (11)
<223> OTHER INFORMATION: modified uridine

<400> SEQUENCE: 1 ttttttttttt nt                                                          12

<210> SEQ ID NO 2
<211> LENGTH: 15
<212> TYPE: DNA
<213> ORGANISM: Artificial
<220> FEATURE:
<223> OTHER INFORMATION: Description of Artificial Sequence: Synthesized
                        oligonucleotide for testing the formability of
                        a triple strand
<220> FEATURE:
<221> NAME/KEY: modified_base
<222> LOCATION: (6)
<223> OTHER INFORMATION: 5-methyl 2'-deoxycytidine
<220> FEATURE:
<221> NAME/KEY: modified_base
<222> LOCATION: (8)
<223> OTHER INFORMATION: 3'-amino-3'-deoxy-2'-O, 4'-C-methylene-5-
                        methyluridine
<220> FEATURE:
<221> NAME/KEY: modified_base
<222> LOCATION: (10)
<223> OTHER INFORMATION: 5-methyl 2'-deoxycytidine
```

```
<220> FEATURE:
<221> NAME/KEY: modified_base
<222> LOCATION: (12)
<223> OTHER INFORMATION: 5-methyl 2'-deoxycytidine
<220> FEATURE:
<221> NAME/KEY: modified_base
<222> LOCATION: (14)
<223> OTHER INFORMATION: 5-methyl 2'-deoxycytidine

<400> SEQUENCE: 2
tttttntntn tntnt                                                     15

<210> SEQ ID NO 3
<211> LENGTH: 21
<212> TYPE: DNA
<213> ORGANISM: Artificial
<220> FEATURE:
<223> OTHER INFORMATION: Description of Artificial Sequence: Synthesized
      oligonucleotide for testing the formability of
      a triple strand

<400> SEQUENCE: 3
gctaaaaaga aagagagatc g                                              21

<210> SEQ ID NO 4
<211> LENGTH: 21
<212> TYPE: DNA
<213> ORGANISM: Artificial
<220> FEATURE:
<223> OTHER INFORMATION: Description of Artificial Sequence: Synthesized
      oligonucleotide for testing the formability of
      a triple strand

<400> SEQUENCE: 4
cgatctctct ttcttttag c                                               21

<210> SEQ ID NO 5
<211> LENGTH: 15
<212> TYPE: DNA
<213> ORGANISM: Artificial
<220> FEATURE:
<223> OTHER INFORMATION: Description of Artificial Sequence: Synthesized
      oligonucleotide for testing the formability of
      a triple strand
<220> FEATURE:
<221> NAME/KEY: modified_base
<222> LOCATION: (6)
<223> OTHER INFORMATION: 5-methyl 2'-deoxycytidine
<220> FEATURE:
<221> NAME/KEY: modified_base
<222> LOCATION: (10)
<223> OTHER INFORMATION: 5-methyl 2'-deoxycytidine
<220> FEATURE:
<221> NAME/KEY: modified_base
<222> LOCATION: (12)
<223> OTHER INFORMATION: 5-methyl 2'-deoxycytidine
<220> FEATURE:
<221> NAME/KEY: modified_base
<222> LOCATION: (14)
<223> OTHER INFORMATION: 5-methyl 2'-deoxycytidine

<400> SEQUENCE: 5
tttttntttn tntnt                                                     15

<210> SEQ ID NO 6
<211> LENGTH: 12
<212> TYPE: DNA
<213> ORGANISM: Artificial
<220> FEATURE:
<223> OTHER INFORMATION: Description of Artificial Sequence: Synthesized
      oligonucleotide for testing the nuclease
```

-continued resistance

<400> SEQUENCE: 6
tttttttttt tt                                                            12

<210> SEQ ID NO 7
<211> LENGTH: 10
<212> TYPE: DNA
<213> ORGANISM: Artificial
<220> FEATURE:
<223> OTHER INFORMATION: Description of Artificial Sequence: Synthesized
      oligonucleotide for testing the formability of
      a triple strand
<220> FEATURE:
<221> NAME/KEY: modified_base
<222> LOCATION: (1)
<223> OTHER INFORMATION: 3'-amino-3'-deoxy-2'-O, 4'-C-methylene-5-
      methyluridine
<220> FEATURE:
<221> NAME/KEY: modified_base
<222> LOCATION: (2)
<223> OTHER INFORMATION: 3'-amino-3'-deoxy-2'-O, 4'-C-methylene-5-
      methyluridine
<220> FEATURE:
<221> NAME/KEY: modified_base
<222> LOCATION: (3)
<223> OTHER INFORMATION: 3'-amino-3'-deoxy-2'-O, 4'-C-methylene-5-
      methyluridine
<220> FEATURE:
<221> NAME/KEY: modified_base
<222> LOCATION: (4)
<223> OTHER INFORMATION: 3'-amino-3'-deoxy-2'-O, 4'-C-methylene-5-
      methyluridine
<220> FEATURE:
<221> NAME/KEY: modified_base
<222> LOCATION: (5)
<223> OTHER INFORMATION: 3'-amino-3'-deoxy-2'-O, 4'-C-methylene-5-
      methyluridine
<220> FEATURE:
<221> NAME/KEY: modified_base
<222> LOCATION: (6)
<223> OTHER INFORMATION: 3'-amino-3'-deoxy-2'-O, 4'-C-methylene-5-
      methyluridine
<220> FEATURE:
<221> NAME/KEY: modified_base
<222> LOCATION: (7)
<223> OTHER INFORMATION: 3'-amino-3'-deoxy-2'-O, 4'-C-methylene-5-
      methyluridine
<220> FEATURE:
<221> NAME/KEY: modified_base
<222> LOCATION: (8)
<223> OTHER INFORMATION: 3'-amino-3'-deoxy-2'-O, 4'-C-methylene-5-
      methyluridine
<220> FEATURE:
<221> NAME/KEY: modified_base
<222> LOCATION: (9)
<223> OTHER INFORMATION: 3'-amino-3'-deoxy-2'-O, 4'-C-methylene-5-
      methyluridine
<220> FEATURE:
<221> NAME/KEY: modified_base
<222> LOCATION: (10)
<223> OTHER INFORMATION: 3'-amino-3'-deoxy-2'-O, 4'-C-methylene-5-
      methyluridine

<400> SEQUENCE: 7 nnnnnnnnnn                                                               10

<210> SEQ ID NO 8
<211> LENGTH: 10
<212> TYPE: DNA
<213> ORGANISM: Artificial
<220> FEATURE:
<223> OTHER INFORMATION: Description of Artificial Sequence: Synthesized
      oligonucleotide for testing the formability of
      a triple strand

```
<220> FEATURE:
<221> NAME/KEY: modified_base
<222> LOCATION: (1)
<223> OTHER INFORMATION: 3'-amino-3'-deoxy-2'-O, 4'-C-methylene-5-
                         methyluridine
<220> FEATURE:
<221> NAME/KEY: modified_base
<222> LOCATION: (3)
<223> OTHER INFORMATION: 3'-amino-3'-deoxy-2'-O, 4'-C-methylene-5-
                         methyluridine
<220> FEATURE:
<221> NAME/KEY: modified_base
<222> LOCATION: (5)
<223> OTHER INFORMATION: 3'-amino-3'-deoxy-2'-O, 4'-C-methylene-5-
                         methyluridine
<220> FEATURE:
<221> NAME/KEY: modified_base
<222> LOCATION: (7)
<223> OTHER INFORMATION: 3'-amino-3'-deoxy-2'-O, 4'-C-methylene-5-
                         methyluridine
<220> FEATURE:
<221> NAME/KEY: modified_base
<222> LOCATION: (9)
<223> OTHER INFORMATION: 3'-amino-3'-deoxy-2'-O, 4'-C-methylene-5-
                         methyluridine

<400> SEQUENCE: 8 ntntntntnt                                                           10

<210> SEQ ID NO 9
<211> LENGTH: 10
<212> TYPE: DNA
<213> ORGANISM: Artificial
<220> FEATURE:
<223> OTHER INFORMATION: Description of Artificial Sequence: Synthesized
                         oligonucleotide for testing the formability of
                         a triple strand
<220> FEATURE:
<221> NAME/KEY: modified_base
<222> LOCATION: (2)
<223> OTHER INFORMATION: 3'-amino-3'-deoxy-2'-O, 4'-C-methylene-5-
                         methyluridine
<220> FEATURE:
<221> NAME/KEY: modified_base
<222> LOCATION: (4)
<223> OTHER INFORMATION: 3'-amino-3'-deoxy-2'-O, 4'-C-methylene-5-
                         methyluridine
<220> FEATURE:
<221> NAME/KEY: modified_base
<222> LOCATION: (6)
<223> OTHER INFORMATION: 3'-amino-3'-deoxy-2'-O, 4'-C-methylene-5-
                         methyluridine
<220> FEATURE:
<221> NAME/KEY: modified_base
<222> LOCATION: (8)
<223> OTHER INFORMATION: 3'-amino-3'-deoxy-2'-O, 4'-C-methylene-5-
                         methyluridine
<220> FEATURE:
<221> NAME/KEY: modified_base
<222> LOCATION: (10)
<223> OTHER INFORMATION: 3'-amino-3'-deoxy-2'-O, 4'-C-methylene-5-
                         methyluridine

<400> SEQUENCE: 9 tntntntntn                                                           10
```

What is claimed is:

1. A compound of formula (1) or a pharmaceutically acceptable salt thereof,

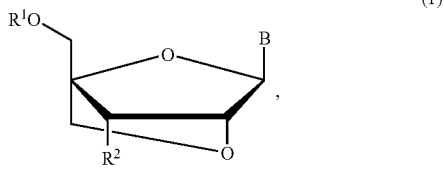

wherein $R^1$ selected from the group consisting of a hydrogen atom, a protecting group for a hydroxy group in nucleic acid synthesis, a phosphoric acid group, a phosphoric acid group protected with a protecting group in nucleic acid synthesis, and a group represented by the formula —P($R^{4a}$)$R^{4b}$, wherein $R^{4a}$ and $R^{4b}$ are the same or different and each represents a hydroxy group, a hydroxy group protected with a protecting group in nucleic acid synthesis, a mercapto group, a mercapto group protected with a protecting group in nucleic acid synthesis, an amino group, an amino group protected with a protecting group in nucleic acid synthesis, an alkoxy group having 1–6 carbon atoms, an alkylthio group having 1–6 carbon atoms, a cyanoalkoxy group having 1–7 carbon atoms, or an amino group substituted by an alkyl group having 1–6 carbon atoms, $R^2$ represents an azido group, an amino group, or a group represented by the formula —NH—$R^3$, wherein $R^3$ selected from the group consisting of a protecting group for an amino group in nucleic acid synthesis, a phosphoric acid group, a phosphoric acid group protected with a protecting group in nucleic acid synthesis, and a group represented by the formula —P($R^{4a}$)$R^{4b}$, wherein $R^{4a}$ and $R^{4b}$ are the same or different and each represents a hydroxy group, a hydroxy group protected with a protecting group in nucleic acid synthesis, a mercapto group, a mercapto group protected with a protecting group in nucleic acid synthesis, an amino group, an amino group protected with a protecting group in nucleic acid synthesis, an alkoxy group having 1–6 carbon atoms, an alkylthio group having 1–6 carbon atoms, a cyanoalkoxy group having 1–7 carbon atoms or an amino group substituted by an alkyl group having 1–6 carbon atoms, B represents a purin-9-yl group or a 2-oxo-1,2-dihydropyrimidin-1-yl group each of which is unsubstituted or substituted with 1 or more substituents selected from the group consisting of a hydroxy group, a hydroxy group protected with a protecting group in nucleic acid synthesis, an alkoxy group having 1–6 carbon atoms, a mercapto group, a mercapto group protected with a protecting group in nucleic acid synthesis, an alkylthio group having 1–6 carbon atoms, an amino group, an amino group protected with a protecting group in nucleic acid synthesis, an amino group substituted by an alkyl group having 1–6 carbon atoms, an alkyl group having 1–6 carbon atoms and halogen atom.

2. The compound according to claim 1, wherein $R^1$ represents a hydrogen atom, an aliphatic acyl group, an aromatic acyl group, a silyl group, a methyl group substituted by 1 to 3 aryl groups, or a methyl group substituted by 1 to 3 aryl groups wherein the aryl rings thereof are substituted by a lower-alkyl group, a lower-alkoxy group, a halogen atom or a cyano group.

3. The compound according to claim 1, wherein $R^1$ represents a hydrogen atom, a silyl group, a methyl group substituted by 1 to 3 aryl groups, or a methyl group substituted by 1 to 3 aryl groups wherein the aryl rings thereof are substituted by a lower-alkyl group, a lower-alkoxy group, a halogen atom or a cyano group.

4. The compound according to claim 1, wherein $R^1$ represents a hydrogen atom, a trimethylsilyl group, a t-butyldimethylsilyl group, a t-butyldiphenylsilyl group, a benzyl group, a triphenylmethyl group, a 4-methoxybenzyl group, a 4-methoxyphenyldiphenylmethyl group, a 4,4'-dimethoxytriphenylmethyl group, or a 4,4',4''-trimethoxytriphenylmethyl group.

5. The compound according to claim 1, wherein $R^2$ represents an azido group, an amino group, or a group represented by the formula —NH—$R^3$, wherein $R^3$ represents an aliphatic acyl group, an aromatic acyl group, a methyl group substituted by 1 to 3 aryl groups, a methyl group substituted by 1 to 3 aryl groups wherein the aryl rings thereof are substituted by a lower-alkyl group, a lower-alkoxy group, a halogen atom, or a cyano group, a silyl group, a phosphoramidite group, a phosphonyl group, a phosphoric acid group or a phosphoric acid group protected with a protecting group in nucleic acid synthesis.

6. The compound according to claim 1, wherein $R^2$ represents an azido group, an amino group, or a group represented by the formula —NH—$R^3$, wherein $R^3$ represents an acetyl group, a trifluoroacetyl group, a benzoyl group, a benzyl group, a p-methoxybenzyl group, a tert-butyldiphenylsilyl group, a group represented by the formula —P(OC$_2$H$_4$CN)(NCH(CH$_3$)$_2$), a group represented by the formula —P(OCH$_3$)(NCH(CH$_3$)$_2$), a phosphonyl group, a 2-chlorophenylphosphonic acid group or a 4-chlorophenylphosphonic acid group.

7. The compound according to claim 1, wherein $R^2$ represents an azido group or an amino group.

8. The compound according to claim 1, wherein B represents 6-aminopurin-9-yl, 6-amino-purin-9-yl wherein the amino group is protected with a protecting group in nucleic acid synthesis, 2,6-diaminopurin-9-yl wherein one or both amino groups are protected with a protecting group in nucleic acid synthesis, 2-amino-6-chloropurin-9-yl, 2-amino-6-chloropurin-9-yl wherein the amino group is protected with a protecting group in nucleic acid synthesis, 2-amino-6-fluoropurin-9-yl, 2-amino-6-fluoropurin-9-yl wherein the amino group is protected with a protecting group in nucleic acid synthesis, 2-amino-6-bromopurin-9-yl, 2-amino-6-bromopurin-9-yl wherein the amino group is protected with a protecting group in nucleic acid synthesis, 2-amino-6-hydroxypurin-9-yl, 2-amino-6-hydroxypurin-9-yl wherein the amino group is protected with a protecting group in nucleic acid synthesis, 6-amino-2-methoxypurin-9-yl, 6-amino-2-methoxypurin-9-yl wherein the amino group is protected with a protecting group in nucleic acid synthesis, 6-amino-2-chloropurin-9-yl, 6-amino-2-chloropurin-9-yl wherein the amino group is protected with a protecting group in nucleic acid synthesis, 6-amino-2-fluoropurin-9-yl, 6-amino-2-fluoropurin-9-yl wherein the amino group is protected with a protecting group in nucleic acid synthesis, 2,6-dimethoxypurin-9-yl, 2,6-dichloropurin-9-yl, 6-mercaptopurin-9-yl, 6-mercaptopurin-9-yl wherein the mercapto group is protected with a protecting group in nucleic acid synthesis, 2-oxo-4-amino-1,2-dihydropyrimidin-1-yl, 2-oxo-4-amino-1,2-dihydropyrimidin-1-yl wherein the amino group is protected with a protecting group in nucleic acid synthesis, 4-amino-2-oxo-5-fluoro-1,2-dihydropyrimidin-1-yl, 4-amino-2-oxo-5-fluoro-1,2-dihydropyrimidin-1-yl wherein the amino group is protected with a protecting group in nucleic acid synthesis, 4-amino-2-oxo-5-chloro-1,2-dihydropyrimidin-1-yl, 4-amino-2-oxo-5-chloro-1,2-dihydropyrimidin-1-yl wherein the amino group is protected with a protecting group in nucleic acid synthesis, 2-oxo-4-methoxy-1,2-dihydropyrimidin-1-yl, 2-oxo-4-mercapto-1,2-dihydropyrimidin-1-yl, 2-oxo-4-mercapto-1,2-dihydropyrimidin-1-yl wherein the mercapto group is protected with a protecting group in nucleic acid synthesis, 2,4-dihydroxypyrimidin-1-yl, 2,4-dihydroxy-5-methylpyrimidin-1-yl, 4-amino-5-methyl-2-oxo-1,2-dihydropyrimidin-1-yl, or 4-amino-5-methyl-2-oxo-1,2-dihydropyrimidin-1-yl group wherein the amino group is protected with a protecting group in nucleic acid synthesis.

9. The compound according to claim 1, wherein B represents 6-benzoylaminopurin-9-yl, adeninyl, 2-benzoylamino-6-hydroxypurin-9-yl, guaninyl, 2-oxo-4-benzoylamino-1,2-dihydropyrimidin-1-yl, cytosinyl, uracilyl or thyminyl.

10. The compound according to claim 1, wherein the compound is 3'-amino-3'-deoxy-2'-O,4'-C-methylene-5-methyluridine.

11. A compound of the formula (1):

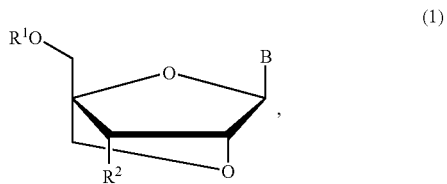

wherein $R^1$ represents a hydrogen atom or a protecting group for a hydroxy group;
$R^2$ represents an azido group or an amino group that optionally is protected; and
B represents a purin-9-yl group or a pyrimidin-1-yl group, each of which is unsubstituted or substituted with 1 or more substituents selected from the group consisting of
a halogen atom
an alkoxy group having from 1 to 6 carbon atoms,
a hydroxyl group which may be protected,
a mercapto group which may be protected,
an amino group which may be protected,
an alkoxy group having from 1 to 6 carbon atoms,
a mono-alkylamino group, the alkyl group of which having 1 to 6 carbon atoms and a di-alkylamino group, the alkyl group of which has from 1 to 6 carbon atoms.

12. The compound according to claim 1, wherein the compound is 3'-azido-3'-deoxy-2'-O,4'-C-methylene-5-methyluridine.

13. The compound according to claim 1, wherein the compound is 3'-azido-5'-O-tert-butyldiphenylsilyl-3'-deoxy-2'-O,4'-C-methylene-5-methyluridine.

14. The compound according to claim 1, wherein the compound is 3'-azido-3'-deoxy-5'-O-(4,4'-dimethoxytrityl)-2'-O,4'-C-methylene-methyluridine.

15. The compound according to claim 1, wherein the compound is 3'-amino-3'-deoxy-5'-O-(4,4'-dimethoxytrityl)-2'-O,4'-C-methylene-methyluridine.

16. The compound according to claim 1, wherein the compound is 3'-amino-3'-deoxy-N(4-monomethoxytrityl)-2'-O,4-C-methylene-5-methyluridine-5-O-(2-cyanoethyl-N,N-disopropyl)-phosphramidite.

* * * * *

UNITED STATES PATENT AND TRADEMARK OFFICE
CERTIFICATE OF CORRECTION

PATENT NO.       : 7,217,805 B2                                    Page 1 of 1
APPLICATION NO.  : 10/054300
DATED            : May 15, 2007
INVENTOR(S)      : Imanishi et al.

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by (1033) days Delete the phrase "by 1033" and insert -- by 1119 days--

Signed and Sealed this

Second Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,217,805 B2  Page 1 of 1
APPLICATION NO. : 10/054300
DATED : May 15, 2007
INVENTOR(S) : Takeshi Imanishi et al.

It is certified that error appears in the above-identified patent and that said Letters Patent is hereby corrected as shown below:

Column 63, Line 30 middle of page after SEQUENCE LISTING, delete

"<160> NUMBER OF SEQ ID NOS:9";

Column 63, Line 31-40 middle of the page, after SEQUENCE LISTING, insert

--<110> Imanishi, Takeshi
       Obika, Satoshi
<120> Novel Bicyclonucleoside Analogues
<130> 01834CIP/HG
<140> US 10/054,300
<141> 2002-01-22
<150> JP HEI 11-207170
<151> 1999-07-22
<160> 9
<170> PatentIn version 3.1--

Signed and Sealed this

Sixteenth Day of March, 2010

David J. Kappos
*Director of the United States Patent and Trademark Office*